United States Patent
Pepper et al.

(10) Patent No.: US 11,717,432 B2
(45) Date of Patent: Aug. 8, 2023

(54) NASAL DILATOR DEVICES

(71) Applicant: ASAP Breatheassist Pty Ltd, Armadale (AU)

(72) Inventors: Elizabeth Jane Pepper, Brunswick (AU); Michael Ralph Burgess Johnson, Hawthorn (AU); Justin Robert Armistead, The Basin (AU); Toby James Hartley, Ferntree Gully (AU); George Kotsiopoulos, Edithvale (AU)

(73) Assignee: ASAP Breatheassist Pty Ltd, Cremorne (AU)

( * ) Notice: Subject to any disclaimer, the term of this patent is extended or adjusted under 35 U.S.C. 154(b) by 165 days.

(21) Appl. No.: 15/319,941

(22) PCT Filed: Jan. 30, 2015

(86) PCT No.: PCT/AU2015/050032
§ 371 (c)(1),
(2) Date: Dec. 19, 2016

(87) PCT Pub. No.: WO2015/192173
PCT Pub. Date: Dec. 23, 2015

(65) Prior Publication Data
US 2017/0172783 A1      Jun. 22, 2017

(30) Foreign Application Priority Data

Jun. 20, 2014   (WO) ................ PCT/AU2014/000649

(51) Int. Cl.
*A61F 5/08*        (2006.01)
*A61M 29/00*     (2006.01)
(Continued)

(52) U.S. Cl.
CPC ............. *A61F 5/08* (2013.01); *A61M 15/085* (2014.02); *A61M 21/02* (2013.01); *A61M 29/00* (2013.01);
(Continued)

(58) Field of Classification Search
CPC ... A61F 5/08; A61F 5/56; A61B 17/24; A61B 2017/246; A61B 2017/248; A62B 23/06;
(Continued)

(56) References Cited

U.S. PATENT DOCUMENTS

| 851,048 A | 4/1907 | Woodward |
| 1,034,566 A | 8/1912 | Barratt |

(Continued)

FOREIGN PATENT DOCUMENTS

| AU | 2013204827 A1 * | 2/2014 |
| AU | 2013204827 A1 | 2/2014 |

(Continued)

OTHER PUBLICATIONS

International Preliminary Report on Patentability in PCT/AU2014/000649, dated Oct. 12, 2016, 5 pages.
(Continued)

*Primary Examiner* — Kathleen S Holwerda
(74) *Attorney, Agent, or Firm* — Servilla Whitney LLC

(57) ABSTRACT

A nasal dilator device comprises a substantially U-shaped body including a central portion arranged to span a septum of a nose when worn by a user and first and second leg members extending from the central portion in a first plane, a first cantilever rib member extending outward from the U-shaped body in a second plane and a second 5 cantilever rib member extending outward from the U-shaped body in a third plane, wherein the first and second cantilever rib members extend away from each other. The nasal dilator device further comprises a first intermediate section con- (Continued)

necting an end of the first leg member to a proximal end of the first cantilever rib member, wherein the first intermediate section extends from the first plane to the second plane; and a second intermediate section connecting an end of the second leg member to a proximal end of the second cantilever rib member, wherein the second intermediate section extends from the first plane to the third plane and at least one projection protruding from and extending along at least a portion of a length of each of the first and second cantilever rib members.

31 Claims, 22 Drawing Sheets

(51) Int. Cl.
    *A61M 15/08*     (2006.01)
    *A61M 21/02*     (2006.01)
    *A61M 31/00*     (2006.01)
    *A61M 21/00*     (2006.01)

(52) U.S. Cl.
    CPC ..... *A61M 31/00* (2013.01); *A61M 2021/0016* (2013.01); *A61M 2205/75* (2013.01); *A61M 2210/0618* (2013.01)

(58) Field of Classification Search
    CPC .... A61M 15/085; A61M 15/08; A61M 21/02; A61M 31/00; A61M 2021/0016; A61M 2210/0618; A61M 29/00; A61M 2205/75
    USPC ..................... 606/204.45; D24/135
    See application file for complete search history.

(56) References Cited

U.S. PATENT DOCUMENTS

| | | | |
|---|---|---|---|
| 1,077,574 A * | 11/1913 | Woodward | A61F 5/08 606/199 |
| 1,255,578 A * | 2/1918 | Boxley | A61F 5/08 606/199 |
| 1,481,581 A * | 1/1924 | Woodward | A61F 5/08 606/199 |
| 2,243,360 A * | 5/1941 | Slatis | A61M 15/08 128/206.11 |
| 3,710,799 A | 1/1973 | Caballero | |
| 3,722,509 A | 3/1973 | Nebel | |
| 3,905,335 A * | 9/1975 | Kapp | A62B 23/06 128/206.11 |
| 4,414,977 A | 11/1983 | Rezakhany | |
| 4,576,168 A | 3/1986 | Jalowayski | |
| 4,592,357 A | 6/1986 | Ersek | |
| 4,759,365 A | 7/1988 | Askinazy | |
| 5,059,193 A | 10/1991 | Kuslich | |
| 5,099,857 A | 3/1992 | Baldo et al. | |
| 5,423,858 A | 6/1995 | Bolanos et al. | |
| RE35,408 E * | 12/1996 | Petruson | A61F 5/08 128/858 |
| 5,683,465 A | 11/1997 | Shinn et al. | |
| 5,693,100 A | 12/1997 | Pisharodi | |
| 5,787,884 A | 8/1998 | Tovey | |
| 5,895,409 A | 4/1999 | Mehdizadeh | |
| 5,931,852 A * | 8/1999 | Brennan | A61F 5/08 606/199 |
| 5,955,376 A | 9/1999 | Tovey | |
| 6,109,262 A | 8/2000 | Tovey | |
| 6,129,763 A | 10/2000 | Chauvin et al. | |
| 6,270,512 B1 | 8/2001 | Rittmann | |
| 6,436,142 B1 | 8/2002 | Paes et al. | |
| 6,561,188 B1 | 5/2003 | Ellis | |
| 6,562,057 B2 | 5/2003 | Santin | |
| 6,626,179 B1 | 9/2003 | Pedley | |
| 6,821,298 B1 | 11/2004 | Jackson | |
| 6,978,781 B1 * | 12/2005 | Jordan | A61F 5/08 128/206.11 |
| 7,055,523 B1 * | 6/2006 | Brown | A61F 5/08 128/206.11 |
| 7,105,008 B2 | 9/2006 | Maryanka | |
| 7,108,198 B2 * | 9/2006 | Altadonna, Jr. | A61K 9/0043 128/200.24 |
| 7,318,438 B2 * | 1/2008 | Brown | A61F 5/08 128/206.11 |
| 7,390,331 B2 | 6/2008 | Santin et al. | |
| D575,397 S * | 8/2008 | Noce | D24/135 |
| 7,461,651 B2 * | 12/2008 | Brown | A61F 5/08 128/200.24 |
| 7,727,252 B2 | 6/2010 | Maryanka | |
| 7,740,643 B2 | 6/2010 | Maryanka | |
| 7,918,224 B2 * | 4/2011 | Dolezal | A62B 23/06 128/205.27 |
| 8,048,102 B2 * | 11/2011 | Thomas | A61F 5/08 606/199 |
| D652,143 S * | 1/2012 | Brown | D24/135 |
| 8,262,688 B2 | 9/2012 | Santin et al. | |
| 8,403,954 B2 | 3/2013 | Santin et al. | |
| 8,491,622 B2 | 7/2013 | Brown | |
| 8,833,369 B2 * | 9/2014 | Dolezal | A61M 15/08 128/206.11 |
| 8,834,512 B1 * | 9/2014 | Brown | A61F 5/08 606/199 |
| D726,312 S * | 4/2015 | Johnson | D24/135 |
| D819,205 S | 5/2018 | Snyder | |
| 2003/0086825 A1 * | 5/2003 | Brennan | G01N 31/223 422/83 |
| 2003/0106555 A1 | 6/2003 | Tovey | |
| 2003/0144684 A1 | 7/2003 | Ogle | |
| 2004/0079814 A1 * | 4/2004 | Altadonna, Jr. | A61K 9/0043 239/34 |
| 2004/0111109 A1 | 6/2004 | Ruiz | |
| 2005/0021073 A1 | 1/2005 | Santin et al. | |
| 2005/0278028 A1 | 12/2005 | Mujwid | |
| 2006/0185676 A1 * | 8/2006 | Brown | A61F 5/08 128/207.18 |
| 2006/0185677 A1 * | 8/2006 | Brown | A61F 5/08 128/207.18 |
| 2006/0207598 A1 * | 9/2006 | Thomas | A61F 5/08 128/206.11 |
| 2006/0259064 A1 * | 11/2006 | Maryanka | A61B 17/24 606/199 |
| 2006/0266367 A1 * | 11/2006 | Noce | A61F 5/08 128/207.18 |
| 2007/0107731 A1 * | 5/2007 | Reed | A61F 5/08 128/206.11 |
| 2008/0167676 A1 * | 7/2008 | Howard | A61F 5/56 606/199 |
| 2008/0178873 A1 * | 7/2008 | Alpers | A61F 5/08 128/200.24 |
| 2009/0194100 A1 | 8/2009 | Minagi | |
| 2009/0198268 A1 | 8/2009 | Case | |
| 2010/0042134 A1 | 2/2010 | Wien | |
| 2010/0063523 A1 | 3/2010 | Menard et al. | |
| 2010/0063532 A1 | 3/2010 | Moore | |
| 2010/0087749 A1 | 4/2010 | Tovey | |
| 2011/0118775 A1 * | 5/2011 | Brown | A61F 5/08 606/199 |
| 2012/0111340 A1 | 5/2012 | Robitaille | |
| 2012/0279504 A1 | 11/2012 | Moore | |
| 2012/0330345 A1 * | 12/2012 | Tasca | A61F 5/08 606/199 |
| 2013/0081637 A1 * | 4/2013 | Foley | A61F 5/08 128/848 |
| 2013/0081639 A1 * | 4/2013 | Bergstrand Borjegren | A61M 15/08 128/858 |
| 2013/0144325 A1 * | 6/2013 | Allegra | A61F 5/08 606/199 |
| 2013/0211275 A1 | 8/2013 | Curti | |
| 2013/0296809 A1 | 11/2013 | Santin et al. | |
| 2014/0128904 A1 * | 5/2014 | Mezzoli | A61F 5/08 606/199 |

(56) References Cited

U.S. PATENT DOCUMENTS

| | | | |
|---|---|---|---|
| 2014/0246023 A1* | 9/2014 | Maryanka | A61F 5/08 128/203.22 |
| 2015/0000675 A1* | 1/2015 | Kallikounis | A61F 5/08 128/848 |
| 2015/0196420 A1* | 7/2015 | Ede | A61M 31/002 604/285 |

FOREIGN PATENT DOCUMENTS

| | | |
|---|---|---|
| AU | 2013205674 A1 | 2/2014 |
| CA | 2566268 A1 | 11/2004 |
| CN | 103520815 A | 1/2014 |
| EP | 1917993 A1 | 5/2008 |
| EP | 2387978 A2 | 11/2011 |
| EP | 2114326 B1 | 3/2014 |
| EP | 1968684 B1 | 2/2016 |
| JP | H11192251 A | 7/1999 |
| KR | 100893945 B1 | 4/2009 |
| WO | 88/09149 A1 | 12/1988 |
| WO | 96/06657 A1 | 3/1996 |
| WO | 96/07099 A1 | 3/1996 |
| WO | 99/36773 A1 | 7/1999 |
| WO | 00/78223 A1 | 12/2000 |
| WO | 01/62342 A1 | 8/2001 |
| WO | 02/31465 A1 | 4/2002 |
| WO | 02/059569 A1 | 8/2002 |
| WO | 2004026391 A1 | 4/2004 |
| WO | 2007119041 A1 | 10/2007 |
| WO | 2008/091782 A2 | 7/2008 |
| WO | 2008109873 A2 | 9/2008 |
| WO | 2009/124567 A1 | 10/2009 |
| WO | 2011/104660 A2 | 9/2011 |
| WO | 2012/137182 A2 | 10/2012 |
| WO | 2014015359 A1 | 1/2014 |
| WO | 2014183966 A1 | 11/2014 |

OTHER PUBLICATIONS

International Preliminary Report on Patentability in PCT/AU2015/050032, dated Dec. 20, 2016, 4 pages.
International Search Report in PCT/AU2014/000649, dated Sep. 18, 2014, 7 pages.
International Search Report in PCT/AU2015/050032, dated Apr. 17, 2015, 5 pages.
Written Opinion of the International Searching Authority in PCT/AU2014/000649, dated Sep. 18, 2014, 7 pages.
Written Opinion of the International Searching Authority in PCT/AU2015/050032, dated Apr. 17, 2015, 3 pages.
International Preliminary Report on Patentability in Int. Appln. No. PCT/AU2016/050621, completed Nov. 21, 2017, 22 pages.
International Search Report in Int. Appln. No. PCT/AU2016/050621, dated Oct. 25, 2016, 7 pages.
International Search Report in International Application No. PCT/AU2015/050314, dated Aug. 12, 2015, 4 pages.
Non-Finai Office Action in U.S. Appl. No. 15/319,940, dated Apr. 6, 2018, 41 pages.
Written Opinion of the International Searching Authority in Int. Appln. No. PCT/AU2016/050621, dated Oct. 25, 2016, 7 pages.
Written Opinion of the International Searching Authority in International Application No. PCT/AU2015/050314, dated Aug. 12, 2015, 4 pages.
Airware Labs, retrieved from the internet Jul. 9, 2018, <URL: https://web.archive.org/web/20120522113321/http://www.airwarelab.com/>, published Mar. 22, 2012, 5 pages.
Breathe EZ Anti-Snoring Medical Nasal Device—Snoring Cure, retrieved from the internet on Jul. 9, 2018, <URL: https://web.archive.org/web/20120618221246/http://www.snoringcure.ca/breathe_ez_nasal_anti_snoring_medical_device.htm>, published May 14, 2007, 1 page.
Breathe-Aide, retrieved from the internet Jul. 9, 2018, <URL: https://web.archive.org/web/20141108204923/http://breatheaide.fm.alibaba.com/>, published Nov. 8, 2014, 1 page.
Breathe-Ezy Nasal Filters, retrieved from the internet Jul. 9, 2018, <URL: https://web.archive.org/web/20120615192635/http://www.breathe-ezy.com.au/>, published Apr. 29, 2005, 6 pages.
Breathing Relief Nasal Dilator, retrieved from the internet Jul. 9, 2018, <URL: https://web.archive.org/web/20120413210250/http://www.breathingrelief.com/>, published Jun. 16, 2006, 2 pages.
ClipAir® Anti-Snoring Nasal Dilator Device/Contre le Ronflement, retrieved from the internet on Jul. 9, 2018, <URL: https://web.archive.org/web/20120618061055/http://www.snoringcure.ca/clipair_nasal_anti_snoring_medical_dilator_device.htm>, published Aug. 1, 2010, 2 pages.
Flents Breathe Quiet! Nasal Dilator—Stop Snoring!, retrieved from the internet on Jul. 9, 2018, <URL: https://web. archive.org/web/20120425220535/http://www.amazon.co m/Flents-Breathe-Quiet-Nasal-Dilator/dp/B0019IHLR2>, published Aug. 29, 2010, 4 pages.
Flents Breathe Well Nasal Dilator—the Alternative to Nasal Strips, retrieved from the internet Jul. 9, 2018, <URL: https://web.archive.org/web/20120411195907/http://www.amazon.com/Flents-Breathe-Well-Nasal-Dialator/dp/B001J4K5E2>, published Feb. 2, 2009, 4 pages.
Inhalclip, retrieved from the internet Jul. 9, 2018, <URL: https://web.archive.org/web/20120413113017/http://www.oscimedsa.com/Stress_insomnie_stop>, published Oct. 21, 2010, 3 pages.
International Preliminary Examination Report in PCT/AU2003/000504 dated Feb. 2, 2005, 36 pages.
Max-Air Nose Cones, retrieved from the internet Jul. 9, 2018, <URL: https://web.archive.org/web/20120725110753/http://www.maxairnosecones.com/max-air-nose-cones>, published Feb. 13, 2011, 8 pages.
Megavent Nasal Dilator, retrieved from the internet Jul. 9, 2018, <URL: http://www.wellnessproducts.ch/?Ian=en&page=2&id=66999>, published Jun. 26, 2012, 3 pages.
Nasal Pass Dilator, retrieved from the internet Jul. 9, 2018, <URL: https://web.archive.org/web/20120630121946/http://nasalpass.com/contact_us.htm>, published Apr. 21, 2006, 1 pages.
Nasilator, The Science of Better Breating, retrieved from the internet Jul. 17, 2018, <URL: https://web.archive.org/web/20121219024329/http://www.nasilator.com/home.aspx>, published Sep. 6, 2012, 1 pages.
Non-Finai Office Action in U.S. Serial Ng. U.S. Appl. No. 10/631,415 dated Aug. 18, 2005, 15 pages.
Non-Final Office Action in U.S. Appl. No. 10/631,415 dated Dec. 29, 2005, 9 pages.
Non-Final Office Action in U.S. Appl. No. 11/363,884 dated May 14, 2009, 9 pages.
Non-Final Office Action in U.S. Appl. No. 11/363,924 dated Apr. 13, 2009, 9 pages.
Non-Finai Office Action in U.S. Appl. No. 12/154,868 dated Oct. 23, 2014, 35 pages.
Noseglobes, retrieved from the internet Jul. 9, 2018, <URL:https://web.archive.org/web/20110128162352/http://noseglobes.com/>, published Jan. 28, 2011, 1 page.
Nozovent® Anti-Snoring Medical Nasal Dilator Device, retrieved from the internet on Jul. 9, 2018, <URL: https://web.archive.org/web/20120619012956/http://www.snoringcure.ca/nozovent_nasal_anti_snoring_medical_dilator_device.htm>, published Jul. 13, 2007, 2 pages.
Original Breathe Fit Snoring Aid Nasal Dilator, by Breathe Fit Nasal Dilator, retrieved from the internet on Jul. 9, 2018: <URL: https://web.archive.org/web/20120619035547/http://www.amazon.com/Original-Breathe-Fit-Nasal-Dilator/dp/B0012RMWC4>, published Aug. 21, 2009, 5 pages.
Sanispira Dpi, retrieved from the internet Jul. 9, 2018, <URL: https://web.archive.org/web/20120712044423/http://www.sanispira.it/eng/index.php>, published Mar. 4, 2011, 3 pages.
Sinus Cones, retrieved from the internet Jul. 9, 2018, <URL: https://web.archive.org/web/20120206054639/http://www.sanostec.com/code/productinfo.htm>, published Sep. 8, 2004, 2 pages.
SleepRight, retrieved from the internet Jul. 11, 2018, <URL: http://www.sleepright.com/nasal-breathe-aid.php>, published Jun. 17, 2013, 6 pages.

(56) References Cited

OTHER PUBLICATIONS

Snore Free, retrieved from the internet Jul. 9, 2018, <URL: https://web.archive.org/web/20120614222005/http://www.magnetictherapy.co.uk/scp/SPECIALITY_PRODUCTS/SNORE_FREE.html>, published Dec. 8, 2004, 2 pages.

Snore Pin, Sleep Apnea Snoring Treatment, retrieved from the internet Jul. 17, 2018, <URL: https://web.archive.org/web/20130111010828/http://omnisleep.in/snore-pin.html>, published Jan. 11, 2013, 2 pages.

Snoreben, retrieved from the internet Jul. 9, 2018, <URL: http://www.benmedical.com.au/>, published Jan. 2011, 2 pages.

Snoregem, British Snoring & Sleep Apnoea Associate, retrieved from the internet Jul. 9, 2018, <URL: https://web.archive.org/web/20120627060249/http://www.britishsnoring.co.uk/shop/snoregem.php>, published Jul. 3, 2010, 2 pages.

Snore-no-More, retrieved from the internet Jul. 9, 2018, <URL: https://web.archive.org/web/20120626140524/http://www.britishsnoring.co.uk/shop/nasal_dilators/snore_no_more.php?>, published Dec. 12, 2005, 1 pages.

Surgical Nostril Retainers, Porex Surgical Products Group, retrieved from the internet Jul. 17, 2018, <URL: https://web.archive.org/web/20051217233845/https://www.porexsurgical.com/English/surgical/sprodnoseother.asp>, published Dec. 19, 2005, 2 pages.

Ultimate Nasal Dilator, retrieved from the internet Jul. 9, 2018, <URL: https://web.archive.org/web/20120718070024/http://www.nasalaid.com/>, published Oct. 28, 2007, 1 page.

WoodyKnows—Super Nasal Filter for Allergy Relief, retrieved from the internet Jul. 17, 2018, <URL: https://web.archive.org/web/20120818163139/http://www.woodyknows.com:80/>, published Aug. 18, 2012, 3 pages.

Final Office Action in U.S. Appl. No. 15/319,941, dated Mar. 3, 2020, 40 pages.

Non-Final Office Action in U.S. Appl. No. 15/579,304, dated Jan. 24, 2020, 20 pages.

Final Office Action in U.S. Appl. No. 15/579,304, dated Jan. 21, 2021, 13 pages.

Non-Final Office Action in U.S. Appl. No. 15/748,698, dated Mar. 22, 2021, 26 pages.

Final Office Action in U.S. Appl. No. 15/319,940 dated Jan. 7, 2020, 25 pages.

Non-Final Office Action in U.S. Appl. No. 15/319,940 dated Sep. 30, 2020, 24 pages.

Non-Final Office Action in U.S. Appl. No. 15/579,304 dated Aug. 21, 2020, 12 pages.

\* cited by examiner

NASAL DILATOR DEVICES

CROSS REFERENCE TO RELATED APPLICATIONS

This is a National Phase entry of International Application No. PCT/AU2015/050032, filed Jan. 30, 2015, which claims priority to International Application No. PCT/AU2014/000649, filed Jun. 20, 2014, the disclosures of which are incorporated herein by reference in their entireties.

TECHNICAL FIELD

Described embodiments generally relate to nasal dilator devices for facilitating respiration. Some embodiments relate to nasal dilator devices to be fitted to the nose to facilitate or improve respiration during sleeping and/or sporting activities and/or for general day-to-day wear. Some embodiments relate to nasal dilator devices including filtration mechanisms to filter airflow during respiration and other embodiments relate to nasal dilator devices including agent delivery mechanisms for delivery of fragrances and/or medicaments to the nose during respiration.

BACKGROUND

Nasal dilator devices are worn by users to dilate their nasal cavities when sleeping and/or partaking in sporting activities to thereby facilitate respiration. However, many nasal dilator devices are uncomfortable to wear and/or become easily dislodged from a user's nose during such activities.

In particular, activities that are percussive, such as running, cause nasal dilator devices to move from their position as intended by the user requiring readjustment. In the field of professional sports, such adjustments are a physical and mental distraction that can negate any other intended benefit of such devices.

It is desired to address or ameliorate one or more shortcomings of prior nasal dilator devices, or to at least provide a useful alternative thereto.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

Some embodiments relate to a nasal dilator device comprising a substantially U-shaped body including a central portion arranged to span a septum of a nose when worn by a user and first and second leg members extending from the central portion in a first plane, a first cantilever rib member extending outward from the U-shaped body in a second plane, a second cantilever rib member extending outward from the U-shaped body in a third plane, wherein the first and second cantilever rib members extend away from each other, a first intermediate section connecting an end of the first leg member to a proximal end of the first cantilever rib member, wherein the first intermediate section extends from the first plane to the second plane and a second intermediate section connecting an end of the second leg member to a proximal end of the second cantilever rib member, wherein the second intermediate section extends from the first plane to the third plane, and at least one projection protruding from and extending along at least a portion of a length of each of the first and second cantilever rib members.

In some embodiments, the at least one projection may comprise first and second projections, each forming a flange disposed at respective elongate edges of a major surface of the nasal dilator device. The at least one projection may be arranged, in use, to engage with an inner surface of a nose.

In some embodiments, the second and third planes may be orthogonal or perpendicular to the first plane. The first intermediate section and the second intermediate section may be right angled sections. The first and second intermediate sections may be arranged, in use, to engage with the septum and extend from the septum behind the columella and alar fibrofatty tissue of the nose, allowing the first and second cantilever rib members, in use, to extend along respective nasal orifices to an inner wall of the nostrils.

The first and second cantilever rib members may be arcuate cantilever rib members, each having a curvature along its length. The first and second intermediate sections may be arcuate intermediate sections, each having a curvature along its length. The second and third planes may be converging planes such that the first and second cantilever rib members are angled and/or extend substantially toward the central portion of the U-shaped body. The second and third planes may be diverging planes such that the first and second cantilever rib members are angled and/or extend substantially toward the central portion of the U-shaped body. The second and third planes may be the same plane.

In some embodiments, the first and second cantilever rib members may exhibit an elongate arched profile which approximates at least a portion of one of a circle, ellipse or parabola. The first and second leg members may be inclined towards each other such that a relatively greater distance is provided between the first and second leg members towards the central portion accommodate a columella of a nose when donned by the user. The first and second intermediate sections may be inclined away from each other to assist in urging the respective first and second cantilever rib members against inner walls of respective nostrils when worn by the user.

In some embodiments, the first and second cantilever rib members may comprise respective first and second nostril engaging elements for engaging with an inner wall of a respective nostril. The first and second nostril engaging elements may extend arcuately from the respective first and second distal ends of the respective first and second rib members. For example, the first and second nostril engaging elements may extend from the first and second planes respectively and in a direction away from the central portion of the U-shaped body. The first and second nostril engaging elements may be disposed at distal ends of the first and second cantilever rib members, respectively.

In some embodiments, a series of protrusions may be disposed on the first and second nostril engaging elements. For example, the first and second nostril engaging elements may be substantially elongate and the series of protrusions may extend along a length of the first and second nostril engaging elements. The series of protrusions may comprise a plurality of elongated v-shaped protrusions.

In some embodiments, enlarged pads may be disposed on the first and second nostril engaging elements to engage with inner walls of the nostrils. For example, the enlarged pads may comprise the series of protrusions and/or the series of protrusions may be formed from an overmould material. In some embodiments, the at least one projection may be integrated with and extend from a corresponding protrusion of the series of protrusions. The at least one projection may be formed from an overmould material.

In some embodiments, the nasal dilator may comprise a first and second releasable attachment mechanism for releasably attaching the first and second cantilever rib members, for example, distal ends of the first and second cantilever rib members, to the U-shaped body and/or the first and second intermediate section respectively. For example, the releasable attachment mechanisms may be arranged to releasably attach first and second nostril engaging elements disposed at distal ends of the first and second cantilever rib members to the first and second leg members, respectively. The releasable attachment mechanisms may be arranged to releasably attach the first and second nostril engaging elements disposed at distal ends of the first and second cantilever rib members to the first and second intermediate sections, respectively.

The releasable attachment mechanisms may each comprise an arm and a socket arranged to receive and engage the arm. A stopper or hook may be disposed at an end of the arm to hinder the arm from withdrawing from the socket. A notch may be disposed on an inner surface of the socket and may be configured to engage with the stopper or hook on the arm to hinder the arm from withdrawing from the socket.

In some embodiments, the arms may be disposed on an inner surface of first and second nostril engaging elements of the first and second cantilever rib members, respectively, and the sockets may be disposed on the first and second leg members. In some embodiments, the arms may be disposed on an inner surface of first and second nostril engaging elements of the first and second cantilever rib members, respectively, and the sockets may be disposed on the first and second intermediate sections. In some embodiments, the sockets may be disposed on an inner surface of first and second nostril engaging elements of the first and second cantilever rib members, respectively, and the arms may be disposed on the first and second leg members. In some embodiments, the sockets may be disposed on an inner surface of first and second nostril engaging elements of the first and second cantilever rib members, respectively, and the arms may be disposed on the first and second intermediate sections. In some embodiments, the nasal dilator device may comprise first and second arm support members projecting from respective first and second intermediate sections, the sockets may be disposed on an inner surface of first and second nostril engaging elements of the first and second cantilever rib members, respectively, and the arms may be disposed on the first and second arm support members.

The sockets may comprise substantially elongate housings which taper along their length and provide a relatively broad opening for receiving the arms. Each of the sockets may be provided with apertures in side walls of the housing.

Some embodiments relate to a nasal dilator device comprising a substantially U-shaped body including a central portion arranged to span a septum of a nose when worn by a user and first and second leg members extending from the central portion in a first plane, a first cantilever rib member extending outward from the U-shaped body in a second plane, a second cantilever rib member extending outward from the U-shaped body in a third plane, wherein the first and second cantilever rib members extend away from each other, a first intermediate section connecting an end of the first leg member to a proximal end of the first cantilever rib member, wherein the first intermediate section extends from the first plane to the second plane, a second intermediate section connecting an end of the second leg member to a proximal end of the second cantilever rib member, wherein the second intermediate section extends from the first plane to the third plane, a first releasable attachment mechanism for releasably attaching a distal end of the first cantilever rib member to the first intermediate section and a second releasable attachment mechanism for releasably attaching a distal end of the second cantilever rib member to the second intermediate section.

The second and third planes may be orthogonal or perpendicular to the first plane. The first intermediate section and the second intermediate section are right angled sections. The first and second cantilever rib members may comprise respective first and second nostril engaging elements for engaging with an inner wall of a respective nostril.

In some embodiments, the releasable attachment mechanisms may be arranged to releasably attach first and second nostril engaging elements disposed at the distal ends of the first and second cantilever rib members to the first and second leg members, respectively. The releasable attachment mechanisms may each comprise an arm and a socket arranged to receive and engage the arm. A stopper or hook may be disposed at an end of the arm to hinder the arm from withdrawing from the socket. A notch may be disposed on an inner surface of the socket and may be configured to engage with the stopper or hook on the arm to hinder the arm from withdrawing from the socket.

In some embodiments, the arms may be disposed on an inner surface of first and second nostril engaging elements of the first and second cantilever rib members, respectively, and the sockets may be disposed on the first and second intermediate sections. In some embodiments, the sockets may be disposed on an inner surface of first and second nostril engaging elements of the first and second cantilever rib members, respectively, and the arms may be disposed on the first and second intermediate sections. In some embodiments, the nasal dilator device may further comprise first and second arm support members projecting from respective first and second intermediate sections and the arms may be disposed on the first and second arm support members.

In some embodiments, the sockets may comprise substantially elongate housings which taper along their length and provide a relatively broad opening for receiving the arms. Each of the sockets may be provided with apertures in side walls of the housing.

Some embodiments relate to a nasal dilator device comprising a substantially U-shaped body including a central portion arranged to span a septum of a nose when worn by a user and first and second leg members extending from the central portion in a first plane, a first cantilever rib member extending outward from the U-shaped body in a second plane, a second cantilever rib member extending outward from the U-shaped body in a third plane, wherein the first and second cantilever rib members extend away from each other, a first intermediate section connecting an end of the first leg member to a proximal end of the first cantilever rib member and a second intermediate section connecting an end of the second leg member to a proximal end of the second cantilever rib member.

In some embodiments, the first intermediate section may extend from the first plane to the second plane and the second intermediate section may extend from the first plane to the third plane. The second and third planes may be orthogonal to the first plane.

For example, the first intermediate section and the second intermediate section may be right angled sections. In some embodiments, the first and second intermediate sections are arranged, in use, to engage with the septum and extend from the septum behind the columella and alar fibrofatty tissue of the nose allowing the first and second cantilever rib members, in use, to extend along respective nasal orifices to an inner wall of the nostrils.

In some embodiments, the first intermediate section may extend between the first plane and the second plane and the second intermediate section may extend between the first plane and the third plane. For example, the first and second intermediate sections may be arranged, in use, to extend along a length of the septum and the first and second cantilever rib members are each arranged, in use, to extend from a floor of a respective nasal orifice to an inner wall of the nostrils.

Some embodiments relate to a nasal dilator device comprising a substantially U-shaped body including a central portion arranged to span a septum of a nose when worn by a user and first and second leg members extending from the central portion in a first plane, a first cantilever rib member extending outward from an end of the first leg member of the U-shaped body in a second plane, a second cantilever rib member extending outward from an end of the second leg member of the U-shaped body in a third plane, wherein the first and second cantilever rib members extend away from each other and at least one projection protruding from and extending along at least a portion of a length of each of the first and second cantilever rib members. For example, the second and third planes may be orthogonal to the first plane.

Some embodiments relate to a nasal dilator device comprising a substantially U-shaped body including a central portion arranged to span a septum of a nose when worn by a user and first and second leg members extending from the central portion, first and second cantilever rib members extending outward from the U-shaped body and away from one another, a first intermediate section connecting an end of the first leg member to a proximal end of the first cantilever rib member and a second intermediate section connecting an end of the second leg member to a proximal end of the second cantilever rib member, wherein the first and second leg members are arranged, in use, to extend inward of respective nasal orifices along the septum, the first and second intermediate sections are arranged, in use, to engage with the septum and extend from the septum behind the columella and alar fibrofatty tissue of the nose allowing the first and second cantilever rib members, in use, to extend along the respective nasal orifices to an inner wall of the nostrils.

Some embodiments relate to a nasal dilator device comprising a substantially U-shaped body including a central portion arranged to span a septum of a nose when worn by a user and first and second leg members extending from the central portion in a first plane a first cantilever rib member extending outward from the U-shaped body in a second plane a second cantilever rib member extending outward from the U-shaped body in a third plane wherein the first and second cantilever rib members extend away from each other a first intermediate section connecting an end of the first leg member to a proximal end of the first cantilever rib member, wherein the first intermediate section extends between the first plane and second plane and a second intermediate section connecting an end of the second leg member to a proximal end of the second cantilever rib member, wherein the second intermediate section extends between the first plane and the third plane.

In some embodiments, the first and second cantilever rib members may be arcuate cantilever rib members, each having a curvature along its length. In some embodiments, the first and second intermediate sections are arcuate intermediate sections, each having a curvature along its length.

The first and second intermediate sections may be arranged, in use, to extend along a length of the septum and the first and second cantilever rib members may be each arranged, in use, to extend from a floor of a respective nasal orifice to an inner wall of the nostrils.

In some embodiments, the first and second intermediate portions may extend obtusely from the ends of the first and second leg members. The second and third planes may be converging planes. In some embodiments, the first and second cantilever rib members may exhibit an elongate arched profile which approximates at least a portion of one of a circle, ellipse or parabola.

In some embodiments, the first and second leg members may be inclined towards each other such that a relatively greater distance is provided between the first and second leg members towards the central portion to accommodate a columella of a nose when donned by the user. In some embodiments, the first and second intermediate sections may be inclined away from each other to assist in urging the respective first and second cantilever rib members against inner walls of respective nostrils when worn by the user.

The first and second cantilever rib members may comprise respective first and second nostril engaging elements for engaging with an inner wall of a respective nostril. The first and second nostril engaging elements may be disposed at distal ends of the first and second cantilever rib members, respectively. A series of protrusions is disposed on the first and second nostril engaging elements. The first and second nostril engaging elements may be substantially elongate and the series of protrusions may extend along a length of the first and second nostril engaging elements. For example, the series of protrusions comprises a plurality of an elongated v-shaped protrusions. Enlarged pads may be disposed on the first and second nostril engaging elements to engage with inner walls of the nostrils. The enlarged pads may comprise the series of protrusions. The series of protrusions are formed from an overmould material.

In some embodiments, the nasal dilator device may comprise at least one projection protruding from and extending along at least a portion of a length of the first and second cantilever rib members. The nasal dilator device may comprise first and second projections, each forming a flange disposed at respective elongate edges of a major surface of the nasal dilator device and extending along at least a portion of a length of the first and second cantilever rib members. The nasal dilator device may comprise at least one projection protruding from and extending along at least a portion of a length of the first and second cantilever rib members, wherein the at least one projection is integrated with and extends from a corresponding protrusion of the series of protrusions. The at least one projection may be formed from an overmould material.

In some embodiments, the nasal dilator device may further comprise a first and second releasable attachment mechanism for releasably attaching the first and second cantilever rib members, respectively, to the U-shaped body. For example, the releasable attachment mechanisms may be arranged to releasably attach the first and second nostril engaging elements to the first and second leg members, respectively. In some embodiments, the releasable attachment mechanisms may be arranged to releasably attach the first and second nostril engaging elements to the first and second intermediate sections, respectively.

The releasable attachment mechanisms may each comprise an arm and a socket arranged to receive and engage the arm. A stopper or hook may be disposed at an end of the arm to hinder the arm from withdrawing from the socket. A notch may be disposed on an inner surface of the socket and is configured to engage with the stopper or hook on the arm to hinder the arm from withdrawing from the socket.

In one embodiment, the arms may be disposed on an inner surface of first and second nostril engaging elements of the first and second cantilever rib members, respectively, and the sockets may be disposed on the first and second leg members. In another embodiment, the arms may be disposed on an inner surface of first and second nostril engaging elements of the first and second cantilever rib members, respectively, and the sockets may be disposed on the first and second intermediate sections. In another embodiment, the sockets may be disposed on an inner surface of first and second nostril engaging elements of the first and second cantilever rib members, respectively, and the arms may be disposed on the first and second leg members. In another embodiment, the sockets may be disposed on an inner surface of first and second nostril engaging elements of the first and second cantilever rib members, respectively, and the arms may be disposed on the first and second intermediate sections. In another embodiment, the nasal dilator device may comprise first and second arm support members projecting from respective first and second intermediate sections and the sockets may be disposed on an inner surface of first and second nostril engaging elements of the first and second cantilever rib members, respectively, and the arms may be disposed on the first and second arm support members.

In some embodiments, the sockets may comprise substantially elongate housings which taper along their length and provide a relatively broad opening for receiving the arms. The socket may be provided with apertures in side walls of the housing.

In some embodiments, a capsule may be provided within the socket and may be arranged to be activated by the arm when the arm is received by the socket. The capsule may include at least one of a medicament or compound. The arm may comprise a coating disposed thereon arranged to release a scent in response to abrasion of the coating. An aperture may be disposed in each of the first and second nostril engaging elements. The aperture may be arranged to receive at least one of a compound, a medicament, and a capsule comprising a medicament or compound emanating a scent.

Some embodiments relate to a nasal dilator device a nasal dilator device comprising a substantially U-shaped body including a central portion arranged to span a septum of a nose when worn by a user and first and second leg members extending from the central portion in a first plane, a first closed loop structure extending outward from a longitudinal axis of the U-shaped body in a second plane and defining a first aperture; a second closed loop structure extending outward from a longitudinal axis of the U-shaped body in a third plane and defining a second aperture, wherein the first and second closed loop structures extend away from each other, a first intermediate section connecting an end of the first leg member to a proximal end of the first loop structure, wherein the first intermediate section extends between the first plane and second plane, and a second intermediate section connecting an end of the second leg member to a proximal end of the second loop structure, wherein the second intermediate section extends between the first plane and the third plane.

In some embodiments, the first loop structure may comprise a first flange portion and the second loop structure may comprise a second flange portion, wherein the first and second flange portions are arranged to form a seal with the walls nasal passage in use. For example, the first and second flange portions may project from an outer surface of the first and second loop structures, respectively, and extend along at least a portion of a circumference of the first and second loop structures, respectively.

In some embodiments, the first loop structure may comprise two or more flange portions and the second loop structure may comprise two or more flange portion, wherein the flange portions are arranged to restrict dislodgement of the nasal dilator from a nose in use.

In some embodiments, the first and second loop structures may each comprise a filter spanning the first and second apertures defined by the first and second loop structures. The filters may be arranged to snap fit into the first and second loop structures. The filters may be welded to the first and second loop structures.

In some embodiments, the first and second intermediate sections are arcuate intermediate sections, each having a curvature along its length. The first and second intermediate portions may extend obtusely from the ends of the first and second leg members.

The first and second intermediate sections may be arranged, in use, to extend along a length of the septum and the first and second loop structures may be each arranged, in use, to extend from a floor of a respective nasal orifice along an inner wall of the nostrils such that the first and second apertures are aligned with a nasal passage of the nose.

In some embodiments, the second and third planes may be converging planes.

The first and second leg members may be inclined towards each other such that a relatively greater distance is provided between the first and second leg members towards the central portion to accommodate a columella of a nose when donned by the user. The first and second intermediate sections may be inclined away from each other to assist in urging the respective first and second loop structures against inner walls of respective nostrils when worn by the user.

In some embodiments, the nasal dilator device may further comprise a film disposed on a surface of the nasal dilator and a removable seal provided on the film to mitigate release of a compound from the film.

In some embodiments, the nasal dilator device may further comprise an overmould disposed on at least one of the central portion, the leg members, the intermediate sections and the arcuate cantilever rib members. The overmould may be infused with a compound, a medicament, a fragrance or an aroma. The nasal dilator device may be composed of a substrate material infused with a medicament, a fragrance or an aromatic agent.

In some embodiments, the central portion comprises a tab extending in a direction substantially opposite to the first and second leg members to assist with insertion, removal and/or placement of the nasal dilator device. The tab may be removeable from the nasal dilator device.

Some embodiments relate to a nasal dilator device comprising a substantially U-shaped body including: a central portion arranged to span a septum of a nose when worn by a user, and first and second leg members extending from the central portion, first and second cantilever rib members extending outward from a longitudinal axis of the U-shaped body and away from one another, a first intermediate section connecting an end of the first leg member to a proximal end of the first cantilever rib member, and a second intermediate section connecting an end of the second leg member to a proximal end of the second cantilever rib member, wherein the first and second leg members are arranged, in use, to extend inward of respective nasal orifices along the septum, the first and second intermediate sections are arranged, in use, to extend along a length of the septum behind the columella and alar fibrofatty tissue of the nose and the first and second cantilever rib members are each arranged, in use, to extend from a floor of the respective nasal orifices to an inner wall of the nostrils.

BRIEF DESCRIPTION OF DRAWINGS

Embodiments are described in further detail below, by way of example, with reference to the accompanying drawings, in which.

DESCRIPTION OF EMBODIMENTS

Figure 1A:
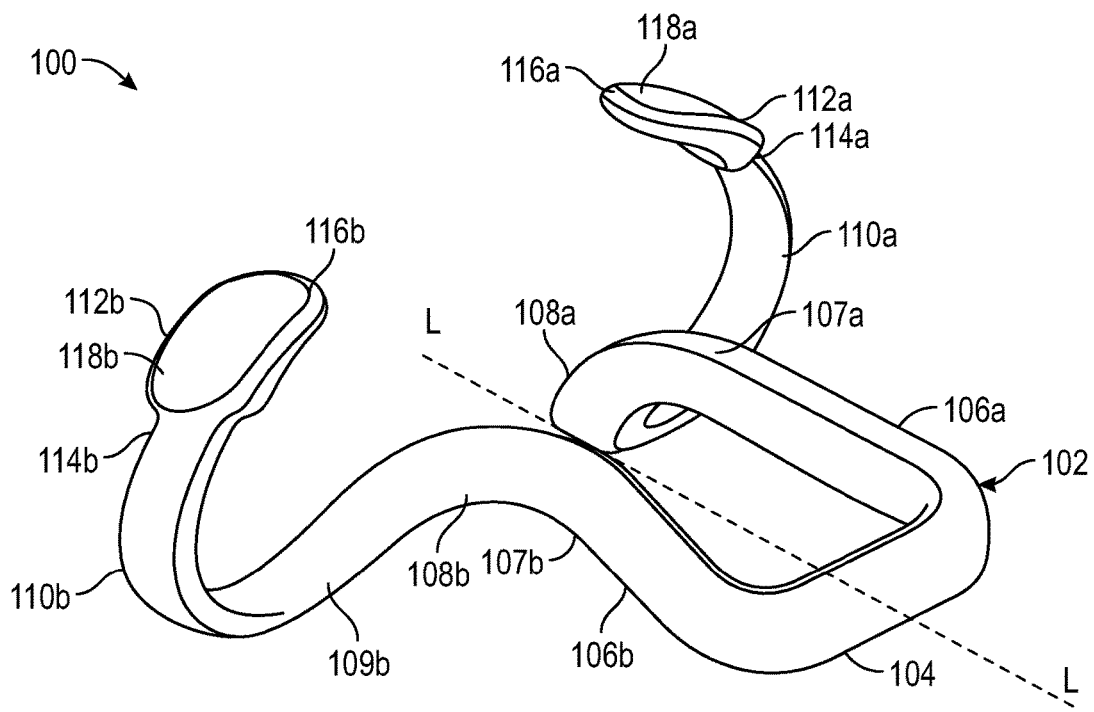
FIG. 1A is front perspective view of a nasal dilator device according to some embodiments.

Described embodiments generally relate to nasal dilator devices for facilitating respiration. Some embodiments relate to nasal dilator devices to be fitted to the nose to facilitate or improve respiration during sleeping and/or sporting activities and/or for general day-to-day wear. Some embodiments relate to nasal dilator devices including filtration mechanisms to filter airflow during respiration and other embodiments relate to nasal dilator devices including agent delivery mechanisms for delivery of fragrances and/or medicaments to the nose during respiration.

Referring to FIG. 1A to 1E, there is illustrated a nasal dilator device, generally indicated at 100 and substantially symmetrical about a longitudinal axis L, according to some embodiments. The nasal dilator device 100 comprises a generally U-shaped body 102 having a central portion 104 and first and second leg members, 106a and 106b, respectively, extending from the central portion 104 in a first plane P1.

The nasal dilator device comprises a first intermediate section 108a extending from an end 107a of the first leg member 106a and a second intermediate section 108b extending from an end 107b of the second leg member 106b. In some embodiments, and as depicted in FIGS. 1A to 1E, the first and second intermediate portions 108a, 108b, may be curved or arcuate along their length. In other embodiments, the first and second intermediate portions 108a, 108b may be substantially straight along their length or may comprise a plurality of angled or arcuate portions. The first and second intermediate portions 108a, 108b may extend obtusely from the first plane P1. For example, the first and second intermediate portions 108a, 108b may extend obtusely from the first and second ends 107a, 107b, for example, substantially at an angle of between approximately 95° and 130° to the longitudinal axis. For example, the first and intermediate sections 108a, 108b may deviate by approximately 100° from the longitudinal axis.

Referring again to FIGS. 1A to 1E, the nasal dilator device 100 comprises a first rib member 110a projecting from the first intermediate section 108a in a second plane P2 and a second rib member 110b projecting from the second intermediate section 108b in a third plane P3. In some embodiments, the first and second rib members 110a, 110b may project substantially outward or laterally of the longitudinal axis of the U-shaped body 102. For example, the first and second rib members 110a, 110b may be cantilever rib members that extend from the first and second intermediate sections 108a, 108b, respectively outwardly from the longitudinal axis and away from one another in a substantially cantilever manner. In some embodiments, the first and second rib members 110a, 110b may be arcuate rib members 110a, 110b or arcuate cantilever rib members 110a, 110b.

In some embodiments, the first and second rib members 110a, 110b may exhibit an elongate arched or bow-like profile which may approximate at least a portion of a circle, ellipse or parabola. For example, the first and second rib members 110a, 110b may extend arcuately along the second and third planes, P2 and P3, respectively in a direction substantially toward the first plane P1.

Figure 1B:
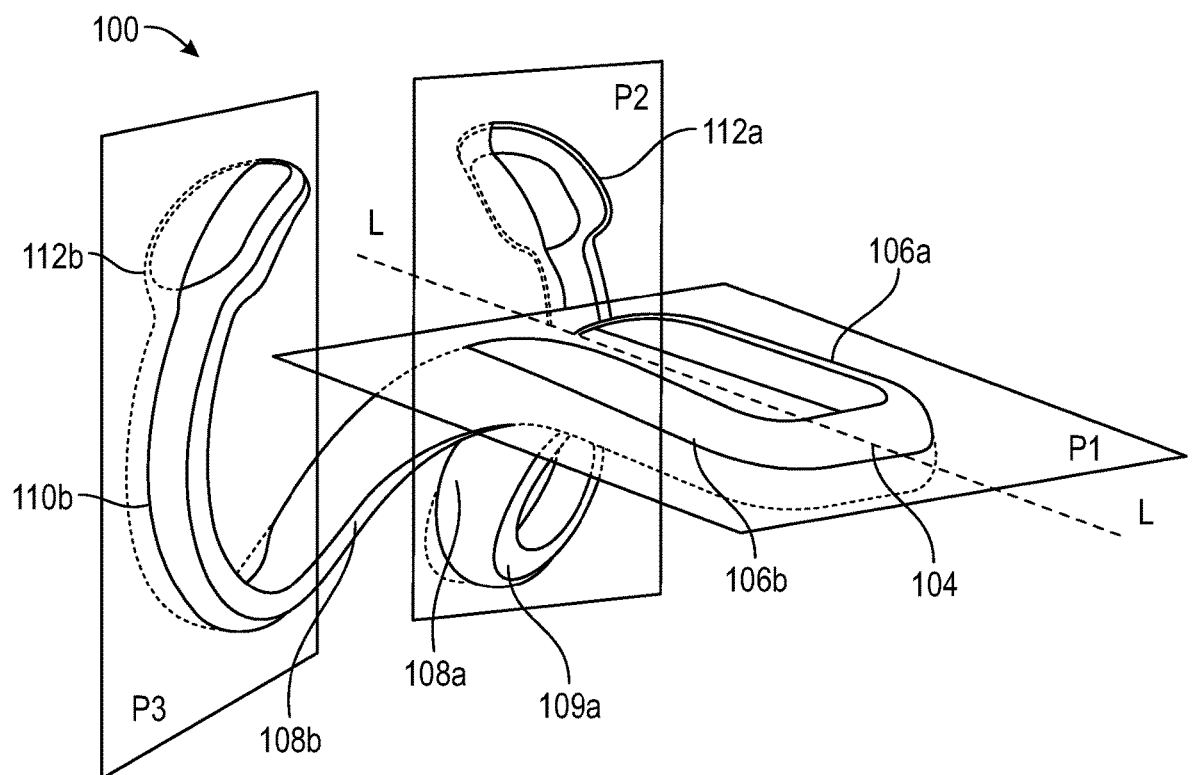
FIG. 1B is a further front perspective view of the nasal dilator device of FIG. 1A.
Figure 1C:
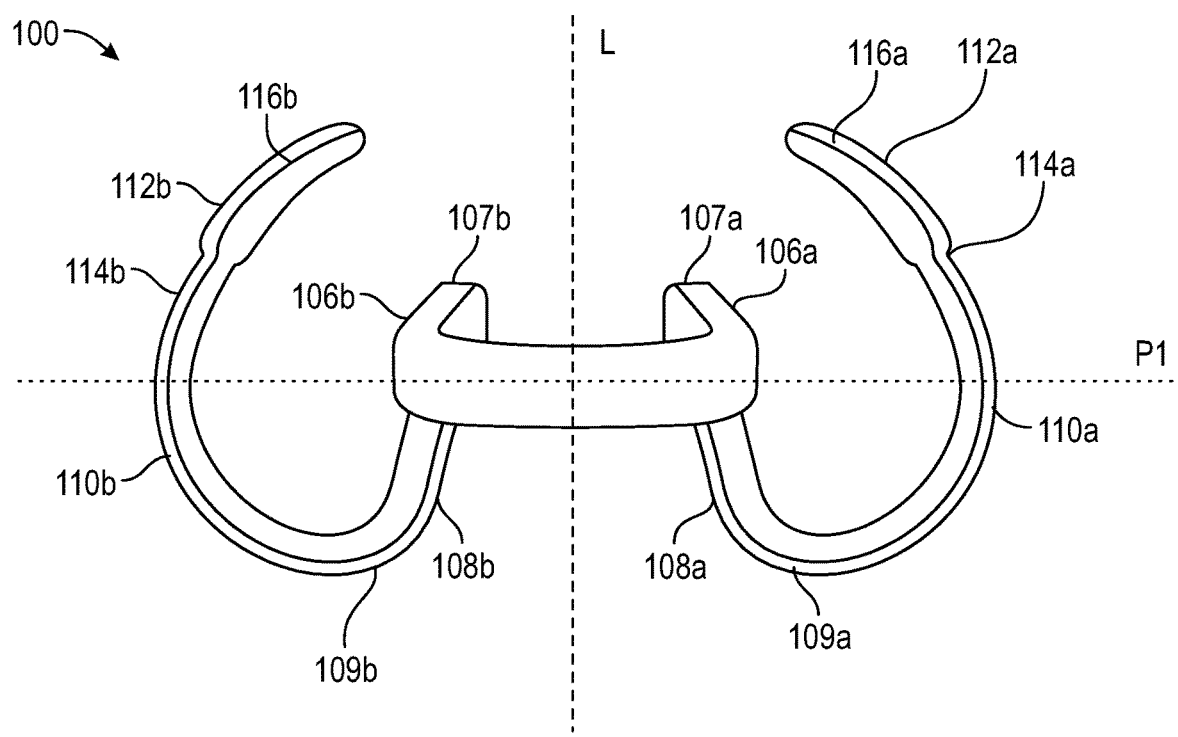
FIG. 1C is a front view of the nasal dilator device of FIG. 1A.
Figure 1D:
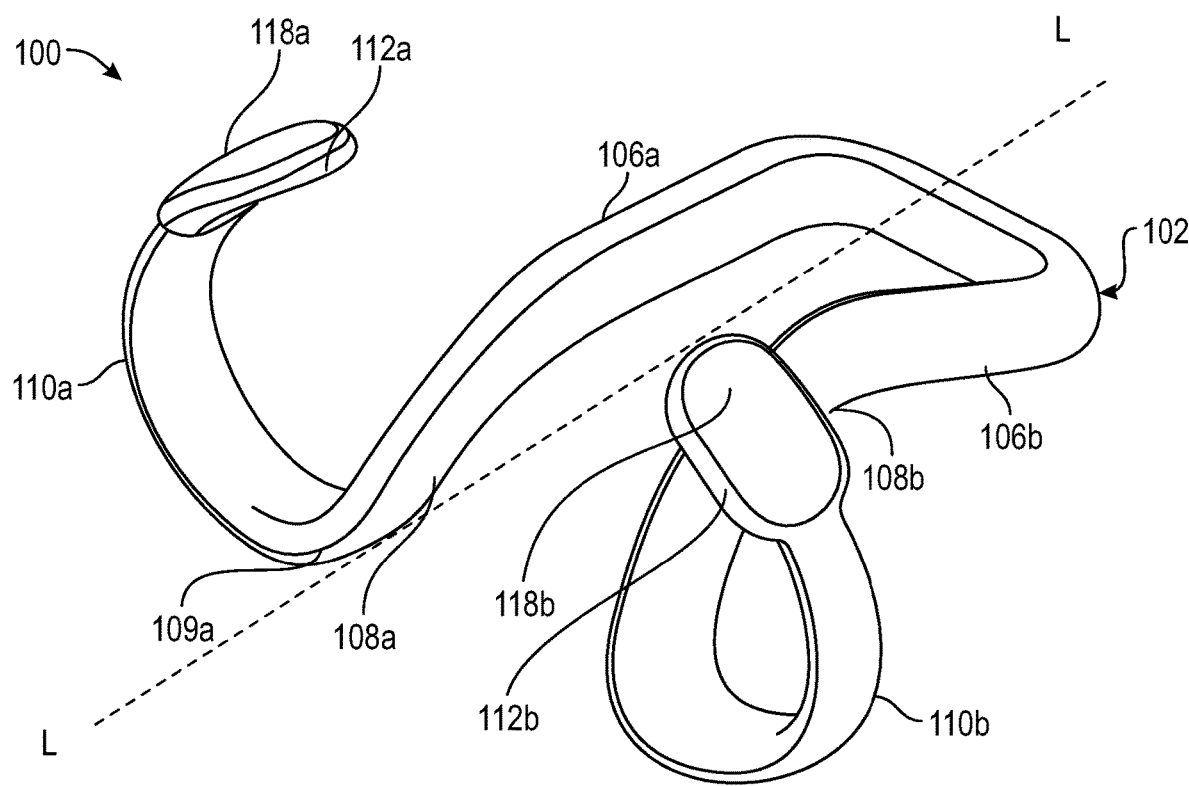
FIG. 1D is a rear perspective view of the nasal dilator device of FIG. 1A.
Figure 1E:
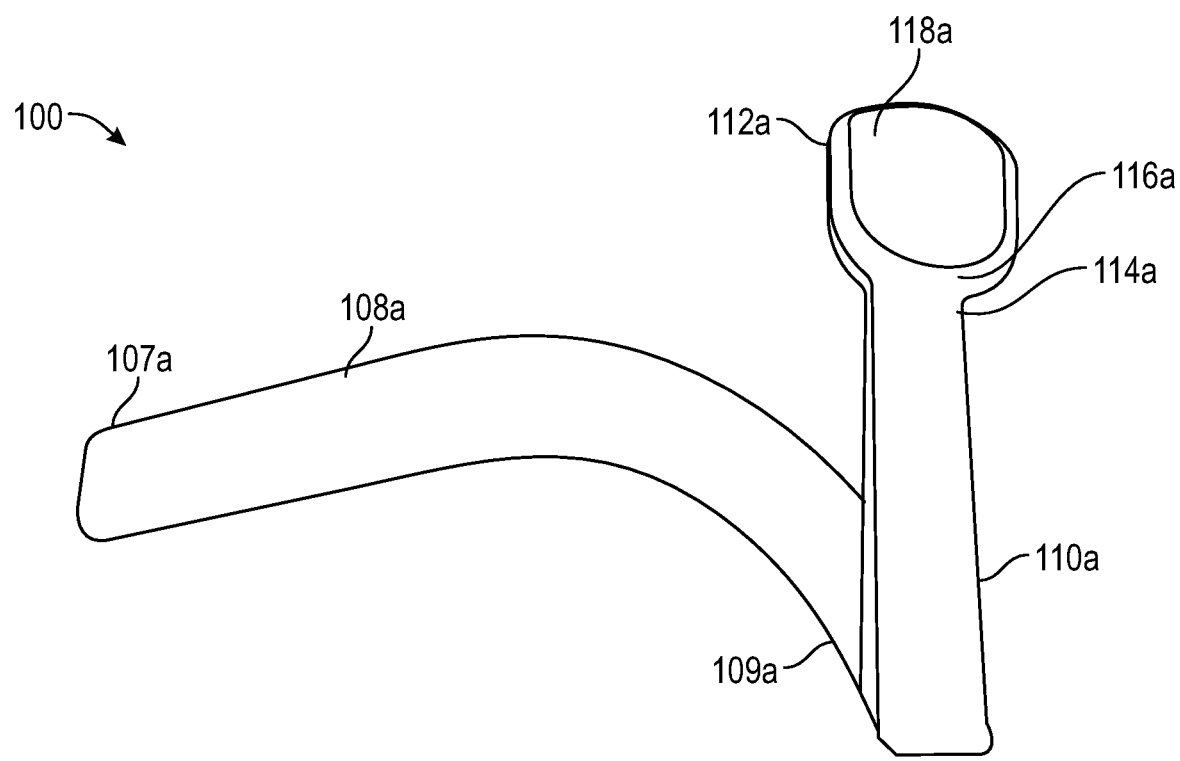
FIG. 1E is a partial side view of the nasal dilator device of FIG. 1A.

The first and second rib members 110a, 110b may be flexible and resiliently biased away from the first and second intermediate sections 108a, 108b, respectively, to allow the first and second rib members 110a, 110b to be compressed for insertion into the nose of a user and to reform once placed inside the nose to thereby dilate the nostrils as discussed in more detail below with reference to FIGS. 3A and 3B. As best depicted in FIGS. 1A and 1B, the first intermediate section 108a may extend or transition between the first plane P1 and the second plane P2 to interconnect the end 107a of the first leg member 106a to a proximal end 109a of the first rib member 110a and the second intermediate section 108b may extend or transition between the first plane and the third plane to interconnect the end 107b of the second leg member 106b to a proximal end 109b of the second rib member 110b.

In some embodiments, the configuration of the first and second intermediate sections 108a, 108b may be associated with an orientation or location of the first and second rib members 110a, 110b with respect to the U-shaped body 104. For example, the configuration of the first and second intermediate sections 108a, 108b may dictate or define an angle between the first plane P1 and the second plane P2 and between the first plane P1 and the third plane P3, respectively. The second and third planes, P2 and P3, may each form an acute angle, a right angle, or substantially right angle or an obtuse angle with the first plane P1. For example, the second and third planes P2 and P3, may be converging planes and may each form an obtuse angle of approximately 95° to 130° with the first plane P1 such that the first and second intermediate sections 108a 108b take the form of obtuse arcuate sections. In some embodiments, the first, second and third planes, P1, P2, P3 may be different from each other and in some embodiments, the second and third planes, P2, P3 may be the same plane and may be different to the first plane P1.

The first and second intermediate sections 108a, 108b may be inclined away from or diverge from one another to assist in urging the respective first and second rib members 110a, 110b against inner walls of respective nostrils when worn by the user.

As depicted in FIGS. 1A to 1E, the first and second rib members 110a, 110b, of the nasal dilator device 100 may comprise respective first and second nostril engaging elements, 112a and 112b, disposed at distal ends 114a, 114b, of the first and second arcuate rib members 110a, 110b, respectively, for engaging with inner walls of respective nostrils when worn by a user. In some embodiments, the first and second nostril engaging elements, 112a, 112b may comprise relatively large surface areas 116a, 116b with respect to the first and second arcuate rib members 110a, 110b.

In some embodiments, the first and second nostril engaging elements 112a, 112b may have pads 118a, 118b, disposed thereon, to engage with the inner walls of the nostrils. For example, the pads 118a, 118b may be disposed on the relatively large major surface areas 116a, 116b of the nostril engaging elements, 112a and 112b and may be enlarged with respect to the first and second arcuate rib members 110a, 110b, and/or the nostril engaging elements, 112a and 112b.

Figure 2:
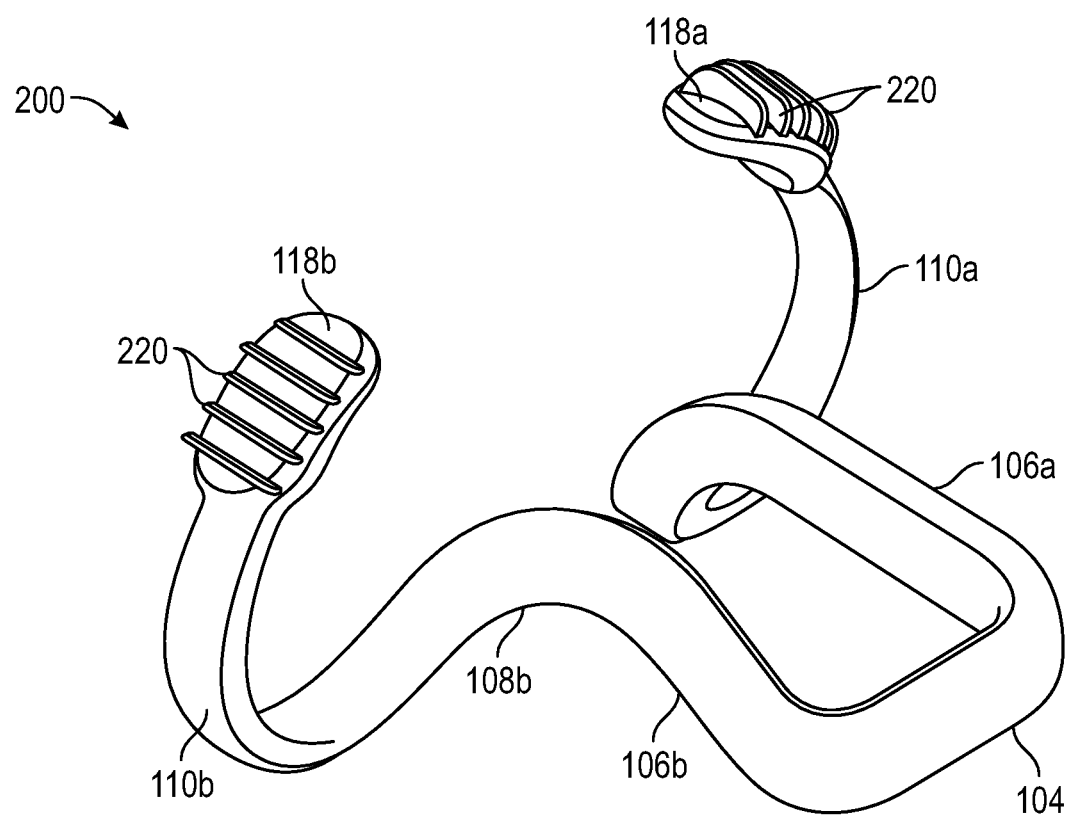
FIG. 2 is a front perspective view of a nasal dilator device including fin-like structures disposed thereon, according to some embodiments.

Referring now to FIG. 2, there is illustrated a nasal dilator device, generally indicated at 200, according to some embodiments. The nasal dilator device 200 may comprise similar components and elements to those of nasal dilator device 100 depicted in FIGS. 1A to 1E and accordingly those similar components and elements are denoted like numerals.

In some embodiments, as depicted in FIG. 2, the pads 118a, 118b of the nasal dilator device 200 may be composed of a relatively soft overmould material, for example a polymer material such as thermoplastic elastomer (TPE) and/or may be provided with a series of protrusions, fins or fin-like structures 220 to provide a comfortable and/or grippable surface for engaging with the inner walls of the nostrils. In some embodiments, such an overmould material may be provided on at least a portion of the rib members 110a, 110, and/or on at least a portion of the intermediate sections 108a, 108b.

The nasal dilator device 100, 200 may be configured to be orientated in a manner such that the first and second nostril engaging elements 112a, 112b may be positioned at a junction of the greater alar cartilage and lateral nasal cartilage, providing improved support for dilation of the nasal passage 308, as discussed in more detail with reference to FIGS. 3A and 3B below.

Figure 3A:
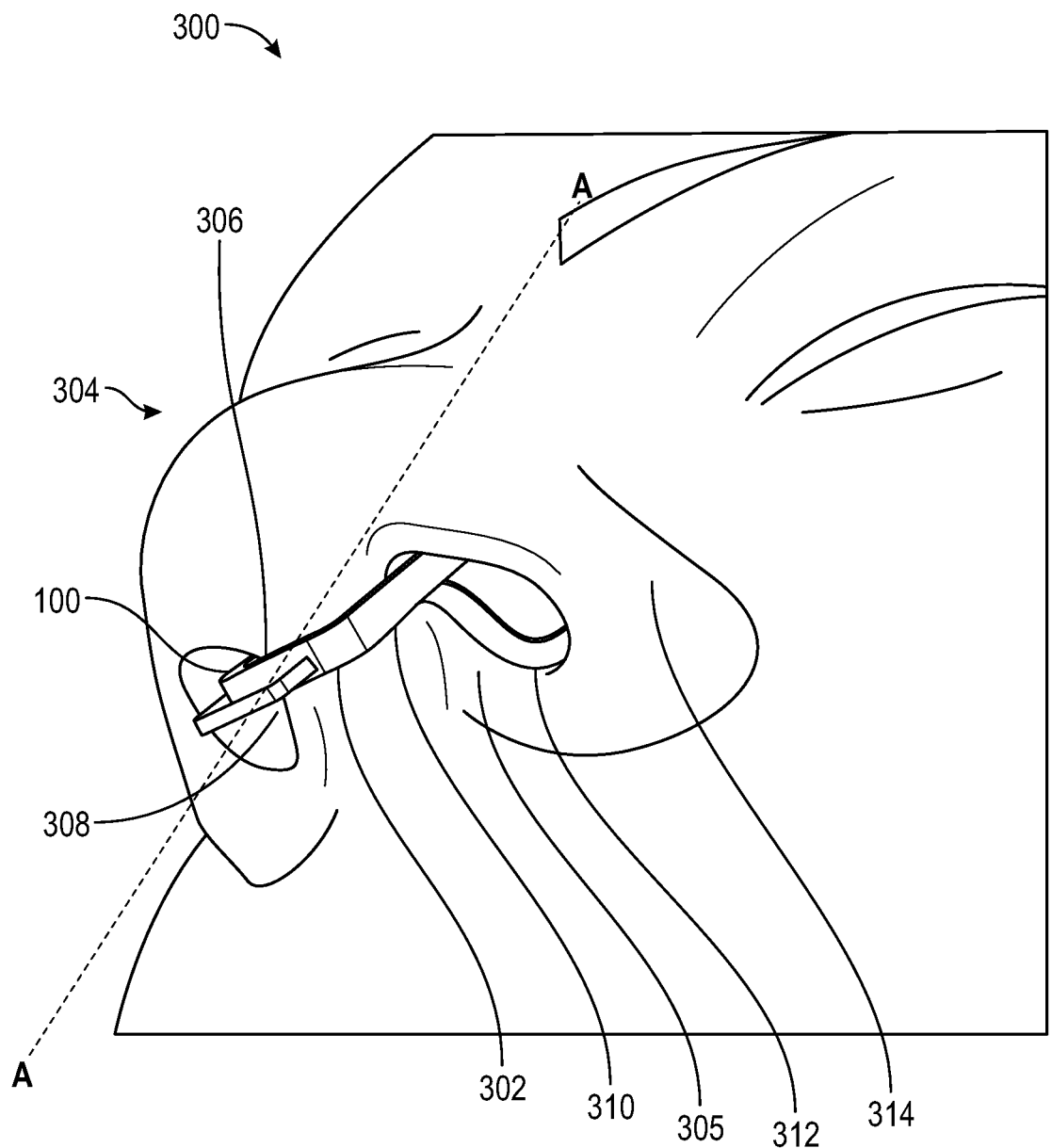
FIG. 3A is a perspective view of a user donning the nasal dilator device of FIGS. 1A to 1E.
Figure 3B:
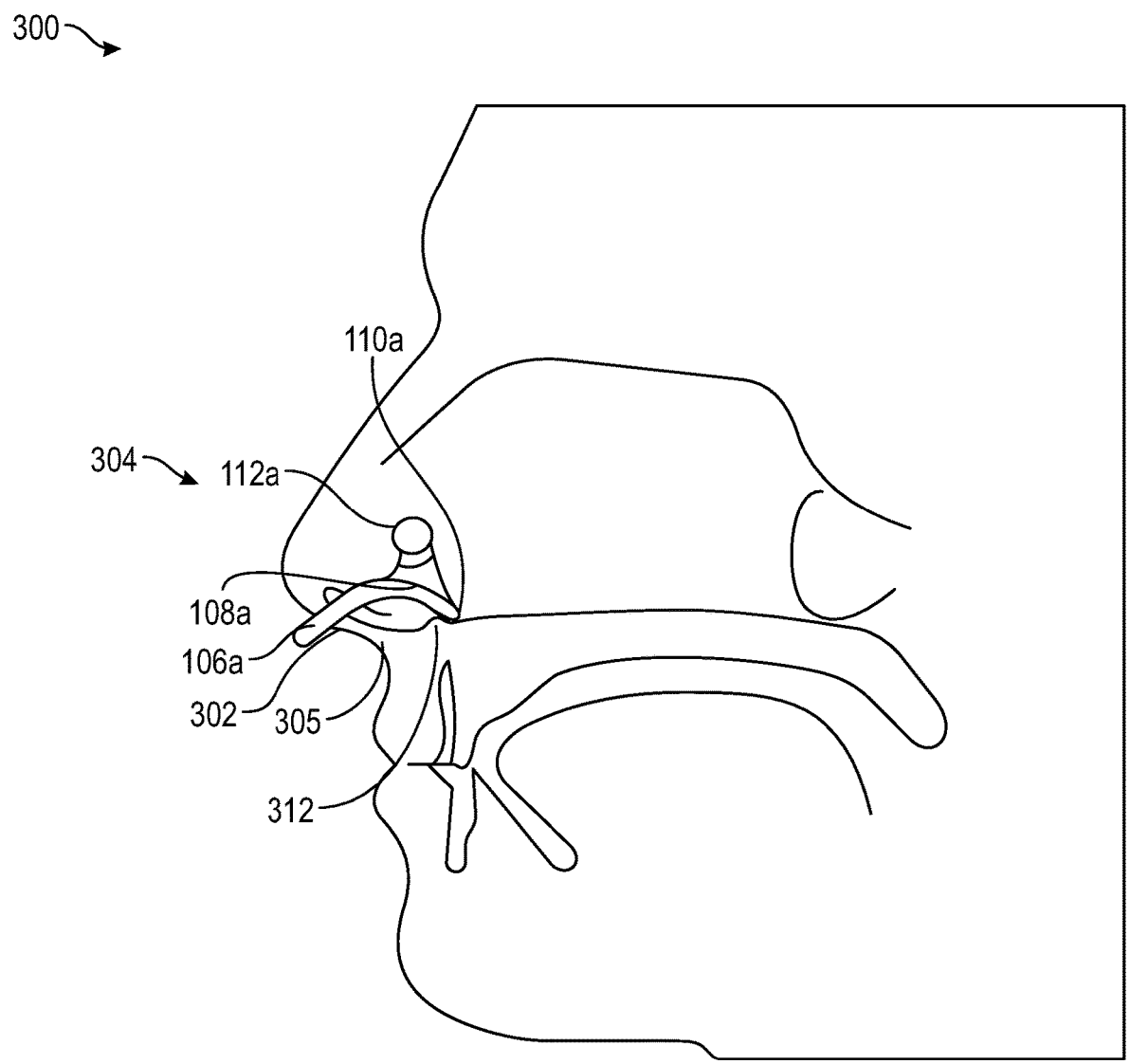
FIG. 3B is a side view of the user of FIG. 3A.

FIG. 3A is a perspective view of a user, generally indicated at 300, wearing or donning the nasal dilator device 100 of FIG. 1A and FIG. 3B is a cross sectional view taken along a midline A-A of the nose of the user of FIG. 3A.

As depicted in FIGS. 3A and 3B, the nasal dilator device 100 is configured to be orientated such that the central portion 104 spans a septum 302, and in particular, a columella 310 (the terminal section or fleshy external end of the septum) of a nose 304 and is positioned toward a tip 306 of the nose 304 and the first and second leg members 106a, 106b extend inward, along a nasal passage 308. For example, the first and second leg members 106a, 106b, may extend inward at an angle of approximately 30 to 40 degrees to a midline A-A of the nose 304. The first and second intermediate sections 108a, 108b may extend along a length of the septum 302 behind the columella 310 and the fibrofatty tissue 305 or bulbous region around the base of the nostrils 314 and the first and second rib members 110a, 110b, each may extend from a floor 312 of the nasal passage 308 behind the columella 310 and the fibrofatty tissue 305 or bulbous region around the base of the nostrils 314 to an inner wall (not shown) of the nostrils 314. In this way, the nasal dilator device 100 may be securely retained within the nose 304 with little or no pinching of or pressure being exerted on the septum 302. Furthermore, the ergonomic shape of the intermediate portions 108a, 108b allows the nasal dilator device to sit within the nose in a manner that may accommodate various shapes and sizes of noses, including those having hanging columellas 310.

In some embodiments, the first and second rib members 110a, 110b of the nasal dilator device 100 are composed of a flexible material and are generally squeezed or compressed by a user into a compressed state to allow insertion into the nasal passages 308 of the nose 304. The first and second rib members 110a, 110b may be biased to reform or revert to a natural uncompressed state and once inserted into the nasal passage 308, the first and second rib members 110a, 110b may each exert an outward force on the inner wall (not shown) of the nostril 314 and on the floor 312 of the nose 304, to thereby dilate the nasal passage 308. Thus, as opposed to exerting pressure on the septum 302 to dilate the nasal passage 308, the intermediate portions 108a, 108b, of nasal dilator device 100 are effective to cause the first and second rib members 110a, 110b to use the floor 312 of the nose 304 as a support structure for dilation of the nostrils 314. By using the floor 312 of the nose 304 as a support structure or anchor from which the first and second rib members 110a, 110b may launch or push off from, any pinching or exertion of force on the septum may be mitigated or avoided and a more comfortable and natural or anatomical fit may be achieved.

The nasal dilator device 100 is configured to cooperate with internal contours of the nose 304 and sit securely and comfortably in the nose, whilst mitigating obstruction of air flow through the nasal passage 308. For example, the rib members 110a, 110b, may be curved or arcuate along their length to correspond with the internal contours of the nose 304 and provide a more comfortable fit. In some embodiments, the first and second leg members 106a, 106b may be inclined toward each other or converge such that a relatively greater distance is provided between the first and second leg members 106a, 106b towards the central portion 104 in order to accommodate the columella 310 and to assist in holding the nasal dilator device 100 in place when worn.

Referring now to FIGS. 4A to 4D, there is illustrated a nasal dilator device, generally indicated at 400, according to some embodiments. The nasal dilator device 400 may comprise similar components and elements to those of nasal dilator device 100 depicted in FIGS. 1A to 1E and accordingly those similar components and elements are denoted like numerals.

In addition to those similar components and elements of nasal dilator device 100, nasal dilator device 400 may comprise a first and second releasable attachment mechanism 402a and 402b, respectively. The first and second releasable attachment mechanism 402a, 402b may comprise mating or interlocking components and may be employed to releasably attach the first and second rib members, 110a and 110b, respectively, to the U-shaped body 102, to thereby define first and second adjustable looped structures, 411a, and 411b, respectively.

In some embodiments, the first and second releasable attachment mechanisms 402a, 402b may comprise respective arms 404a, 404b, such as pins, extending from respective reverse or inner surfaces 406a, 406b of the first and second nostril engaging elements 112a, 112b. The first and second releasable attachment mechanisms 402a, 402b may comprise respective sockets 408a, 408b for receiving and/or engaging the respective arms 404a, 404b. The first and second releasable attachment mechanisms 402a, 402b may be configured to allow a user to selectively adjust a degree of dilation or expansion and contraction of the first and second rib members 110a and 110b with respect to the U-shaped body 102.

Figure 4A:
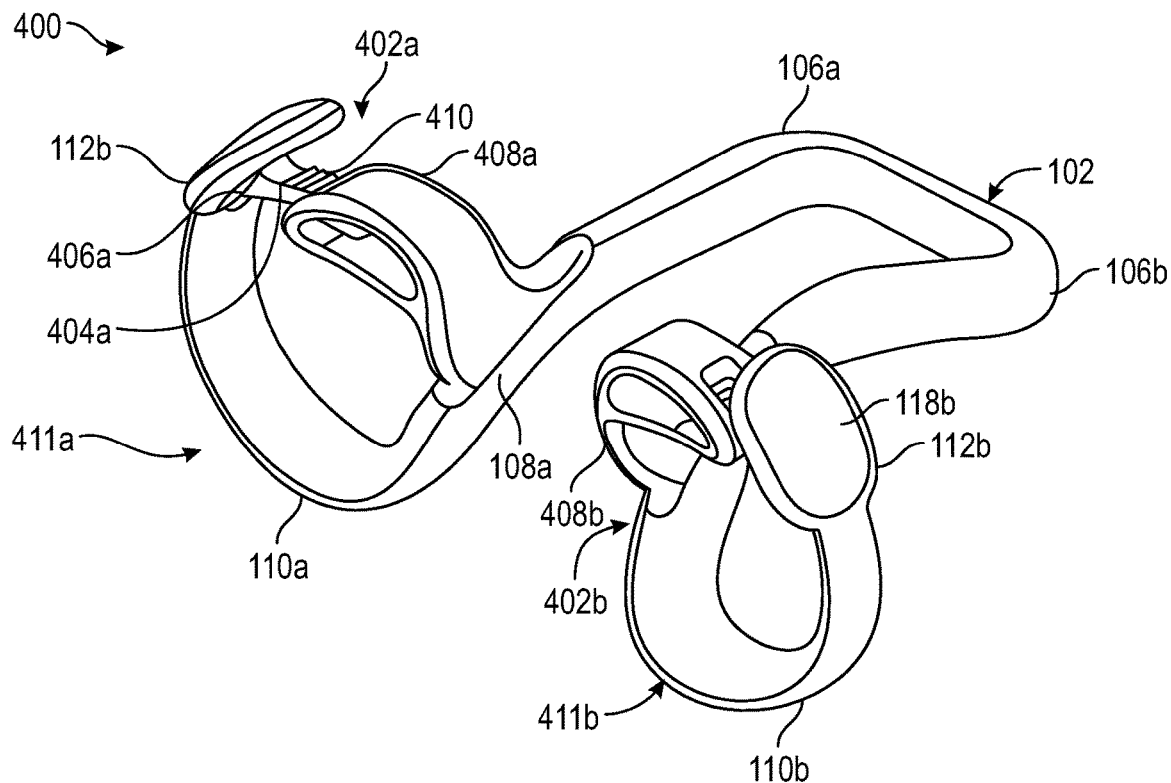
FIG. 4A is a rear perspective view of a nasal dilator device according to some embodiments.
Figure 4B:
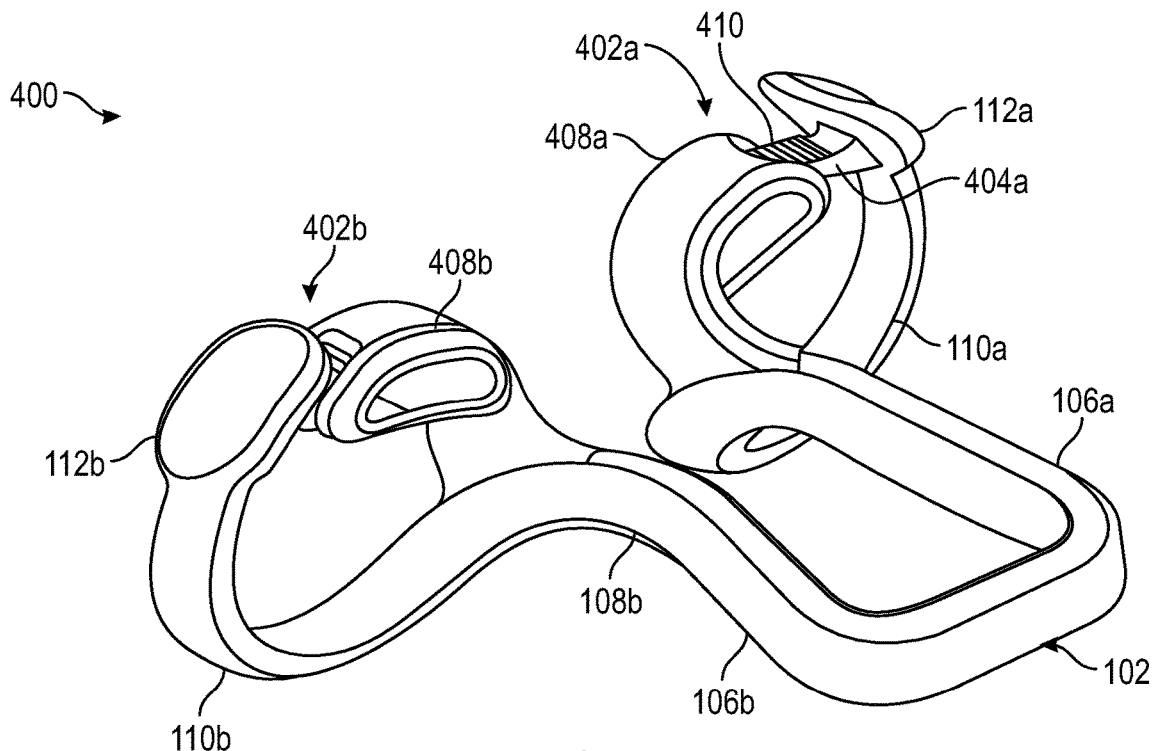
FIG. 4B is a front perspective view of the nasal dilator device of FIG. 4A.
Figure 4C:
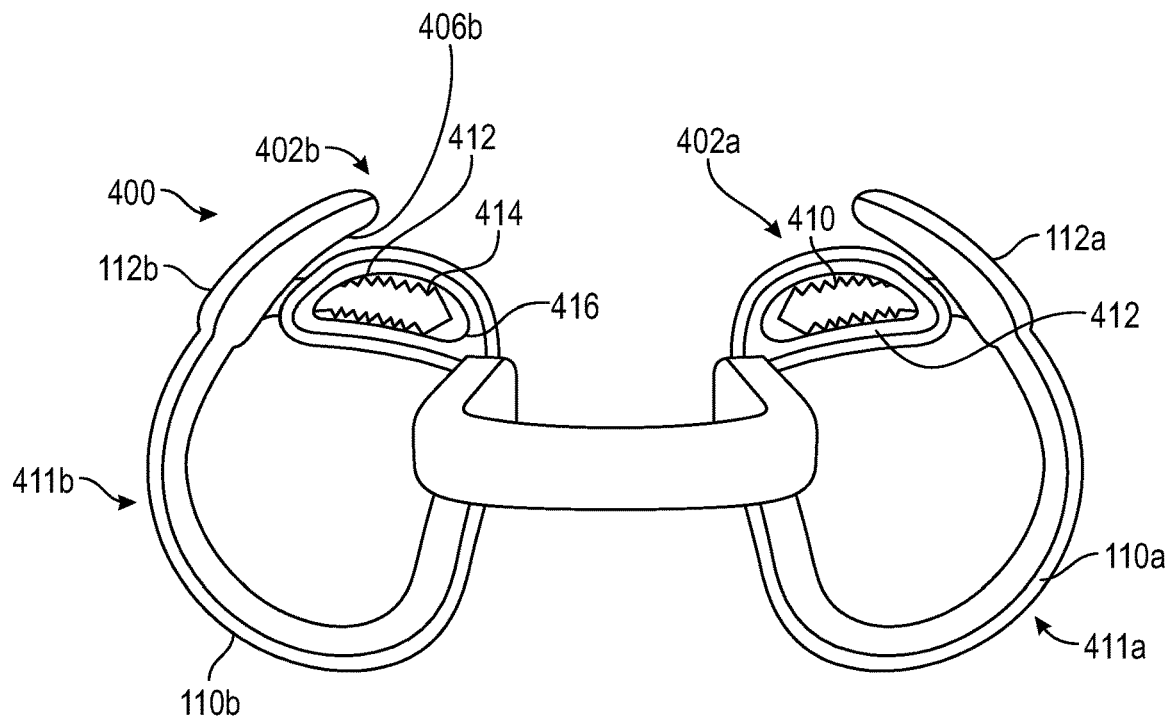
FIG. 4C is a front view of the nasal dilator device of FIG. 4A in a closed configuration.
Figure 4D:
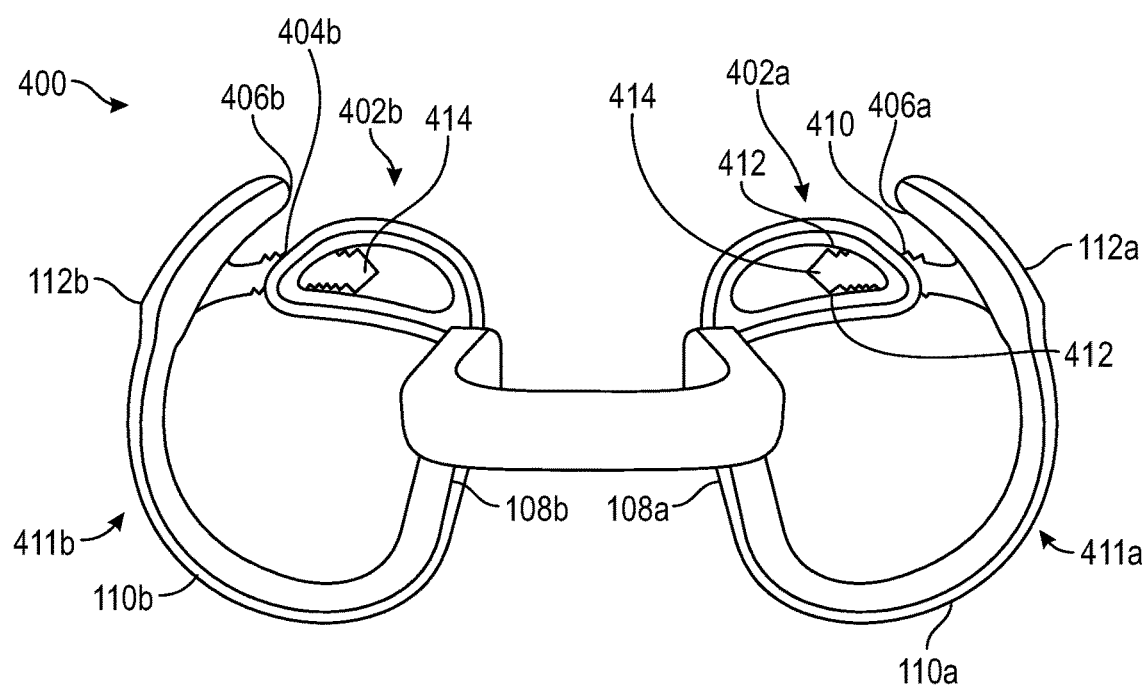
FIG. 4D is a front view of the nasal dilator device of FIG. 4A in a partially closed configuration.

For example, and as best illustrated in FIGS. 4C and 4D, the arms 404a, 404b may include at least one or a series of serrations, detents or protrusions 410 arranged to engage with at least one or a series of grooves or ridges 412 provided on or within the sockets 408a, 408b. For example, the grooves or ridges 412 may extend downwardly from a upper jaw portion 414 of the sockets 408a, 408b and/or may extend upwardly from a lower jaw portion 416.

Figure 5:
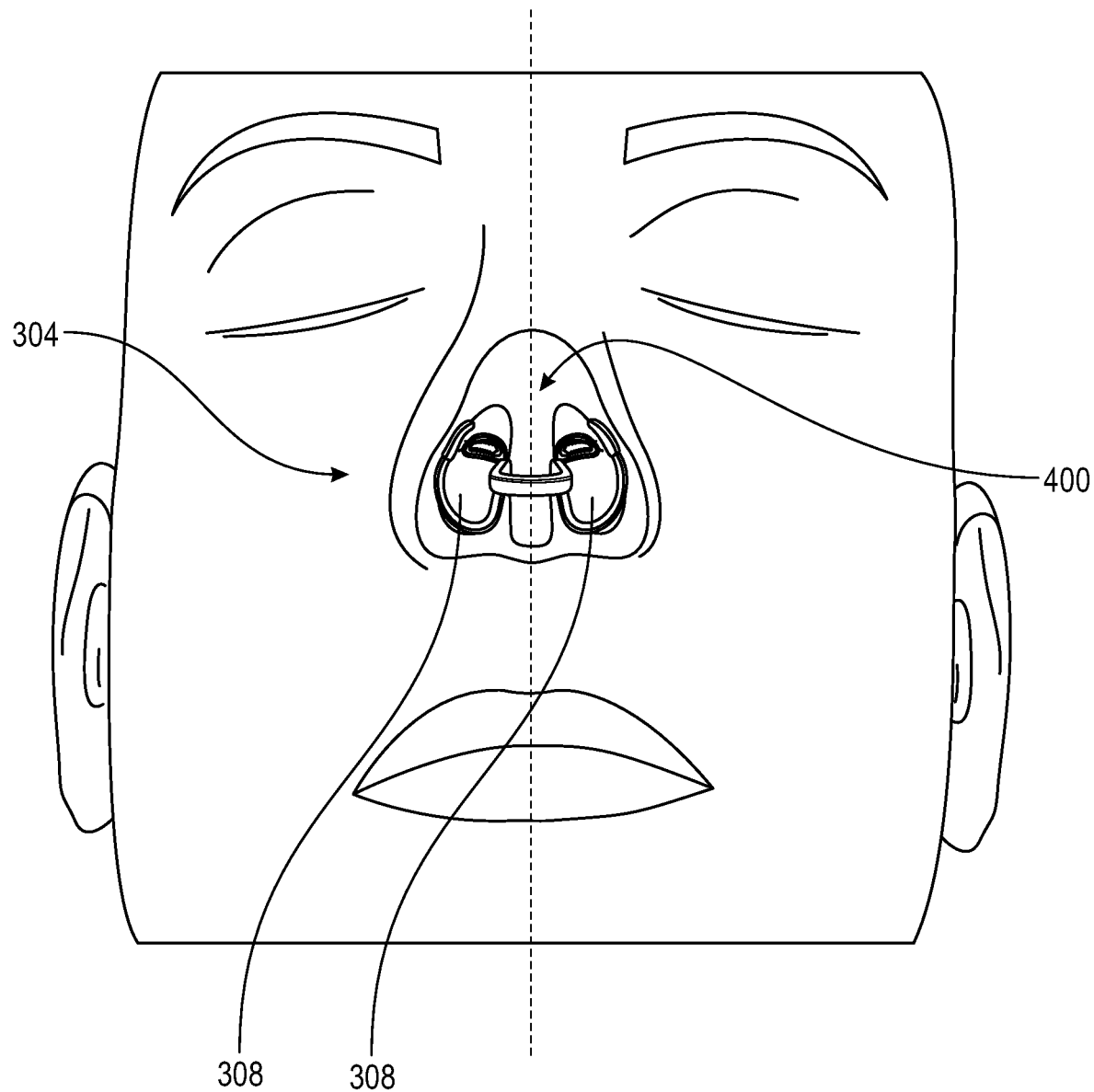
FIG. 5 is a front perspective view of a user donning the nasal dilator device of FIGS. 4A to 4D.

Application of sufficient force by a user to the first and second releasable attachment mechanisms 402a, 402b may be effective to move the arms 404a, 404b with respect to the sockets 408a, 408b and overcome a restrictive force between the detents 410 and the grooves 412 to allow the detents 410 and/or the grooves 412 to deform and the degree or level of dilation to be adjusted. The engagement of the detents 410 with the grooves 412 may provide a sufficient restrictive force to hold the arms 404a, 404b fixed when provided in the nose 304, as depicted in FIG. 5.

The arms 404a, 404b may comprise stoppers 414 at their ends to prevent or hinder the arms 404a, 404b from disengaging from or withdrawing from the respective sockets 408a, 408b. For example, application of a relatively large pulling force may be sufficient to cause the arms 404a, 404b to withdraw from the sockets 408a, 408b. In some embodiments, the stoppers 414 may be arrow shaped.

In some embodiments, the sockets 408a, 408b may be disposed on the first and second intermediate sections 108a, 108b and extend therefrom towards the respective arms 404a, 404b. The releasable attachment mechanisms 402a, 402b may be arranged to releasably attach or lock the first and second nostril engaging elements 112a, 112b to the first and second intermediate sections 108a, 108b.

In other embodiments, the sockets 408a, 408b may be disposed on the first and second leg members 106a, 106b and extend therefrom towards the respective arms 404a, 404b. The releasable attachment mechanisms 402a, 402b may be arranged to releasably attach or lock the first and second nostril engaging elements 112a, 112b to the first and second leg members 106a, 106b.

In other embodiments, the sockets 408a, 408b may be disposed on the first and second rib members 110a, 110b and extend therefrom towards the respective arms 404a, 404b. The attachment mechanisms 402a, 402b may be arranged to releasably attach or lock the first and second nostril engaging elements 112a, 112b to the first and second rib members 110a, 110b.

In other embodiments, the first and second releasable attachment mechanisms 402a, 402b may comprise respective sockets 408a, 408b, extending from the respective reverse or inner surfaces 406a, 406b, of the first and second nostril engaging elements 112a, 112b and respective arms 404a, 404b extending from the first and second intermediate sections 108a, 108b, the first and second leg members 106a, 106b, or the first and second rib members 110a, 110b.

As illustrated in FIG. 4C, the arms 404a, 404b may be fully or substantially fully inserted into the respective sockets 408a, 408b to enable the nasal dilator device 400 to adopt or assume a fully closed or substantially fully closed state, to thereby tighten or contract the looped structures 411a, 411b.

As illustrated in FIG. 4D, the arms 404a, 404b may be partially inserted into the sockets 408a, 408b to enable the nasal dilator device 400 to adopt or assume a partially closed state, to provide for looser or less tight looped structures 411a, 411b and accommodate variations in nasal passage sizes.

Figure 6A:
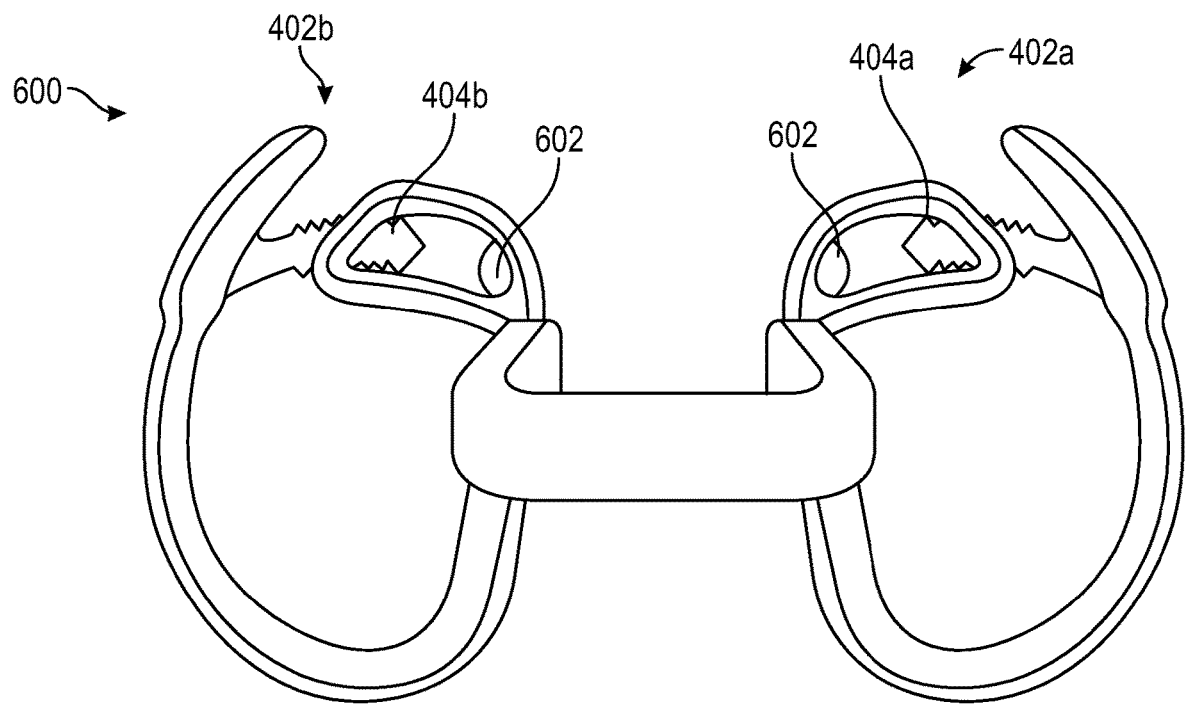
FIG. 6A is a front view of a nasal dilator device in a partially closed configuration, wherein the nasal dilator device includes a capsule, according to some embodiments.
Figure 6B:
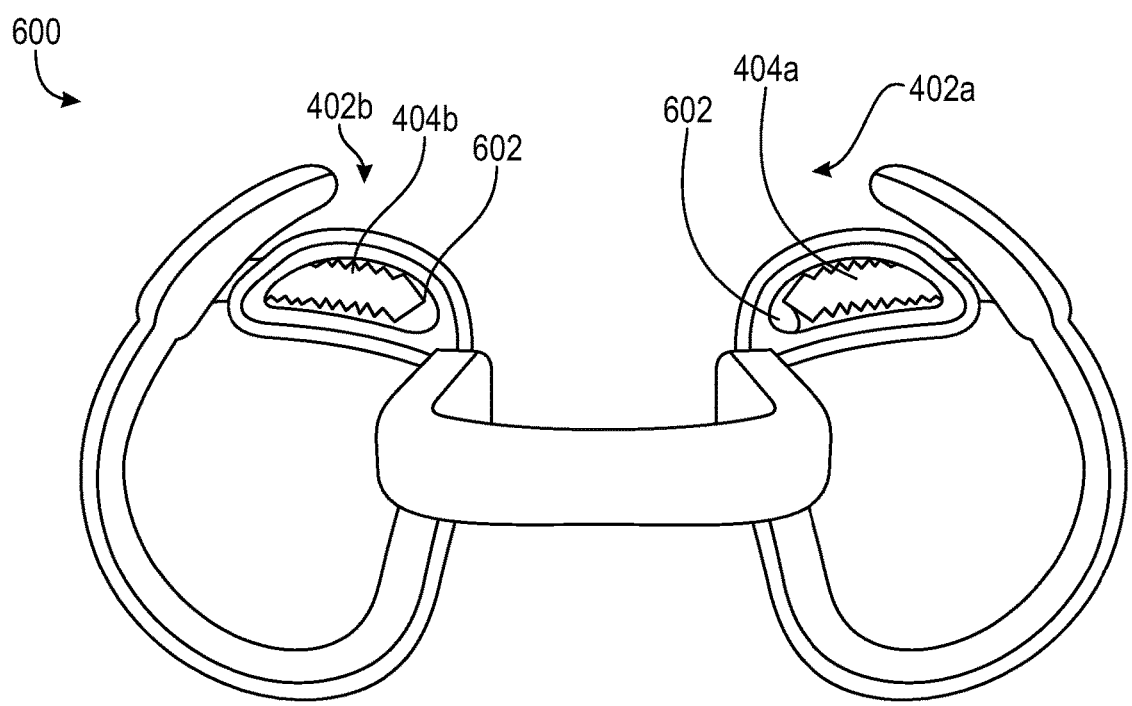
FIG. 6B is a front view of a nasal dilator device of FIG. 6A in a closed configuration.

Referring to FIGS. 6A and 6B, there is depicted a nasal dilator device 600 according to some embodiments. The nasal dilator device 600 may comprise similar components and elements to those of nasal dilator device 400 depicted in FIGS. 4A to 4D and accordingly those similar components and elements are denoted like numerals.

The nasal dilator device 600 comprises at least one capsule 602 disposed within respective sockets 408a, 408b. The capsule 602 may include an agent such as a medicament and/or a fragrance or aromatic agent. As depicted in FIG. 6B, the arms 404a, 404b are configured to activate, pierce or burst the capsules 602 to release the agent, medicament and/or fragrance or aromatic agent when inserted into the sockets 408a, 408b. In this way, the medicament and/or fragrance or aromatic agent is released only when the capsule 602 is activated, pierced or burst, thereby increasing a longevity or "shelf-life" and/or protecting the integrity of the medicament and/or aromatic agent. For example, the agent may be an aromatic scent such as an essential oil blend or synthetic fragrance blend to provide an olfactory and/or physiological response such as decongesting the nasal passages 318, promoting relaxation, promoting sleepiness, suppressing appetite or a medicament such as a drug to reduce pain such as a migraine.

Figure 7A:
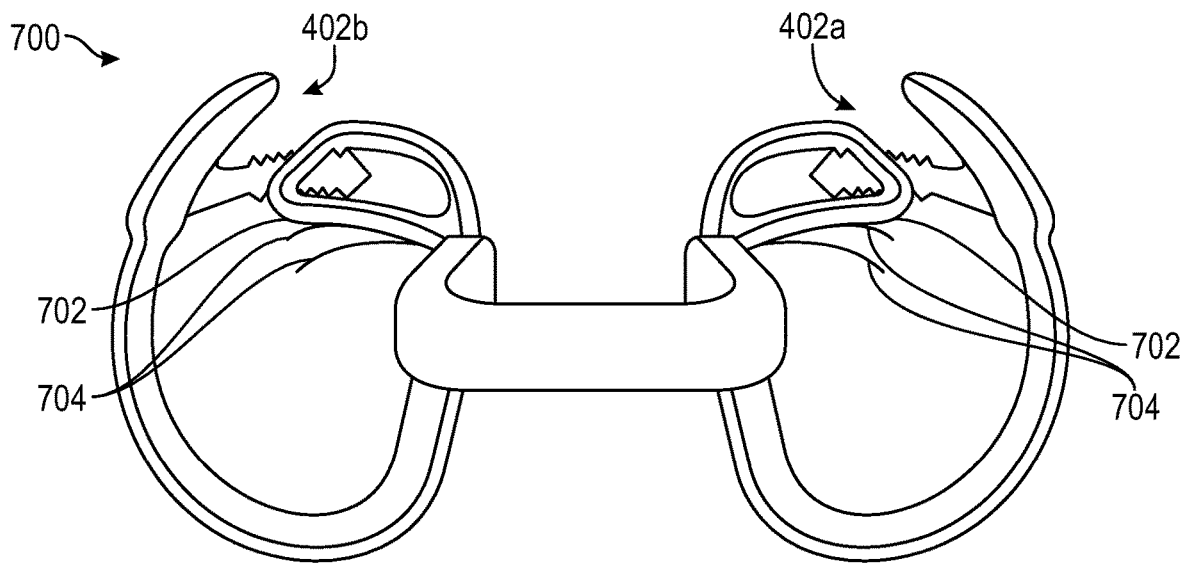
FIG. 7A is a front view of a nasal dilator device including a film according to some embodiments.
Figure 7B:
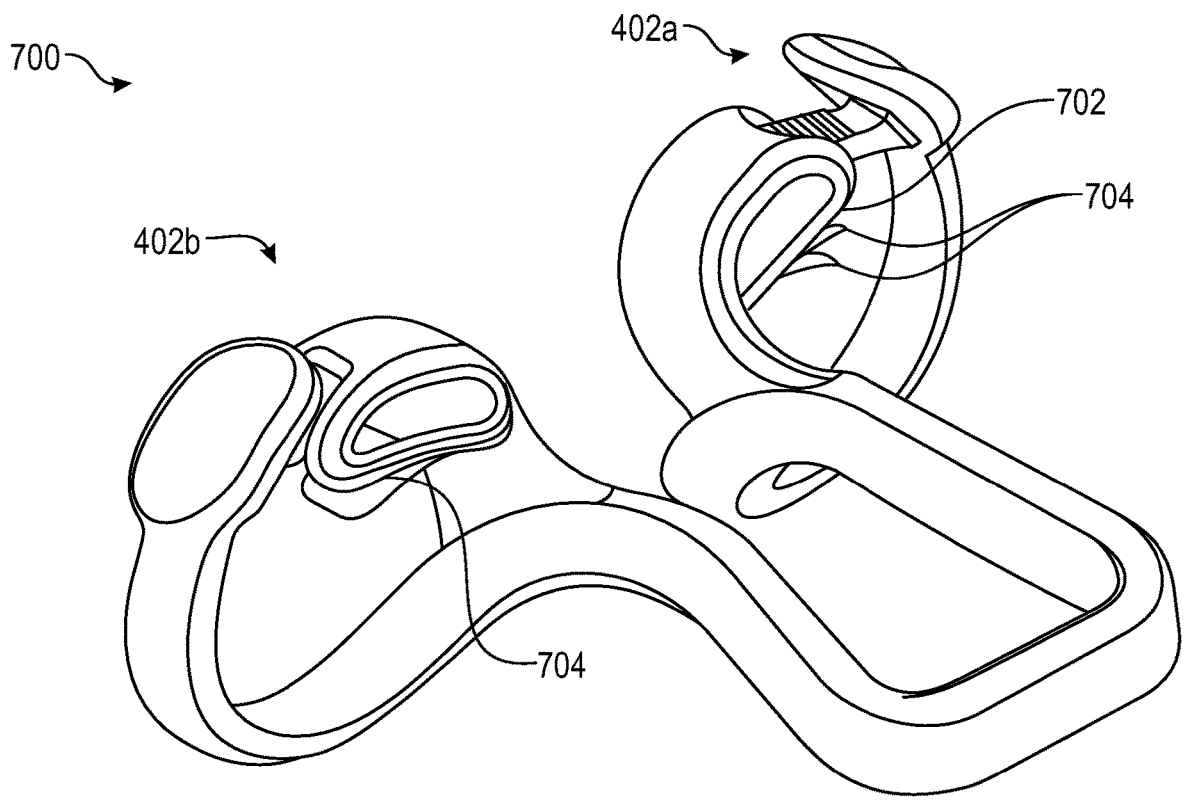
FIG. 7B is a front perspective view of the nasal dilator device of FIG. 7A.

Referring to FIGS. 7A and 7B, there is depicted the nasal dilator device 700 according to some embodiments. The nasal dilator device 700 may comprise similar components and elements to those of nasal dilator device 400 depicted in FIGS. 4A to 4D and accordingly those similar components and elements are denoted like numerals. The nasal dilator device 700 comprises at least one coating or film 702 arranged to release a fragrance, aroma or medicament. In some embodiments, the film 702 is arranged to release a fragrance, aroma or medicament in response to abrasion, such as scratching, scraping. The film 702 may be provided with an outer cover, seal or strip 704 to protect the film 702 from unintended abrasion, as depicted in FIGS. 7A and 7B at two separate stages of removal from the nasal dilator device 400.

In other embodiments, the coating or film 700 may be arranged to release a fragrance, aroma or medicament in response to the removal or peeling off of the outer cover, strip or seal 704. In some embodiments, a fragrance, aroma or medicament may be provided or retained between two strips or films 702 forming a blister.

The coating or film 702 may be comprise a polymer or a fibre. The coating or film 702 may be in the form of a "scratch and sniff" technology or peel off technology.

In some embodiments, as depicted in FIGS. 7A and 7B, the coating or film 702 may be disposed on a surface of at least one of the attachment mechanisms 402a, 402b, such as on an inner surface of the looped structures 411a, 411b. In other embodiments, the coating or film 702 may be disposed on the central portion 102, the first and second leg members 106a, 106b, the first and second intermediate sections 108a, 108b, the rib members 110a, 110b, and/or the first and second nostril engaging elements 112a, 112b.

In some embodiments, an aperture (not shown) is disposed in each of the first and second nostril engaging elements and is arranged to receive an agent, a compound, a medicament, a capsule, and/or a housing or compact arranged to receive an agent, medicament and/or a fragrance or aromatic agent. The agent may be absorbed by the inner walls of the nostrils transdermally and/or may be absorbed by mucosa in the nostrils 314.

Figure 8A:
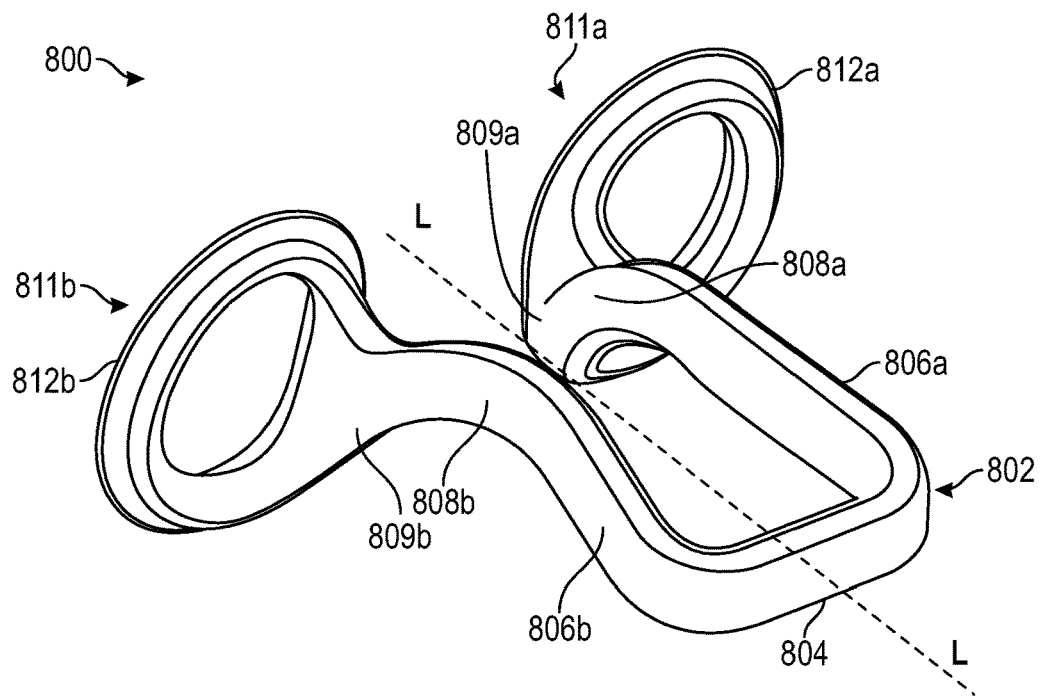
FIG. 8A is a front perspective view of a nasal dilator device according to some embodiments.
Figure 8B:
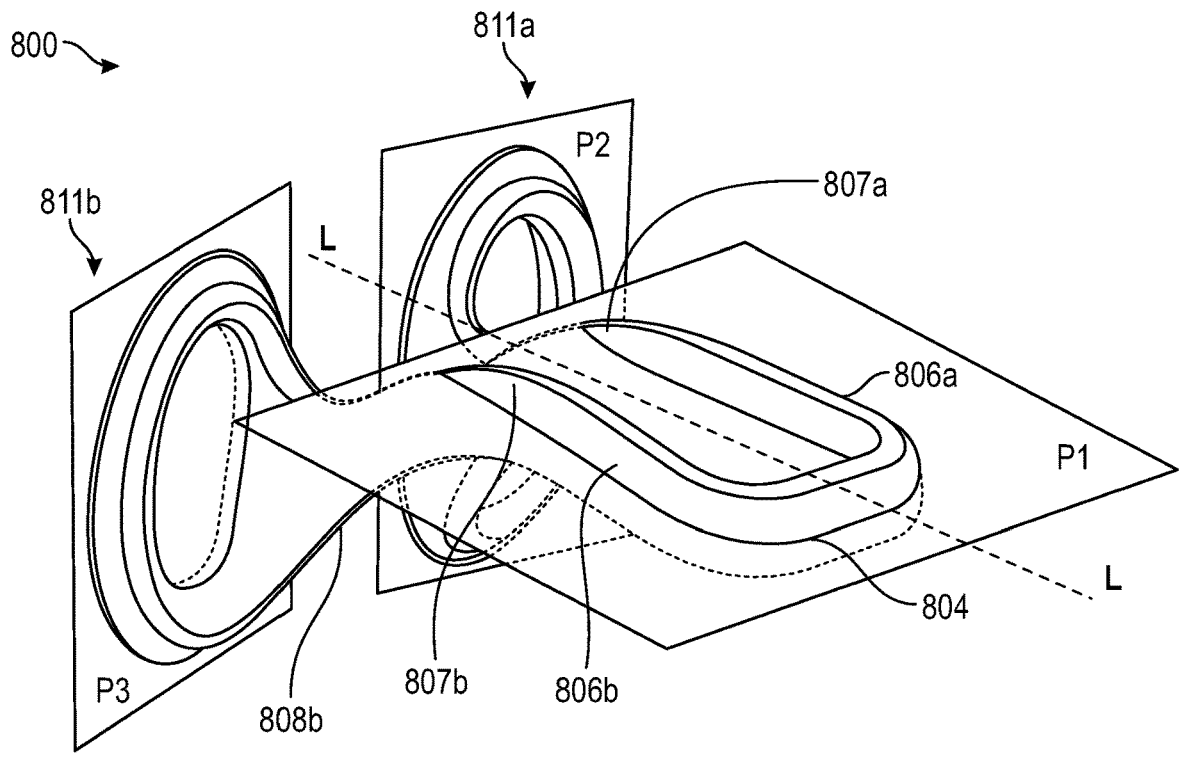
FIG. 8B is a further front perspective view of the nasal dilator device of FIG. 8A.

Referring to FIGS. 8A and 8B, there is depicted a nasal dilator device, generally indicated at 800 and substantially symmetrical about a longitudinal axis L, according to some embodiments. The nasal dilator device 800 may comprise a generally U-shaped body 802 having a central portion 804 and first and second leg members, 806a and 806b, respectively, extending from the central portion 804 in a first plane P1.

The nasal dilator device 800 comprises a first intermediate section 808a extending from an end 807a of the first leg member 806a and a second intermediate section 808b extending from an end 807b of the second leg member 806b. In some embodiments, and as depicted in FIGS. 8A and 8B, the first and second intermediate portions 808a, 808b, may be curved or arcuate along their length. In other embodiments, the first and second intermediate portions 808a, 808b may be substantially straight along their length or may comprise a plurality of angled or arcuate portions. For example, the first and second intermediate portions 808a, 808b may extend obtusely from the first and second ends 807a, 807b, for example, substantially at an angle of between approximately 95° and 130° to the longitudinal axis.

Figure 8C:
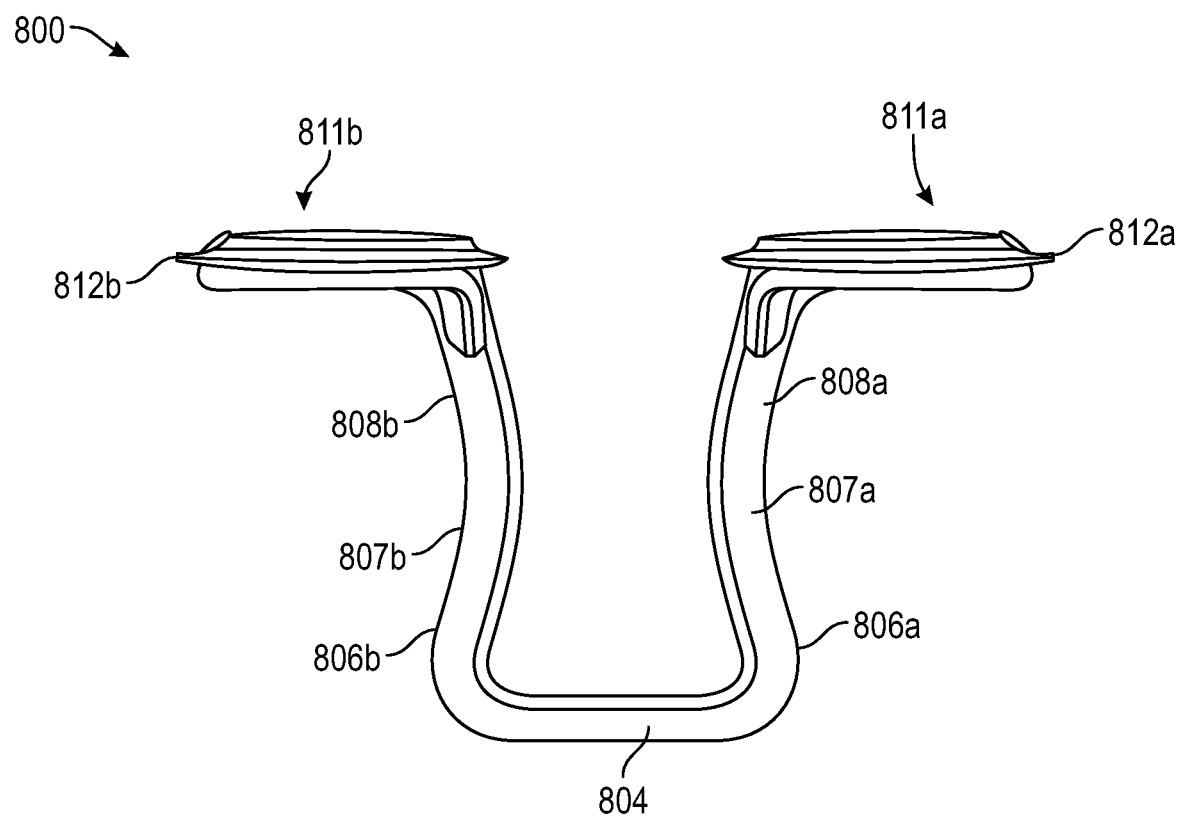
FIG. 8C is a top view of the nasal dilator device of FIG. 8A.

As depicted in FIGS. 8A to 8C, the nasal dilator device 800 comprises a first loop structure 811a projecting from the first intermediate section 808a in a second plane P2 and a second loop structure 811b projecting from the second intermediate section 808b in a third plane P3. In some embodiments, the first and second loop structures 811a, 811b may project substantially outward or lateral of the longitudinal axis of the generally U-shaped body 802 and away from one another. In some embodiments, the loop structure 811a, 811b may exhibit an elongate arched or curved profile which may substantially take the form of a circle, ellipse or parabola.

In some embodiments, the first intermediate section 808a may extend or transition between the first plane P1 and the second plane P2 to interconnect the end 807a of the first leg member 806a to a proximal end 809a of the first loop structure 811b and the second intermediate section 808b may extend or transition between the first plane P1 and the third plane P3 to interconnect the end 807b of the second leg member 806b to a proximal end 809b of the second loop structure 811b.

In some embodiments, the configuration of the first and second intermediate sections 808a, 808b may be associated with an orientation or location of the first and second loop structures 811a, 811b with respect to the U-shaped body 804. For example, the configuration of the first and second intermediate sections 808a, 808b may dictate or define an angle between the first and second planes, P1 and P2 and between the first and third planes, P1 and P3, respectively. The second and third planes, P2 and P3, may each form an acute angle, a right angle, or substantially right angle or an obtuse angle with the first plane P1. For example, the second and third planes P2 and P3, may be converging planes or intersecting planes and may each form an obtuse angle of approximately 95° to 130° with the first plane P1 such that the first and second intermediate sections 108a 108b take the form of obtuse arcuate sections. In some embodiments, the first, second and third planes, P1, P2, P3 may be different from each other and in some embodiments, the second and third planes, P2, P3 may be the same plane and may be different to the first plane P1.

In some embodiments, the first and second leg members 806a, 806b may be inclined toward each other or converge such that a relatively greater distance is provided between the first and second leg members 806a, 806b towards the central portion 804 in order to accommodate the columella 310 and to assist in holding the nasal dilator device 800 in place when worn.

In some embodiments, the first and second intermediate sections 808a, 808b may be inclined away from or diverge from one another to assist in urging the respective first and second loop structures 811a, 811b against inner walls of the nose when worn by the user. In some embodiments, the first and second loop structures 811a and 811b may comprise first and second flanged portions, 812a and 812b, respectively. For example, first and second flanged portions 812a and 812b may project from an outer surface of the loop structures 811a and 811b, respectively, and extend along at least a portion of a circumference of the loop structures 811a and 811b. In some embodiments, the first and second loop structures 811a and 811b may each comprise two or more flanged portions (not shown). For example, the more than two or more flanged portions (not shown) may project from an outer surface of the loop structures 811a and 811b and extend along at least a portion of a circumference of the loop structures 811a and 811b. The flanged portions 812a and 812b may provide additional compliance to the loop structures 811a, 811b and may provide for or create a drag effect which may improve retention of the nasal dilator device 1300 in a desired position despite movement of the user.

In some embodiments, the first and second flanged portions 812a and 812b may be comprise an overmould material, for example, flexible TPE, to thereby provide an improve sealing of the loop structures 811a and 811b to the nasal orifices.

Figure 9:
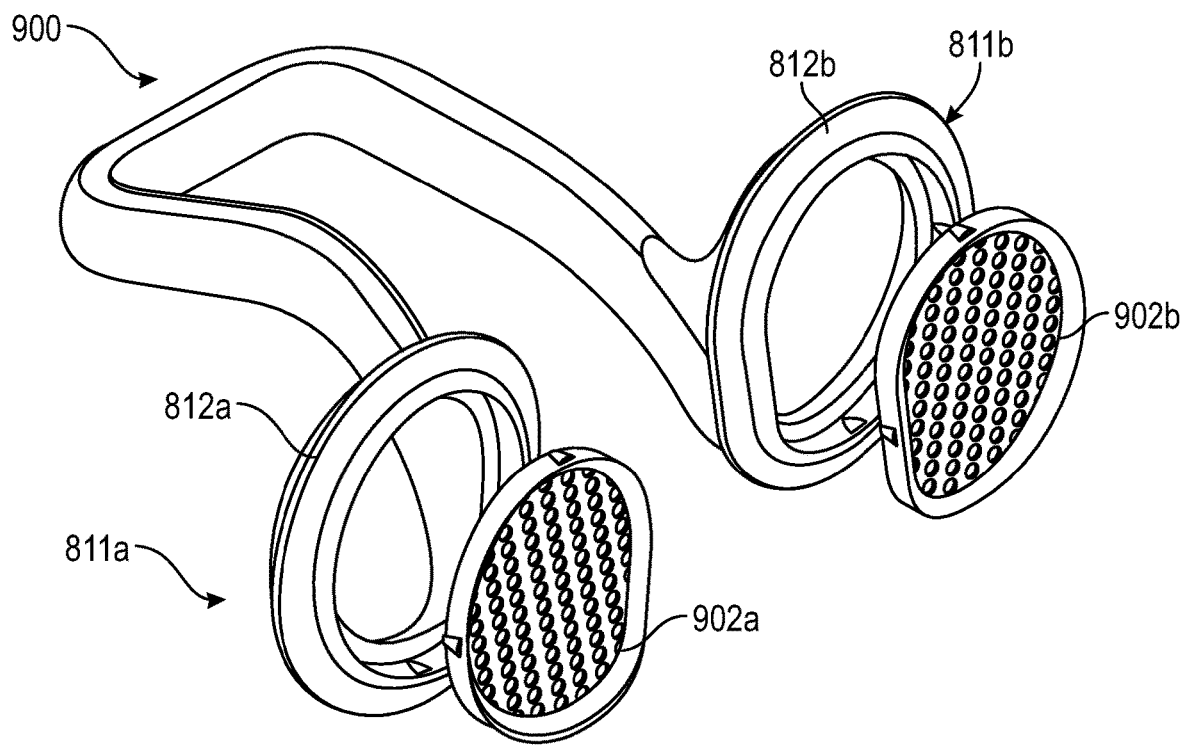
FIG. 9 is a rear perspective view of a nasal dilator device with an attachable filter, according to some embodiments.

Referring to FIG. 9, there is depicted the nasal dilator device 900 according to some embodiments. The nasal dilator device 900 may comprise similar components and elements to those of nasal dilator device 800 depicted in FIGS. 8A to 8C and accordingly those similar components and elements are denoted like numerals.

The first and second loop structures 811a, 811b, of the nasal dilator device 900 may be each arranged to receive a filter 902a, and 902b, respectively. The filters 902a, 902b, may be arranged or configured to span apertures defined by the first and second loop structures 811a, 811b.

The filters 902a, 902b may be composed of a fine woven mesh or an open celled porous material, such as a foam or compressed fibre. The filters 902a, 902b may be employed to filter out airborne particles such as bacteria, dust, pollens, and/or other allergens.

In some embodiments, as depicted in FIG. 9, the filters 902a, 902b, may be replaceable and may be arranged to be removeably connected to the first and second loop structures 811a, 811b respectively. For example, the filters 902a, 902b, may be configured to "snap-fit" into the first and second loop structures 811a, 811b respectively.

Figure 10:
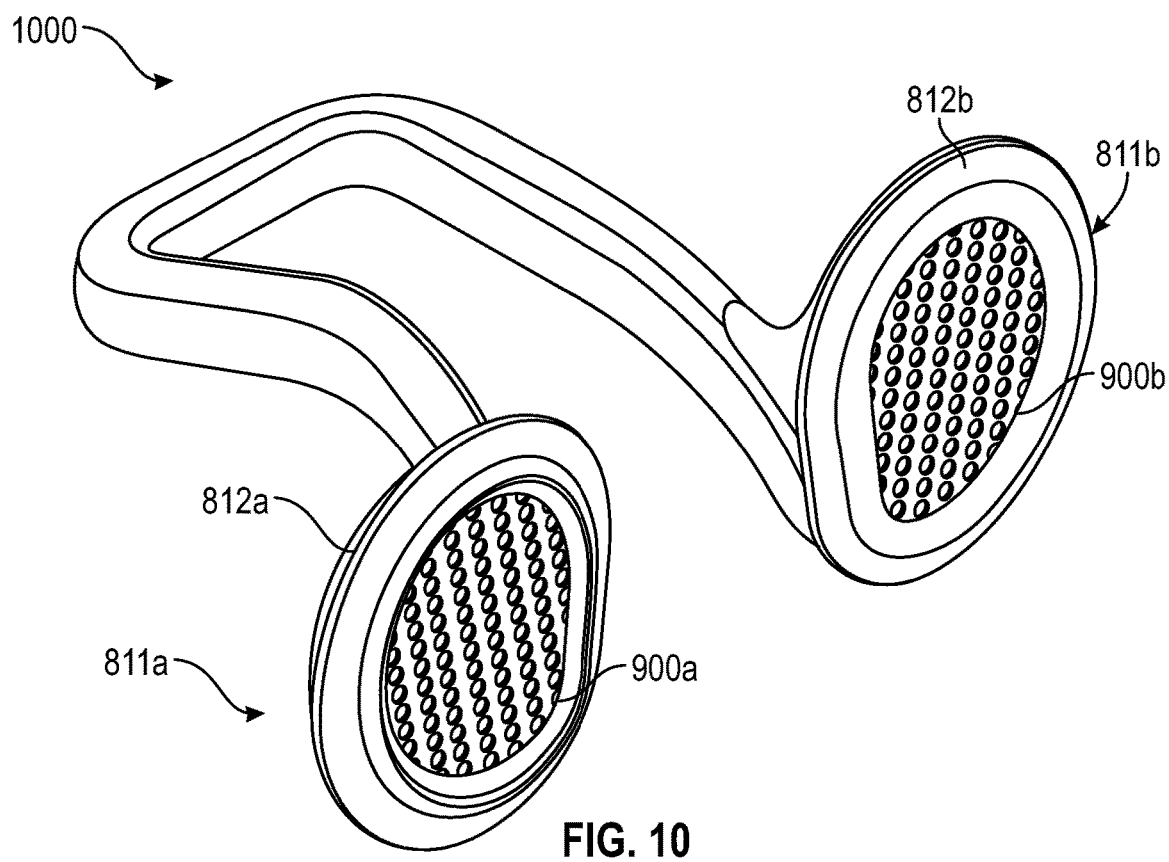
FIG. 10 is a rear perspective view of a nasal dilator device including a filter, according to some embodiments.

Referring to FIG. 10, there is depicted the nasal dilator device 1000 according to some embodiments. The nasal dilator device 1000 may comprise similar components and elements to those of nasal dilator device 800 depicted in FIGS. 8A to 8C and accordingly those similar components and elements are denoted like numerals The filters 902a, 902b of the nasal dilator device 1000 may be fixed to the first and second loop structures 811a, 811b respectively. For example, the filters 902a, 902b may be integrally formed with the first and second loop structures 811a, 811b or may be welded or ultrasonically welded to the first and second loop structures 811a, 811b.

In some embodiments, the nasal dilator device 100, 200, 400, 600, 700, 800, 900, 1000 may comprise an overmould disposed on at least one of the central portion, the leg members, the intermediate sections and the rib members. The overmould may be infused with a medicament and/or fragrance.

In some embodiments, the nasal dilator devices 100, 200, 400, 600, 700, 800, 900, 1000 may comprise a tab (not shown) extending outward from the central portion in a direction substantially opposite to the first and second leg members to assist with insertion, removal and/or placement of the nasal dilator device 100, 200, 400, 600, 700, 800, 900, 1000. The tab (not shown) may be removeable from the nasal dilator device, for example, by tearing the tab along a perforated line connecting the tab to the central portion 104, 804.

The U-shaped body 102, 802, the intermediate sections 108a, 108b, 808a, 808b, the rib members 110a, 110b, and the loop structure 811a, 811b may be composed of a polymer material such as thermoplastic elastomer (TPE) and/or thermoplastic polypropylene (PP). In some embodiments, the U-shaped body 102 and/or the intermediate sections 108a, 108b may are configured to be more rigid than the rib members 110a, 110b. For example, the U-shaped body 102 and/or the intermediate sections 108a, 108b and/or the rib members 110a, 110b may be composed of different materials or materials having differing hardness or stiffness. In some embodiments, the relative flexibility of the rib members 110a, 110b with respect to the U-shaped body 102 and/or the intermediate sections 108a, 108b may be derived from the length and/or thickness of the rib members 110a, 110b.

In some embodiments, an overall width of the nasal dilator device 100, 200, 400, 600, 700, 800, 900, 1000 may be in a range of approximately 20 mm to 35 mm when fully closed and approximately 25 mm to 40 mm when fully open, a length of the central portion 102, 802 may be in a range of approximately 5 mm to 10 mm, a length of the leg members 106a, 106b, 806a, 806b may be within a range of approximately 5 mm to 12 mm, and a length of the intermediate sections 108a, 108b, 808a, 808b may be in a range of approximately 7 mm to 15 mm and the rib members 110a, 110b, 810a, 810b may be in a range of approximately 15 mm to 30 mm. For example, in one embodiment, the overall width of the nasal dilator device 100, 200, 400, 600, 700, 800, 900, 1000 may be 25 mm when fully closed, 27.4 mm when open and the length of the leg members 106a, 106b, 806a, 806b may be 14.6 mm. In another embodiment, the overall width of the nasal dilator device 100, 200, 400, 600, 700, 800, 900, 1000 may be 27.2 mm when fully closed, 29.3 mm when open and the length of the leg members 106a, 106b, 806a, 806b may be 17.5 mm. In another embodiment, the overall width of the nasal dilator device 100, 200, 400, 600, 700, 800, 900, 1000 may be 29 mm when fully closed, 31.6 mm when open and the length of the leg members 106a, 106b, 806a, 806b may be 20.4 mm.

Figure 11:
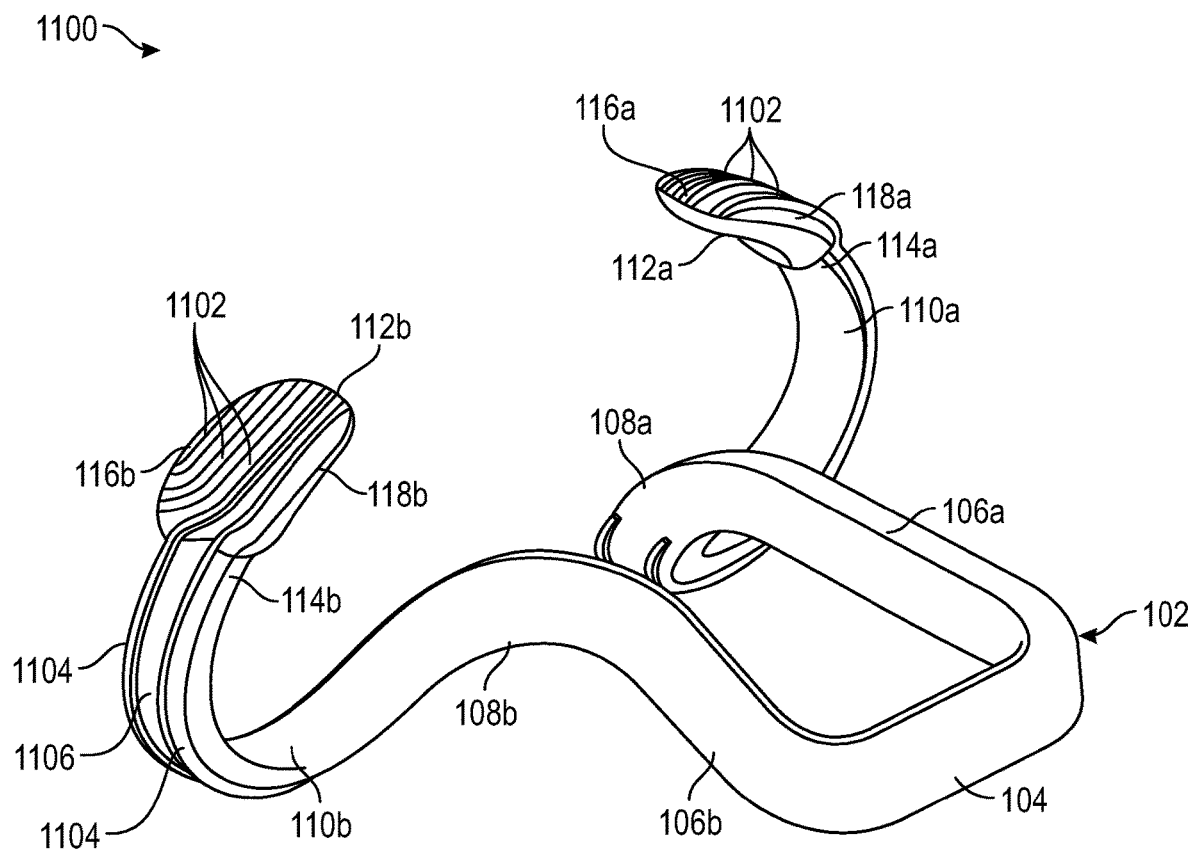
FIG. 11 is front perspective view of a nasal dilator device, according to some embodiments.

Referring now to FIG. 11, there is illustrated a nasal dilator device, generally indicated at 1100, according to some embodiments. The nasal dilator device 1100 may comprise similar components and elements to those of nasal dilator device 100 depicted in FIGS. 1A to 1E and accordingly those similar components and elements are denoted like numerals.

In some embodiments, as depicted in FIG. 11, the relatively large surface areas 116a, 116b of the nostril engaging members 112a, 112b are provided with a series of protrusions 1102. The nostril engaging members 112a, 112b may be substantially elongate, for example, extending from the distal ends 114a, 114b of the rib members 110a, 110b, and the protrusions 1102 may extend along a length of the surface areas 116a, 116b of the nostril engaging members 112a, 112b. In some embodiments, the surface areas 116a, 116b of the nostril engaging members 112a, 112b may be substantially oval, rectangular, triangular or truncated triangular in shape. In some embodiments, the series of protrusions 1102 may form a u-shaped pattern, a v-shaped pattern, or elongated v or ✓ (tick) shaped pattern, such as a chevron design, comprising a plurality of aligned u-shaped, v-shaped or elongated v or □ (tick) shaped protrusions 1102.

As depicted in FIG. 11, the rib members 110a, 110b of the nasal dilator device 1100 may comprise one or more projections 1104, flanges or ridges protruding from a major surface 1106 of the nasal dilator device 1100 and extending along at least a portion of a length of the rib members 110a, 110b. For example, the major surface 1106 of the nasal dilator device 1100 may be the surface of the nasal dilator device 1100 configured, in use, to engage with or face nasal passage walls of a user's nose. In some embodiments, as depicted in FIG. 11, the nasal dilator device 1100 may comprise first and second projections 1104, each forming a flange disposed at respective elongate edges 1106a, 1106b of the major surface 1106 of the nasal dilator device 1100.

The one or more projections 1104 extend from the distal ends 114a, 114b of the rib members 110a, 110b toward the intermediate sections 108a, 108b. For example, as depicted in FIG. 11, the one or more projections 1104 may integrate with and extend from corresponding protrusions 1102 of the series of protrusions 1102 provided on the surface areas 116a, 116b of the nostril engaging members 112a, 112b. In some embodiments, the one or more projections 1104 may be disposed on and project from the major surface 1106 of the intermediate sections 108a, 108b and/or the leg members 106a, 106b and/or the central portion 104 of the nasal dilator device 1100.

In some embodiments, the nasal dilator device 1100 may comprise pads 118a, 118b disposed on the enlarged surface areas 116a, 116b of the nostril engaging members 114a, 114b. The pads 118a, 118b may be composed of a relatively soft overmould material, for example, a polymer material such as thermoplastic elastomer (TPE). In some embodiments, the pads 118a, 118b may be configured to cooperate with and conform to the surface area 116a, 116b and the series of protrusions 1102 such that the overmoulded series of protrusions 1102 project or protrude from the overmoulded surface area 116a, 116b. In other embodiments, the surface areas 116a, 116b of the nostril engaging members 112a, 112b may be substantially smooth or flat and the pads 118a, 118b may comprise or form the series of protrusions 1102. For example, the pads 118a, 118b may be substantially elongate, for example, extending from the distal ends 114a, 114b of the rib members 110a, 110b, and the protrusions 1102 may extend along a length of the pads 118a, 118b.

In some embodiments, an overmould material may be provided on at least a portion of the rib members 110a, 110b, on at least a portion of the intermediate sections 108a, 108b, and/or on at least a portion of the u-shaped body 102. For example, the overmould may be configured to cooperate with and conform to the major surface 1106 of the nasal dilator device 1100 and the one or more projections 1104 such that the overmoulded projections 1104 project or protrude from the overmoulded major surface 1106. In other embodiments, the major surface 1106 of the nasal dilator device 1100 may be substantially smooth or flat and an overmould disposed thereon may comprise or form the one or more projections or ridges 1104.

The series of protrusions 1102 and/or the one or more projections 1104 may provide a comfortable and/or grippable surface for engaging with the inner walls of the nose in use. The series of protrusions 1102 and/or the one or more projections 1104 may provide for or create a drag effect which may improve retention of the nasal dilator device 1100 in a desired position in a user's nose, in use, despite movement or motion of the user.

Figure 12A:
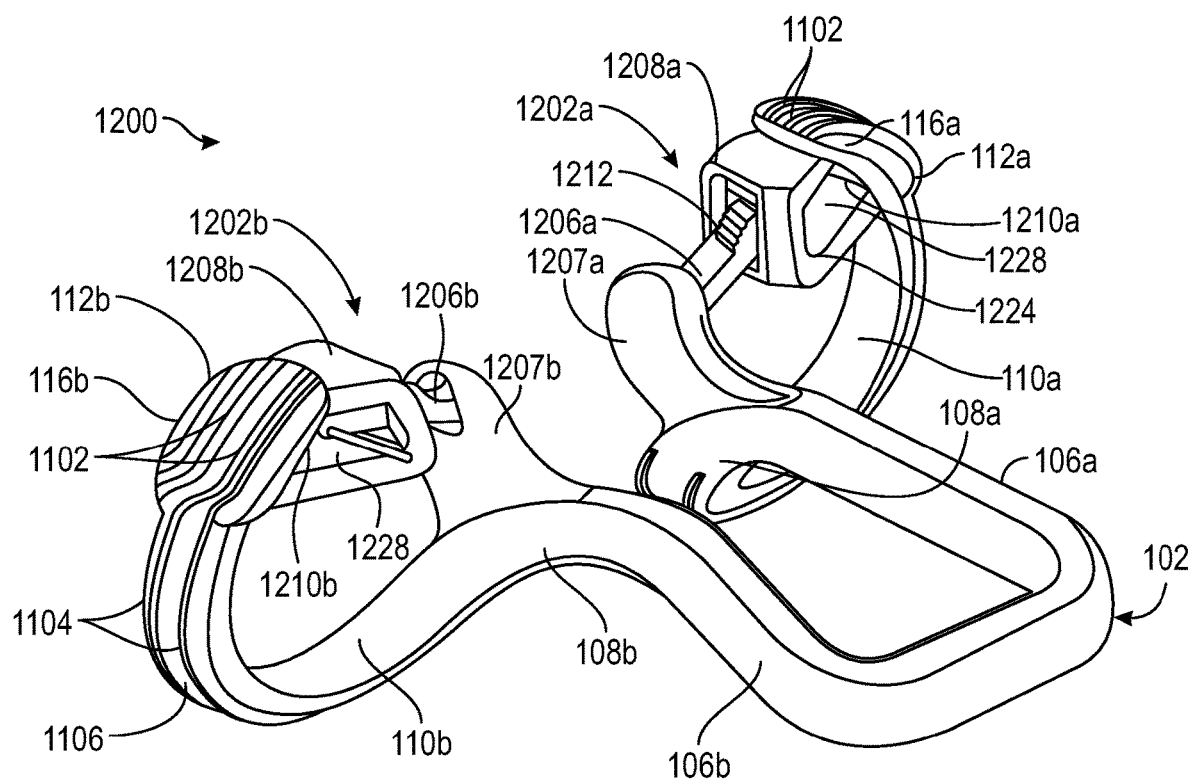
FIG. 12A is front perspective view of a nasal dilator device, according to some embodiments.
Figure 12B:
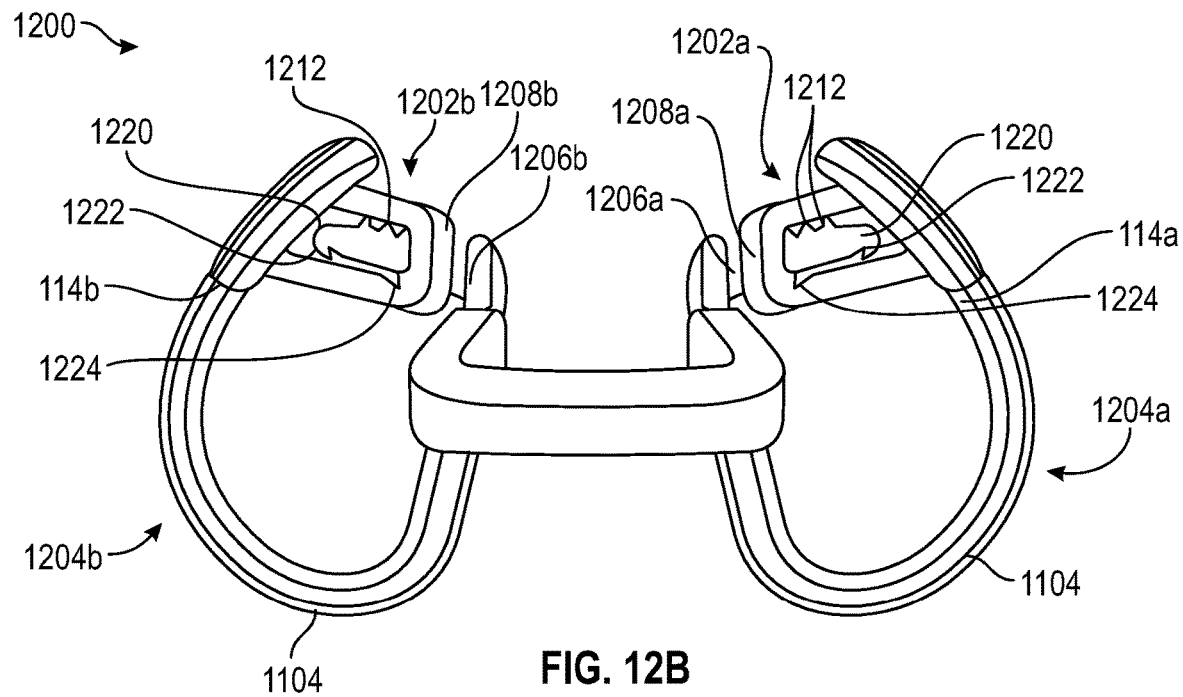
FIG. 12B is a front view of the nasal dilator device of FIG. 12A in a substantially closed configuration.
Figure 12C:
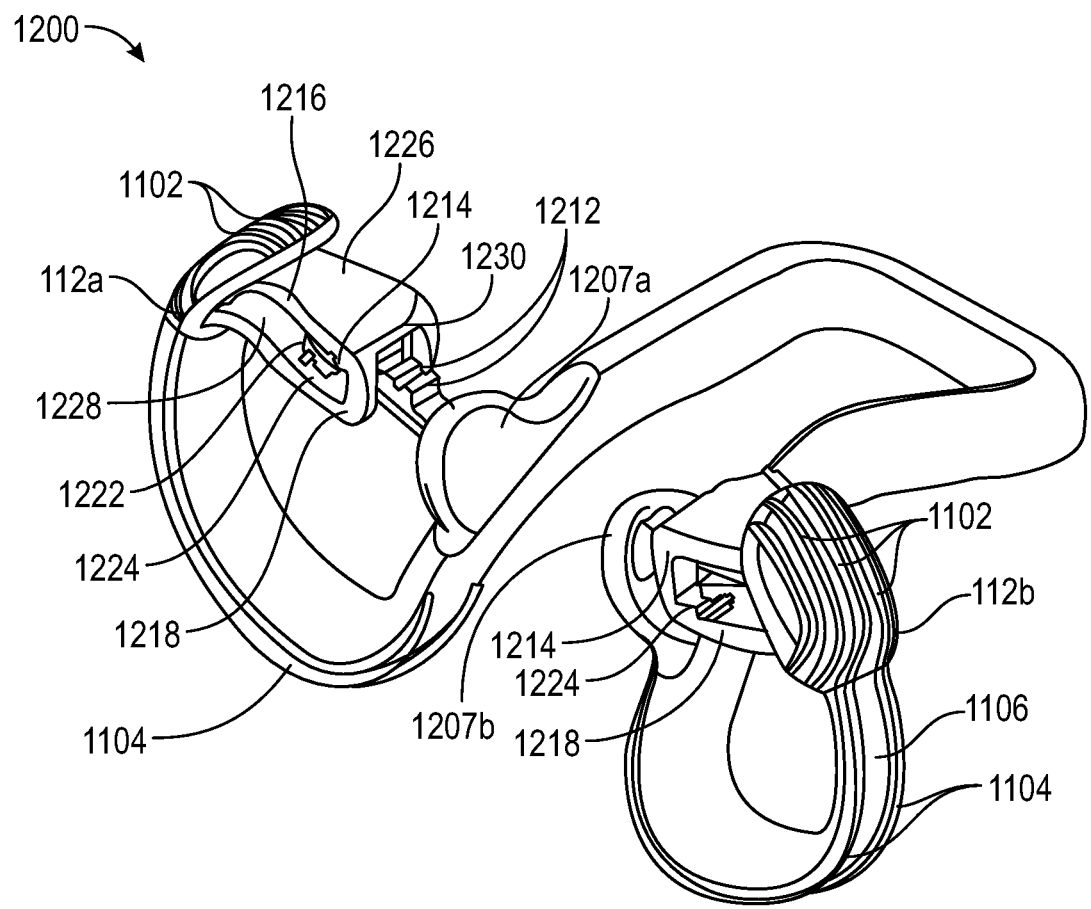
FIG. 12C is a rear perspective view of the nasal dilator device of FIG. 12A.

Referring now to FIGS. 12A, 12B and 12C, there is illustrated a nasal dilator device, generally indicated at 1200, according to some embodiments. The nasal dilator device 1200 may comprise similar components and elements to those of nasal dilator device 1100 depicted in FIG. 11 and accordingly those similar components and elements are denoted like numerals.

In addition to those similar components and elements of nasal dilator device 1100, nasal dilator device 1200 may comprise a first and second releasable attachment mechanism 1202a and 1202b, respectively. The first and second releasable attachment mechanism 1202a, 1202b may comprise mating or interlocking components and may be employed to releasably attach the first and second rib members, 110a and 110b, respectively, to the U-shaped body 102, to thereby define first and second adjustable looped structures, 1204a, and 1204b, respectively. The first and second releasable attachment mechanisms 1202a, 1202b may allow a user to selectively adjust a degree of dilation or expansion and contraction of the first and second rib members 110a and 110b with respect to the U-shaped body 102.

The first and second releasable attachment mechanisms 1202a, 1202b may comprise respective arms 1206a, 1206b, such as pins, and respective sockets 1208a, 1208b for receiving and/or engaging the respective arms 1206a, 1206b.

As illustrated in FIGS. 12A, 12B and 12C, the arms 1206a, 1206b may be disposed on and extend from respective first and second intermediate sections 108a, 108b toward respective sockets 1208a, 1208b provided on opposite or inner surfaces 1210a, 1210b of the first and second nostril engaging elements 112a, 112b. In some embodiments, as shown in FIGS. 12A and 12C, the first and second arms 1206a, 1206b extend from respective first and second arm supports 1207a, 1207b projecting from respective first and second intermediate sections 108a, 108b. The releasable attachment mechanisms 1202a, 1202b may therefore be arranged to releasably attach or lock the first and second nostril engaging elements 112a, 112b to the first and second intermediate sections 108a, 108b.

In other embodiments, the first and second arms 1206a, 1206b may be disposed on and extend from respective first and second rib members 110a, 110b toward respective first and second sockets 1208a, 1208b to allow the releasable attachment mechanisms 1202a, 1202b to releasably attach or lock the first and second nostril engaging elements 112a, 112b to the first and second rib members 110a, 110b or the first and second arms 1206a, 1206b may be disposed on and extend from respective first and second leg members 106a, 106b toward respective first and second sockets 1208a, 1208b to allow the releasable attachment mechanisms 1202a, 1202b to releasably attach or lock the first and second nostril engaging elements 112a, 112b to the first and second leg members 106a, 106b.

In other embodiments, the first and second releasable attachment mechanisms 1202a, 1202b may comprise first and second arms 1206a, 1206b extending from the respective opposite or inner surfaces 1210a, 1210b of the first and second nostril engaging elements 112a, 112b and first and second sockets 1208a, 1208b extending from the first and second intermediate sections 108a, 108b, the first and second rib members 110a, 110b, or the first and second leg members 106a, 106b.

Referring again to FIGS. 12A, 12B and 12C, the first and second arms 1206a, 1206b may include at least one or a series of serrations, detents or protrusions 1212 arranged to engage with at least one or a series of grooves or ridges 1214 provided on or within the sockets 1208a, 1208b. For example, the grooves or ridges 1214 may extend downwardly from a upper jaw portion 1216 of the sockets 1208a, 1208b and/or may extend upwardly from a lower jaw portion 1218.

Application of sufficient force by a user to the first and second releasable attachment mechanisms 1202a, 1202b may be effective to move the arms 1206a, 1206b with respect to the sockets 1208a, 1208b and overcome a restrictive force between the detents 1212 and the grooves 1214 to allow the detents 1212 and/or the grooves 1214 to deform and the degree or level of dilation to be adjusted. The engagement of the detents 1212 with the grooves 1214 may provide a sufficient restrictive force to hold the arms 1206a, 1206b fixed when provided in a user's nose.

As depicted in FIG. 12, the arms 1206a, 1206b may each comprise a stopper or catch 1220 provided at their free ends to prevent or hinder the arms 1206a, 1206b from disengaging from or withdrawing from the respective sockets 1208a, 1208b. For example, in some embodiments, the catch 1220 comprises a hook portion 1222 which is configured to cooperate with a corresponding notch 1224 disposed in an upper or lower jaw portion 1216, 1218 of the socket. Application of a relatively large pulling force may be sufficient to cause the catch 1220 to disengage with the notch 1224 and to cause the arms 1206a, 1206b to withdraw from the sockets 1208a, 1208b.

In some embodiments, as best shown in FIGS. 12A and 12C, the sockets 1208a, 1208b may take the form of substantially elongate housings 1226 provided with apertures 1228 or gaps in side walls of the housing 1226. The housings 1226 may be substantially wedge shaped and taper along their length towards opposite or inner surfaces 1210a, 1210b, of the first and second nostril engaging elements 112a, 112b to provide a relatively broad opening to receive the arms 1206a, 1206b. The elongate or wedge shaped housing 1226 may provide for an improved engagement between the arms 1206a, 1206b and sockets 1208a, 1208b and more robust releasable attachment mechanisms 1202a, 1202b. For example, the elongate or wedge shaped housing 1226 may allow a face 1230 of the socket housing to engage with and lie substantially flush with the arm supports 1207a, 1207b, the intermediate sections 108a, 108b, rib members 110a, 110b, or leg members 106a, 106b, when the arms 1206a, 1206b are fully engaged within the sockets 1208a, 1208b, when the nasal dilator device 1200 assumes a closed state. For example, in use, such a configuration may mitigate contact between the sockets 1208a, 1208b and the septum and relative movement or twisting of the sockets as a result of contact with the septum. The elongate or wedge shaped housing 1226 may facilitate improved or easier adjustment of the first and second releasable attachment mechanisms 1202a, 1202b.

The arms 1206a, 1206b may be fully or substantially fully inserted into the respective sockets 1208a, 1208b to enable the nasal dilator device 1200 to adopt or assume a fully closed or substantially fully closed state, to thereby tighten or contract the looped structures 1211a, 1211b. The arms 1206a, 1206b may be partially inserted into the sockets 1208a, 1208b to enable the nasal dilator device 1200 to adopt or assume a partially closed state, to provide for looser or less tight looped structures 1204a, 1204b and accommodate variations in nasal passage sizes.

As depicted in FIGS. 12A, 12B, and 12C, the nasal dilator device 1200 may include a series of protrusions 1102 disposed on the nostril engaging members 112a, 112b, and/or one or more projections 1104 protruding from the major surface 1106 of the nasal dilator device 1200, as discussed with reference to FIG. 11.

Similar to the embodiment of nasal dilator device 600 depicted in FIG. 6, in some embodiments, the nasal dilator device 1200 may comprise at least one capsule (not shown), which may include an agent such as a medicament and/or a fragrance or aromatic agent, disposed within respective sockets 1208a, 1208b. The arms 1206a, 1206b may be configured to activate, pierce or burst the capsule (not shown) to release the agent, medicament and/or fragrance or aromatic agent when they are inserted into the sockets 1208a, 1208b. In this way, the medicament and/or fragrance or aromatic agent is released only when the capsule (not shown) is activated, pierced or burst, thereby increasing a longevity or "shelf-life" and/or protecting the integrity of the medicament and/or aromatic agent.

Similar to the embodiment of nasal dilator device 700 depicted in FIG. 7, in some embodiments, the nasal dilator device 1200 may comprise at least one coating or film (not shown) arranged to release a fragrance, aroma or medicament. For example, the film (not shown) may be disposed on a surface of at least one of the attachment mechanisms 1202a, 1202b, such as on an inner surface of the looped structures 1204a, 1204b, on the central portion 102, on the first and second leg members 106a, 106b, on the first and second intermediate sections 108a, 108b, on the rib members 110a, 110b, and/or on the first and second nostril engaging elements 112a, 112b.

In some embodiments, the film (not shown) is arranged to release a fragrance, aroma or medicament in response to abrasion, such as scratching, scraping and may be provided with an outer cover, seal or strip to protect the film (not shown) from unintended abrasion. In other embodiments, the coating or film (not shown) may be arranged to release a fragrance, aroma or medicament in response to the removal or peeling off of an outer cover, strip or seal. In some embodiments, a fragrance, aroma or medicament may be provided or retained between two strips or films (not shown) forming a blister. For example, the coating or film (not shown) may comprise a polymer or a fibre and/or may be in the form of a "scratch and sniff" technology or peel off technology.

Figure 13A:
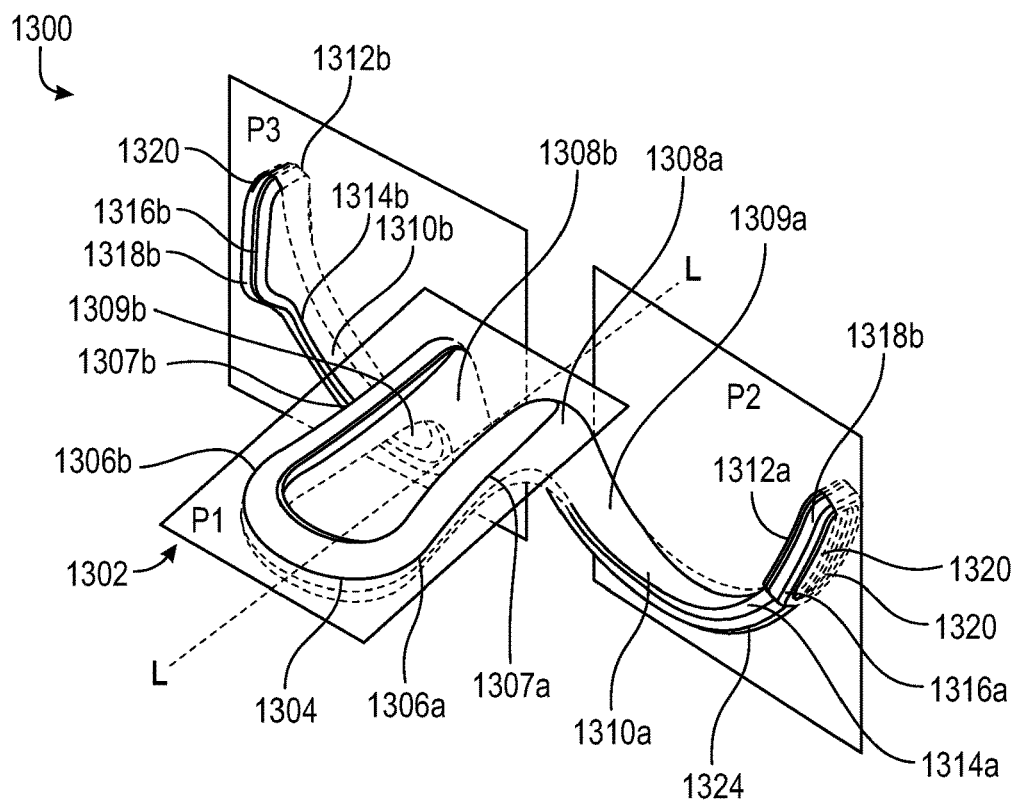
FIG. 13A is front perspective view of a nasal dilator device, according to some embodiments.
Figure 13B:
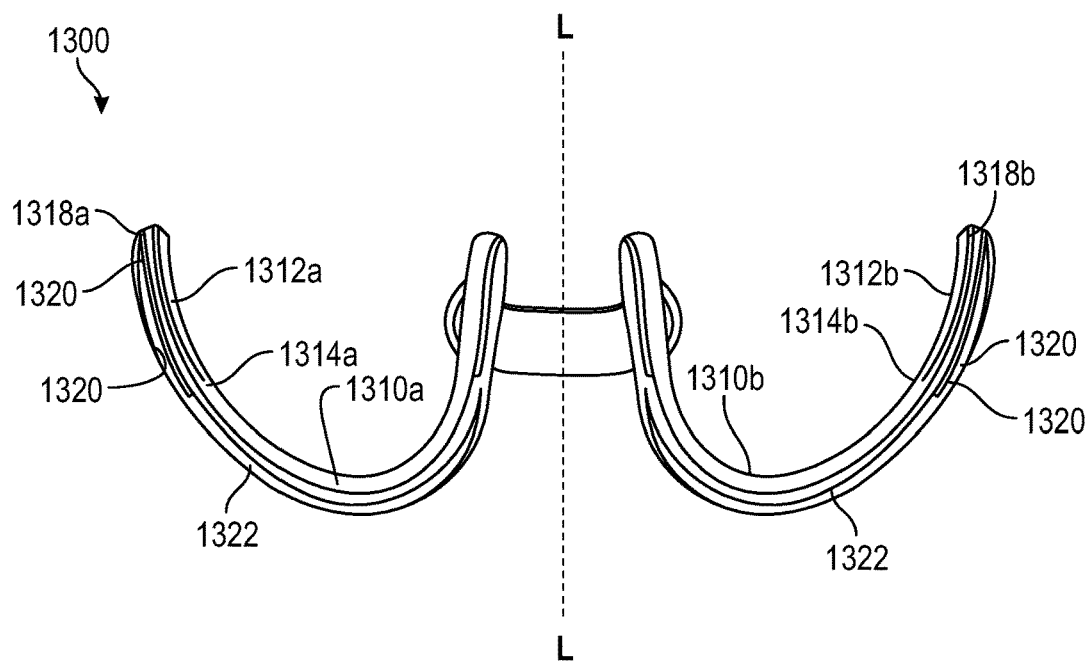
FIG. 13B is back view of the nasal dilator device of FIG. 13A.

Referring to FIGS. 13A and 13B, there is illustrated a nasal dilator device, generally indicated at 1300. The nasal dilator device 1300 is substantially symmetrical about a longitudinal axis L, according to some embodiments, and comprises a generally U-shaped body 1302 having a central portion 1304 and first and second leg members, 1306a and 1306b, respectively, extending from the central portion 1304 in a first plane P1.

The nasal dilator device comprises a first intermediate section 1308a extending from an end 1307a of the first leg member 1306a and a second intermediate section 1308b extending from an end 1307b of the second leg member 1306b. In some embodiments, and as depicted in FIGS. 13A and 13B, the first and second intermediate portions 1308a, 1308b, may be angled, curved or arcuate along their length and/or may comprise a plurality of angled or arcuate portions. In some embodiments, the first and second intermediate portions 108a, 108b may comprise L-shaped or right angled sections. For example, the first and second intermediate portions 108a, 108b may extend from the first and second ends 107a, 107b in a substantially perpendicular direction to the longitudinal axis L to form substantially right angled intermediate portions.

The nasal dilator device 1300 comprises a first rib member 1310a projecting from the first intermediate section in a second plane P2 and a second rib member 1310b projecting from the second intermediate section 1308b in a third plane P3. For example, and as best depicted in FIG. 13A, the first intermediate section 1308a may connect the end 1307a of the first leg member 1306a to a proximal end 1309a of the first rib member 1310a and the second intermediate section 1308b may connect the end 1307b of the second leg member 1306b to a proximal end 1309b of the second rib member 110b. In some embodiments, the first intermediate section 1308a extends from the first plane P1 to the second plane P2 and the second intermediate section 1308b extends from the first plane P1 to the third plane P3.

In some embodiments, the first and second rib members 1310a, 1310b may project substantially outward or laterally of the longitudinal axis of the U-shaped body 1302. For example, the first and second rib members 1310a, 1310b may be cantilever rib members that extend from the first and second intermediate sections 1308a, 1308b, respectively outwardly from the longitudinal axis and away from one another in a substantially cantilever manner. In some embodiments, the first and second rib members 1310a, 1310b may be arcuate rib members 1310a, 1310b or arcuate cantilever rib members 1310a, 1310b.

In some embodiments, the first and second rib members 1310a, 1310b may exhibit an elongate arched or bow-like profile which may approximate at least a portion of a circle, ellipse or parabola. For example, the first and second rib members 1310a, 1310b may extend arcuately along the second and third planes, P2 and P3, respectively in a direction substantially toward the first plane P1.

The first and second rib members 1310a, 1310b may be flexible and resiliently biased away from the first and second intermediate sections 1308a, 1308b respectively, to allow the first and second rib members 1310a, 1310b to be compressed for insertion into the nose of a user and to reform once placed inside the nose to thereby dilate the nostrils.

In some embodiments, the configuration of the first and second intermediate sections 1308a, 1308b may be associated with an orientation, positioning or location of the first and second rib members 1310a, 1310b with respect to the U-shaped body 1302. For example, the configuration of the first and second intermediate sections 1308a, 1308b may dictate or define a relationship or an angle between the first plane P1 and the second plane P2 and between the first plane P1 and the third plane P3, respectively. The second and third planes, P2 and P3, may each form an acute angle, a right angle, or substantially right angle or an obtuse angle with the first plane P1.

For example, in some embodiments, the first and second intermediate sections 1308a 1308b may take the form of substantially right angled sections such that the second and third planes P2, P3 each form a right angle with the first plane P1. In other embodiments, the first and second intermediate sections 1308a 1308b may take the form of obtuse angled or arcuate sections such that the second and third planes P2 and P3, each form an obtuse angle with the first plane P1. In other embodiments, the first and second intermediate sections 1308a 1308b may take the form of acute angled or arcuate sections such that the second and third planes P2 and P3, each form an acute angle with the first plane P1.

In some embodiments, the second and third planes P2 and P3, may be converging planes such that the first and second cantilever rib members are angled and/or extend substantially toward the central portion of the U-shaped body. In other embodiments, the second and third planes are diverging planes such that the first and second cantilever rib members are angled and/or extend substantially toward the central portion of the U-shaped body.

In some embodiments, the first, second and third planes, P1, P2, P3 may be different from each other and in some embodiments, the second and third planes, P2, P3 may be the same plane and may be different to the first plane P1. In some embodiments, the first and second planes P1, P2 may be orthogonal to the first plane P1.

For example, in some embodiments, the nasal dilator device 1300 is configured to be orientated such that, in use, the central portion 1304 spans a septum 302, and in particular, a columella (the terminal section or fleshy external end of the septum) of a nose and is positioned toward a tip of the nose and the first and second leg members 1306a, 1306b extend inward of respective nasal orifices, along a nasal passage and/or the septum of the nose. The first and second leg members 1306a, 1306b, may extend inward at an angle of approximately 30 to 40 degrees to a midline of the nose. The first and second intermediate sections 1308a, 1308b may engage with the septum and extend from the septum behind the columella and alar fibrofatty tissue or bulbous region around the base of the nostrils of the nose allowing the first and second rib members, in use, to extend along the respective nasal orifices to an inner wall of the nostrils behind the columella and the fibrofatty tissue or bulbous region around the base of the nostrils to an inner wall of the nostrils. In this way, the nasal dilator device 1300 may be securely retained within the nose with little or no pinching of or pressure being exerted on the septum.

The first and second intermediate sections 1308a, 1308b may be inclined away from or diverge from one another to assist in urging the respective first and second rib members 1310a, 1310b against inner walls of respective nostrils when worn by the user.

As depicted in FIGS. 13A and 13B, the first and second rib members 1310a, 1310b, of the nasal dilator device 1300 may comprise respective first and second nostril engaging elements, 1312a and 1312b, disposed at distal ends 1314a, 1314b, of the first and second arcuate rib members 1310a, 1310b, respectively, for engaging with inner walls of respective nostrils when worn by a user. In some embodiments, the first and second nostril engaging elements, 1312a, 1312b may comprise relatively large surface areas 1316a, 1316b with respect to the first and second arcuate rib members 1310a, 1310b.

In some embodiments, the first and second nostril engaging elements, 1312a, 1312b, may extend at an angle to or arcuately from the respective first and second distal ends 1314a, 1314b, of the respective first and second rib members 1310a, 1310b. For example, the first and second nostril engaging elements, 1312a, 1312b, may extend from the first and second planes, P2, P3, respectively and may extend in a direction away from the central portion 104 of the U-shaped body 1302.

In some embodiments, the first and second nostril engaging elements 1312a, 1312b may have pads 1318a, 1318b, disposed thereon, to engage with the inner walls of the nostrils of a user, in use. For example, the pads 1318a, 1318b may be disposed on the relatively large major surface areas 1316a, 1316b of the nostril engaging elements, 1312a and 1312b and may be enlarged with respect to the first and second arcuate rib members 1310a, 1310b, and/or the nostril engaging elements, 1312a, 1312b. The pads 1318a, 1318b of the nasal dilator device 1300 may be composed of a relatively soft overmould material, for example a polymer material such as thermoplastic elastomer (TPE) to provide a comfortable and/or grippable surface for engaging with the inner walls of the nostrils in use.

In some embodiments, as depicted in FIGS. 13A and 13B, the relatively large surface areas 1316a, 1316b of the nostril engaging members 1312a, 1312b are provided with a series of protrusions 1320. The nostril engaging members 1312a, 1312b may be substantially elongate, for example, extending from the distal ends 1314a, 1314b of the rib members 1310a, 1310b, and the protrusions 1320 may extend along a length of the surface areas 1316a, 1316b of the nostril engaging members 1312a, 1312b. In some embodiments, the surface areas 1316a, 1316b of the nostril engaging members 1312a, 1312b may be substantially oval, rectangular, triangular or truncated triangular in shape. In some embodiments, the series of protrusions 1320 may form a u-shaped pattern, a v-shaped pattern, or elongated v or ✓ (tick) shaped pattern, such as a chevron design, comprising a plurality of aligned u-shaped, v-shaped or elongated v or ✓ (tick) shaped protrusions 1320.

As depicted in FIGS. 13A and 13B, the rib members 1310a, 1310b of the nasal dilator device 1300 may comprise one or more projections 1322, flanges or ridges protruding from a major surface 1324 of the nasal dilator device 1300 and extending along at least a portion of a length of the rib members 1310a, 1310b. For example, the major surface 1324 of the nasal dilator device 1300 may be the surface of the nasal dilator device 1300 configured, in use, to engage with or face nasal passage walls of a user's nose. In some embodiments, as depicted in FIGS. 13A and 13B, the nasal dilator device 1300 may comprise first and second projections 1322, each forming a flange disposed at respective elongate edges of the major surface 1324 of the nasal dilator device 1300.

The one or more projections 1322 may extend from the distal ends 1314a, 1314b of the rib members 1310a, 1310b toward the intermediate sections 1308a, 1308b. For example, as depicted in FIG. 13A, the one or more projections 1322 may integrate with and extend from corresponding protrusions 1320 of the series of protrusions 1320 provided on the surface areas 1316a, 1316b of the nostril engaging members 1312a, 1312b. In some embodiments, the one or more projections 1322 may be disposed on and project from the major surface 1324 of the intermediate sections 1308a, 1308b and/or the leg members 1306a, 1306b and/or the central portion 1304 of the nasal dilator device 1300.

In some embodiments, the pads 1318a, 1318b may be configured to cooperate with and conform to the surface area 1316a, 1316b and the series of protrusions 1320 such that the overmoulded series of protrusions 1320 project or protrude from the overmoulded surface area 1316a, 1316b. In other embodiments, the surface areas 1316a, 1316b of the nostril engaging members 1314a, 1314b may be substantially smooth or flat and the pads 1318a, 1318b may comprise or form the series of protrusions 1320. For example, the pads 1318a, 1318b may be substantially elongate, for example, extending from the distal ends 1314a, 1314b of the rib members 1310a, 1310b, and the protrusions 1320 may extend along a length of the pads 1318a, 1318b.

In some embodiments, an overmould material may be provided on at least a portion of the rib members 1310a, 1310, on at least a portion of the intermediate sections 1308a, 1308b, and/or on at least a portion of the u-shaped body 1302. For example, the overmould may be configured to cooperate with and conform to the major surface 1322 of the nasal dilator device 1300 and the one or more projections 1322 such that the overmoulded projections 1322 project or protrude from the overmoulded major surface 1324. In other embodiments, the major surface 13024 of the nasal dilator device 1300 may be substantially smooth or flat and an overmould disposed thereon may comprise or form the one or more projections or ridges 1322.

The series of protrusions 1320 and/or the one or more projections 1322 may provide a comfortable and/or grippable surface for engaging with the inner walls of the nose in use. For example, activities that are percussive, such as running, are often associated with the production of skin perspiration which may reduce the mechanical and frictional attachment of other nasal devices to the nasal passage of the user causing the devices to move from a position intended by the user and therefore requiring readjustment. However, the series of protrusions 1320 and/or the one or more projections 1322 may provide for or create a drag effect which may improve retention of the nasal dilator device 1300 in a desired position in a user's nose, in use, despite motion or skin perspiration of the user.

Referring now to FIGS. 14A, 14B, 14C, 14D, 14E and 14E, there is illustrated a nasal dilator device, generally indicated at 1400, according to some embodiments. The nasal dilator device 1400 may comprise similar components and elements to those of nasal dilator device 1300 depicted in FIGS. 13A and 13B and accordingly those similar components and elements are denoted like numerals.

In addition to those similar components and elements of nasal dilator device 1300, nasal dilator device 1400 may comprise a first and second releasable attachment mechanism 1402a and 1402b, respectively. The first and second releasable attachment mechanism 1402a, 1402b may comprise mating or interlocking components and may be employed to releasably attach the first and second rib members, 1310a and 1310b, respectively, to the U-shaped body 1302, to thereby define first and second adjustable looped structures, 1404a, and 1404b, respectively. The first and second releasable attachment mechanisms 1402a, 1402b may allow a user to selectively adjust a degree of dilation or expansion and contraction of the first and second rib members 1310a and 1310b with respect to the U-shaped body 1302.

The first and second releasable attachment mechanisms 1402a, 1402b may comprise respective arms 1406a, 1406b, such as pins, and respective sockets 1408a, 1408b for receiving and/or engaging the respective arms 1406a, 1406b.

As illustrated in FIG. 14A to 14F, the arms 1406a, 1406b may be disposed on and extend from respective first and second intermediate sections 1308a, 1308b toward respective sockets 1408a, 1408b provided on opposite or inner surfaces 1410a, 1410b of the first and second nostril engaging elements 1312a, 1312b. The releasable attachment mechanisms 1402a, 1402b may therefore be arranged to releasably attach or lock the first and second nostril engaging elements 1312a, 1312b to the first and second intermediate sections 1308a, 1308b.

In other embodiments, the first and second arms 1406a, 1406b may be disposed on and extend from respective first and second rib members 1310a, 1310b toward respective first and second sockets 1408a, 1408b to allow the releasable attachment mechanisms 1402a, 1402b to releasably attach or lock the first and second nostril engaging elements 1312a, 1312b to the first and second rib members 1310a, 1310b or the first and second arms 1406a, 1406b may be disposed on and extend from respective first and second leg members 1306a, 1306b toward respective first and second sockets 1408a, 1408b to allow the releasable attachment mechanisms 1402a, 1402b to releasably attach or lock the first and second nostril engaging elements 1312a, 1312b to the first and second leg members 1306a, 1306b.

Figure 15:
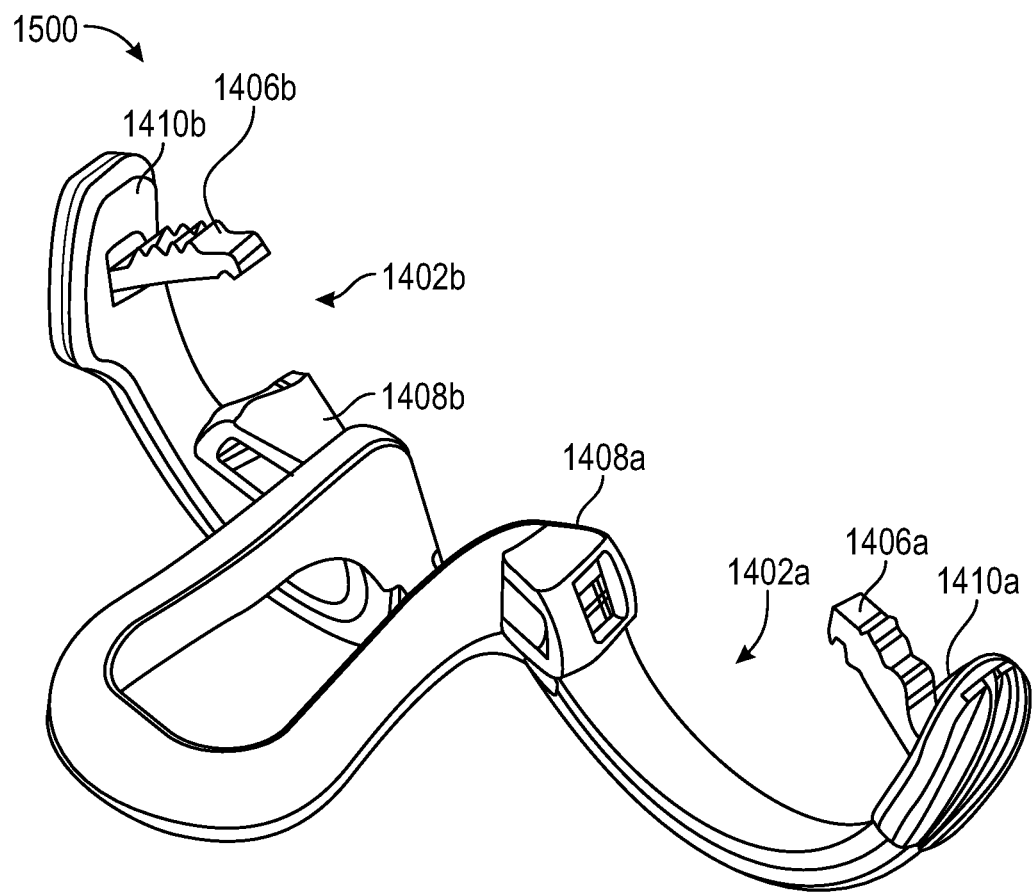
FIG. 15 is a front perspective view of a nasal dilator device, according to some embodiments.

In other embodiments, as depicted in FIG. 15, nasal dilator device 1500 having first and second releasable attachment mechanisms 1402a, 1402b may comprise first and second arms 1406a, 1406b extending from the respective opposite or inner surfaces 1410a, 1410b of the first and second nostril engaging elements 1312a, 1312b and first and second sockets 1408a, 1408b extending from the first and second intermediate sections 1308a, 1308b. In yet other embodiments, the first and second releasable attachment mechanisms 1402a, 1402b may comprise first and second arms 1406a, 1406b extending from the respective opposite or inner surfaces 1410a, 1410b of the first and second nostril engaging elements 1312a, 1312b and first and second sockets 1408a, 1408b extending from the first and second rib members 1310a, 1310b or the first and second leg members 1306a, 1306b.

Referring again to FIGS. 14A to 14E, the first and second arms 1406a, 1406b may include at least one or a series of serrations, detents or protrusions 1412 arranged to engage with at least one or a series of grooves or ridges 1414 provided on or within the sockets 1408a, 1408b. For example, the grooves or ridges 1414 may extend downwardly from a upper jaw portion 1416 of the sockets 1408a, 1408b and/or may extend upwardly from a lower jaw portion 1418.

Application of sufficient force by a user to the first and second releasable attachment mechanisms 1402a, 1402b may be effective to move the arms 1406a, 1406b with respect to the sockets 1408a, 1408b and overcome a restrictive force between the detents 1412 and the grooves 1414 to allow the detents 1412 and/or the grooves 1414 to deform and the degree or level of dilation to be adjusted. The engagement of the detents 1412 with the grooves 1414 may provide a sufficient restrictive force to hold the arms 1406a, 1406b fixed when provided in a user's nose.

As depicted in FIGS. 14A to 14E, the arms 1406a, 1406b may each comprise a stopper or catch 1420 provided at their free ends to prevent or hinder the arms 1406a, 1406b from disengaging from or withdrawing from the respective sockets 1408a, 1408b. For example, in some embodiments, the catch 1420 comprises a hook portion 1422 which is configured to cooperate with a corresponding notch 1424 disposed in an upper or lower jaw portion 1416, 1418 of the socket 1408a, 1408b. Application of a relatively large pulling force may be sufficient to cause the catch 1420 to disengage with the notch 1424 and to cause the arms 1406a, 1406b to withdraw from the sockets 1408a, 1408b.

Figure 14A:
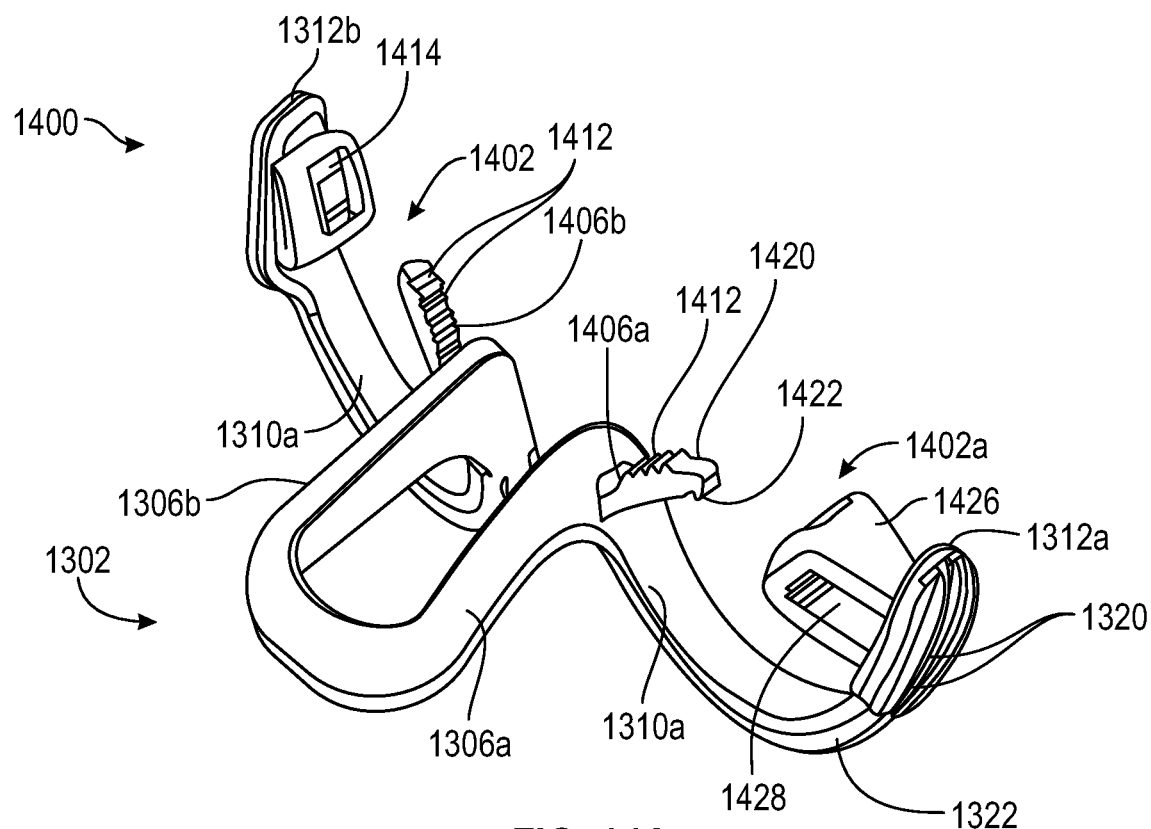
FIG. 14A is front perspective view of a nasal dilator device, according to some embodiments.
Figure 14B:
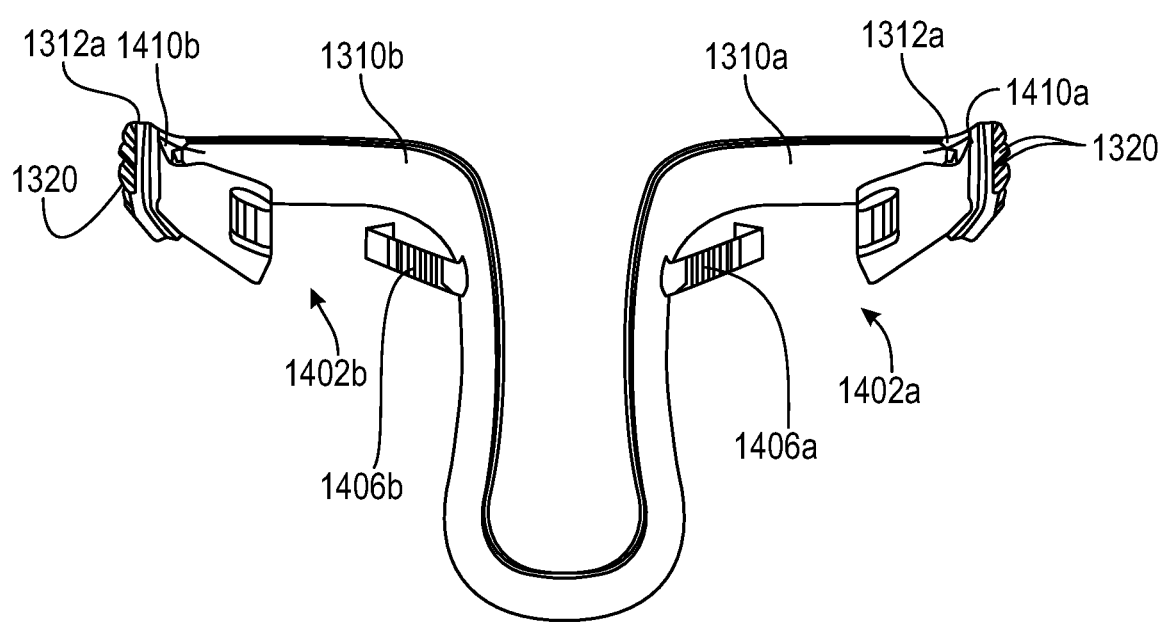
FIG. 14B is a top view of the nasal dilator device of FIG. 14A.
Figure 14C:
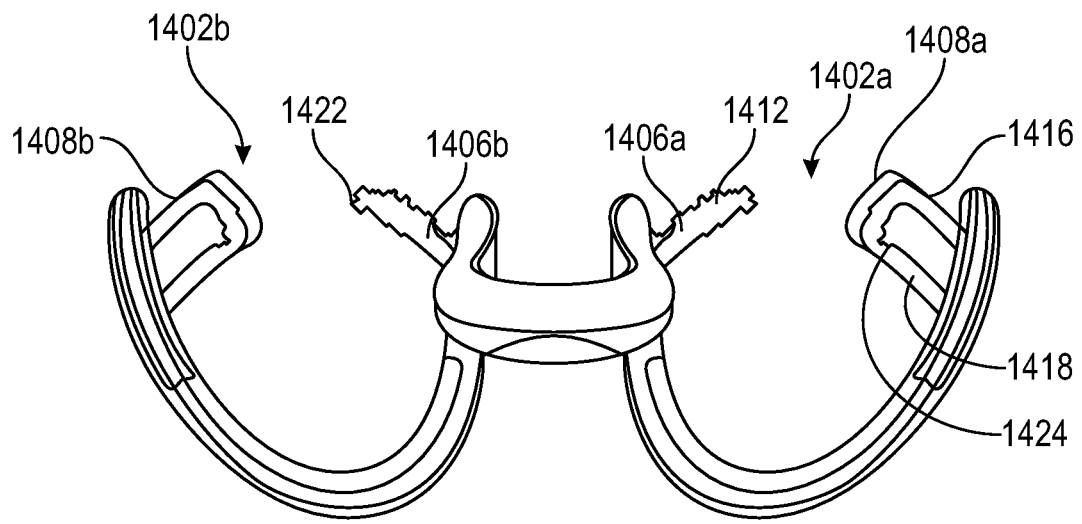
FIG. 14C is a front view of the nasal dilator device of FIG. 14A.
Figure 14D:
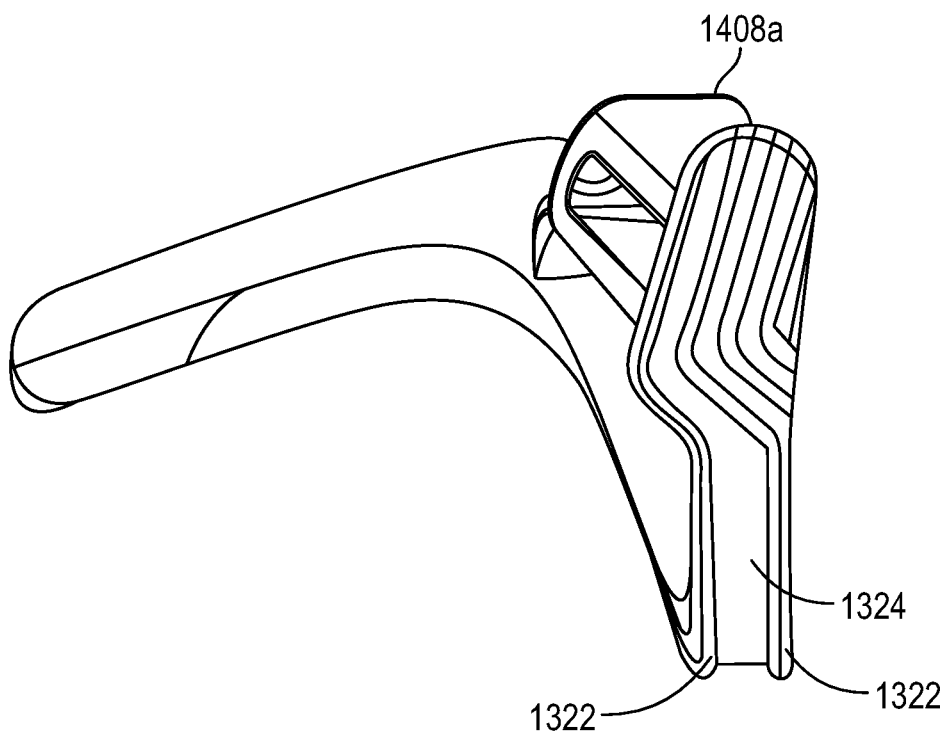
FIG. 14D is a side view of the nasal dilator device of FIG. 14A.
Figure 14E:
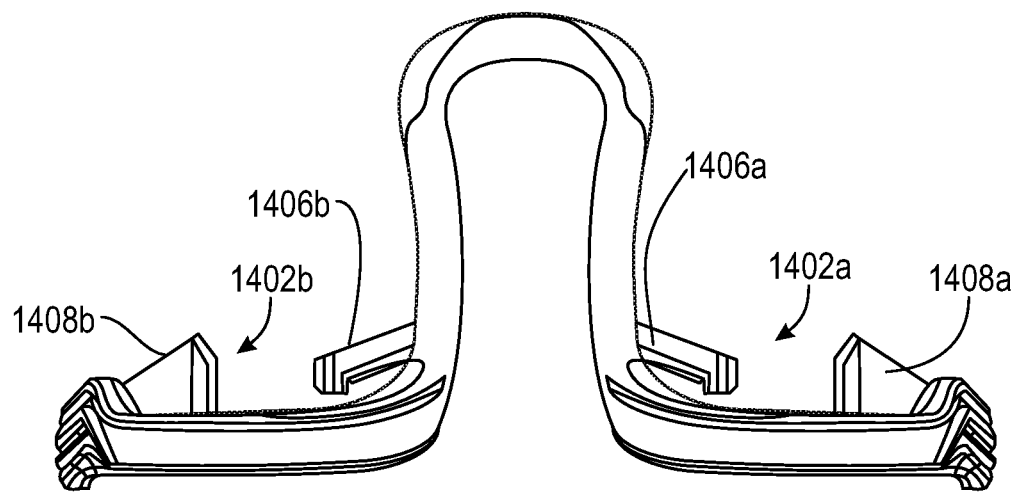
FIG. 14E is a bottom view of the nasal dilator device of FIG. 14A.
Figure 14F:
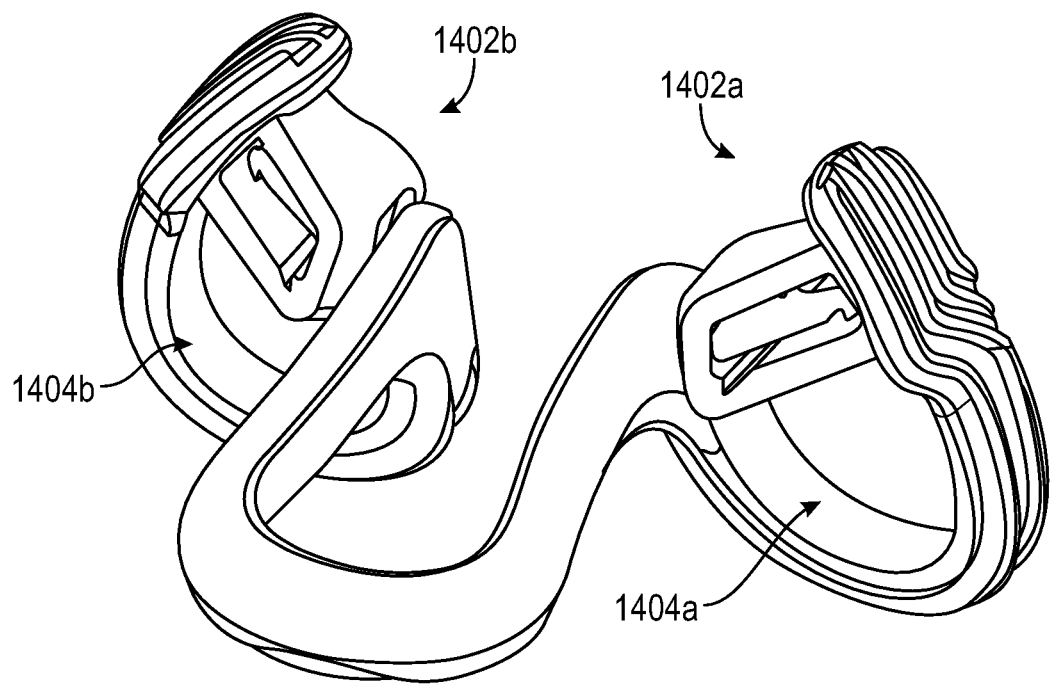
FIG. 14F is a front perspective view of the nasal dilator device of FIG. 14A in a closed state.

In some embodiments, as best shown in FIGS. 14A and 14B, the sockets 1408a, 1408b may take the form of substantially elongate housings 1426 provided with apertures 1428 or gaps in side walls of the housing 1426. The housings 1426 may be substantially wedge shaped and taper along their length towards opposite or inner surfaces 1410a, 1410b, of the first and second nostril engaging elements 1312a, 1312b to provide a relatively broad opening to receive the arms 1406a, 1406b. The elongate or wedge shaped housing 1426 may provide for an improved engagement between the arms 1406a, 1406b and sockets 1408a, 1408b and more robust releasable attachment mechanisms 1402a, 1402b. For example, the elongate or wedge shaped housing 1426 may allow a face 1430 of the socket housing 1426 to engage with and lie substantially flush to the intermediate sections 1308a, 1308b, rib members 1310a, 1310b, or leg members 1306a, 1306b, when the arms 1306a, 1306b are fully engaged within the sockets 1408a, 1408b, when the nasal dilator device 1400 assumes a closed configuration or state.

The arms 1406a, 1406b may be fully or substantially fully inserted into the respective sockets 1408a, 1408b to enable the nasal dilator device 1400 to adopt or assume a fully closed or substantially fully closed state, to thereby tighten or contract the looped structures 1411a, 1411b. The arms 1406a, 1406b may be partially inserted into the sockets 1408a, 1408b to enable the nasal dilator device 1400 to adopt or assume a partially closed state, to provide for looser or less tight looped structures 1404a, 1404b and accommodate variations in nasal passage sizes.

The particular configuration of the releasable attachment mechanisms 1402a, 1402b allows for self-adjustment of the looped structures, 1404a, and 1404b of the nasal dilator device 1400 whilst the device is in place of the nose of the user. This may be of particular benefit to a user partaking in percussive activities. For example, percussive activities, such as running or cycling, may cause a reduction in mechanical and frictional attachment of the nasal dilator device to a nasal passage of a user, for example, due to motion and/or skin perspiration, causing the device to move from a position intended by the user and therefore requiring readjustment.

As depicted in FIGS. 14A to 14F, the nasal dilator device 1400 may include a series of protrusions 1320 disposed on the nostril engaging members 1312a, 1312b, and/or one or more projections 1322 protruding from the major surface 1324 of the nasal dilator device 1400, as discussed with reference to FIG. 13.

Similar to the embodiment of nasal dilator device 600 depicted in FIG. 6, in some embodiments, the nasal dilator device 1400 may comprise at least one capsule (not shown), which may include an agent such as a medicament and/or a fragrance or aromatic agent, disposed within respective sockets 1408a, 1408b. The arms 1406a, 1406b may be configured to activate, pierce or burst the capsule (not shown) to release the agent, medicament and/or fragrance or aromatic agent when they are inserted into the sockets 1408a, 1408b. In this way, the medicament and/or fragrance or aromatic agent is released only when the capsule (not shown) is activated, pierced or burst, thereby increasing a longevity or "shelf-life" and/or protecting the integrity of the medicament and/or aromatic agent.

Similar to the embodiment of nasal dilator device 700 depicted in FIG. 7, in some embodiments, the nasal dilator device 1400 may comprise at least one coating or film (not shown) arranged to release a fragrance, aroma or medicament. For example, the film (not shown) may be disposed on a surface of at least one of the attachment mechanisms 1402a, 1402b, such as on an inner surface of the looped structures 1404a, 1404b, on the central portion 1302, on the first and second leg members 1306a, 1306b, on the first and second intermediate sections 1308a, 1308b, on the rib members 1310a, 1310b, and/or on the first and second nostril engaging elements 1312a, 1312b.

In some embodiments, the film (not shown) is arranged to release a fragrance, aroma or medicament in response to abrasion, such as scratching, scraping and may be provided with an outer cover, seal or strip to protect the film (not shown) from unintended abrasion. In other embodiments, the coating or film (not shown) may be arranged to release a fragrance, aroma or medicament in response to the removal or peeling off of an outer cover, strip or seal. In some embodiments, a fragrance, aroma or medicament may be provided or retained between two strips or films (not shown) forming a blister. For example, the coating or film (not shown) may comprise a polymer or a fibre and/or may be in the form of a "scratch and sniff" technology or peel off technology.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A nasal dilator device comprising:
a substantially U-shaped body including:
a central portion adapted to span a septum of a nose when worn by a user, and
a first leg member and a second leg member extending from the central portion in a first plane;
a first cantilever rib member extending outward from the U-shaped body in a second plane;
a second cantilever rib member extending outward from the U-shaped body in a third plane;
wherein the first cantilever rib member and the second cantilever rib member extend away from each other;
a first intermediate section connecting an end of the first leg member to a proximal end of the first cantilever rib member, wherein a proximal end of the first intermediate section is connected to the end of the first leg member and a distal end of the first intermediate section is connected to the proximal end of the first cantilever rib member, wherein the first intermediate section extends from the first plane to the second plane such that, when said nasal device is in use and is worn by a user, the first intermediate section extends from the first leg member substantially downwards towards a floor of a respective nasal passage to the first cantilever rib member;
a second intermediate section connecting an end of the second leg member to a proximal end of the second cantilever rib member, wherein a proximal end of the second intermediate section is connected to the end of the second leg member and a distal end of the second intermediate section is connected to the proximal end of the second cantilever rib member, wherein the second intermediate section extends from the first plane to the third plane such that, when said nasal device is in use and is worn by a user, the second intermediate section extends from the second leg member substantially downwards towards a floor of the respective nasal passage to the second cantilever rib member; and
at least one projection protruding from and extending along at least a portion of a length of each of the first and second cantilever rib members, and
a first and second releasable attachment mechanism for releasably attaching the first and second cantilever rib members, respectively, to the U-shaped body; and
wherein the first leg member and the second leg member are inclined towards each other such that a greater distance is provided between the first leg member and the second leg member at ends of the first and second leg members closest the central portion relative to a distance provided between the first leg member and the second leg member at the ends of the first and second leg members connected to the first and second intermediate sections respectively, and
wherein the first intermediate section and the second intermediate section are adapted, in use, to extend along a portion of the septum to the first cantilever rib member and the second cantilever rib member respectively, and
wherein the first cantilever rib member and the second cantilever rib member are elongated and arcuate rib members, each having a curvature along its length, wherein the first cantilever rib member and the second cantilever rib member extend arcuately from the first intermediate section and the second intermediate section respectively in a substantially upward direction from the floor of the respective nasal passage to an inner wall of a respective nostril along their length in the second and third planes respectively when the nasal device is worn by a user.

2. The nasal dilator device of claim 1, wherein the at least one projection is adapted, in use, to engage with an inner surface of a nose.

3. The nasal dilator device of claim 1, wherein the second and third planes are orthogonal to the first plane and/or wherein the second and third plane are the same plane.

4. The nasal dilator device of claim 1, wherein the first and second intermediate sections are adapted, in use, to engage with the septum and extend from the septum behind the columella and alar fibrofatty tissue of the nose, allowing the first and second cantilever rib members, in use, to be adapted to extend along respective nasal orifices to an inner wall of the nostrils.

5. The nasal dilator device of claim 1, wherein the second and third planes are converging or diverging planes such that the first and second cantilever rib members are angled and/or extend substantially toward the central portion of the U-shaped body.

6. The nasal dilator device of claim 1, wherein:
(i) each of the first cantilever rib member and the second cantilever rib member extend to a free distal end thereof, and/or
(ii) the first and second cantilever rib members exhibit an elongate arched profile which approximates at least a portion of one of a circle, ellipse or parabola.

7. The nasal dilator device of claim 1, wherein the first and second intermediate sections are inclined away from each other and adapted to assist in urging the respective first and second cantilever rib members against inner walls of respective nostrils when worn by the user.

8. The nasal dilator device of claim 1, wherein the first and second cantilever rib members comprise respective first and second nostril engaging elements comprising enlarged pads disposed thereon and adapted to engage with an inner wall of a respective nostril.

9. The nasal dilator device of claim 8, wherein:
the first and second nostril engaging elements extend arcuately from the respective first and second distal ends of the respective first and second cantilever rib members;
the first and second nostril engaging elements are disposed at distal ends of the first and second cantilever rib members, respectively; and/or
the enlarged pads comprise a series of protrusions.

10. The nasal dilator device of claim 8, further comprising a series of protrusions disposed on the first and second nostril engaging elements, optionally wherein:
the series of protrusions are formed from an overmould material;
the first and second nostril engaging elements are substantially elongate and the series of protrusions is adapted to extend along a length of the first and second nostril engaging elements; and/or the at least one projection is integrated with and extends from a corresponding protrusion of the series of protrusions.

11. The nasal dilator device of claim 8, wherein in use said device is adapted to be orientated in the nose such that the first and second nostril engaging elements are adapted to be positioned at a junction of the greater alar cartilage and lateral nasal cartilage.

12. The nasal dilator device of claim 11, wherein in use the first and second intermediate sections are adapted to extend along a length of the septum behind the columella and the fibrofatty tissue or bulbous region around the base of the nostrils, and the first and second cantilever rib members are each adapted to extend from a floor of the nasal passage behind the columella and the fibrofatty tissue or bulbous region around the base of the nostrils to an inner wall of the nostrils.

13. The nasal dilator device claim 1, wherein the first and second releasable attachment mechanisms each comprise an arm and a socket arranged to receive and engage the arm.

14. The nasal dilator device of claim 13, wherein a stopper or hook is disposed at an end of each arm to hinder the arm from withdrawing from the socket, and optionally a notch is disposed on an inner surface of each socket and is configured to engage with the stopper or hook on each arm to hinder the arms from withdrawing from the sockets.

15. The nasal dilator device of claim 13, wherein the arms are disposed on an inner surface of first and second nostril engaging elements of the first and second cantilever rib members, respectively, and the sockets are disposed on the first and second leg members or on the first and second intermediate sections.

16. The nasal dilator device of claim 13, wherein the sockets are disposed on an inner surface of first and second nostril engaging elements of the first and second cantilever rib members, respectively, and the arms are disposed on the first and second leg members or on the first and second intermediate sections.

17. The nasal dilator device of claim 13, further comprising first and second arm support members projecting from the first and second intermediate sections respectively, and wherein the sockets are disposed on an inner surface of first and second nostril engaging elements of the first and second cantilever rib members, respectively, and the arms are disposed on the first and second arm support members.

18. The nasal dilator device of claim 13, wherein the sockets comprise substantially elongate housings which taper along their length and provide a relatively broad opening for receiving the arms, and optionally each of the sockets is provided with apertures in side walls of the housing.

19. The nasal dilator device of claim 1, wherein the releasable attachment mechanisms are arranged to releasably attach first and second nostril engaging elements disposed at distal ends of the first and second cantilever rib members to (i) the first and second leg members respectively, or (ii) to the first and second intermediate sections respectively.

20. The nasal dilator device of claim 1, wherein the first and second releasable attachment mechanisms are adapted to allow a user to selectively adjust a degree of dilation or expansion and contraction of the first and second cantilever rib members with respect to the U-shaped body.

21. The nasal dilator device of claim 1, wherein in use the intermediate sections of said nasal dilator device are adapted to cause the first and second cantilever rib members to use the floor of the nose as a support structure for dilation of the nostrils.

22. The nasal dilator device of claim 21, wherein in use the first and second cantilever rib members are each adapted to exert an outward force on the inner wall of the nostril and on the floor of the nose to thereby dilate the nasal passage of the nose.

23. The nasal dilator device of claim 1, wherein:
(i) the at least one projection comprises first and second projections, each forming a flange disposed at a respective edge of a major surface of the nasal dilator device; and/or
(ii) distal ends of the first and second cantilever rib members are not connected to the first and second intermediate sections respectively.

24. The nasal dilator device of claim 1, wherein the first and second cantilever rib members (i) extend substantially upwardly along their length from the first and second intermediate sections respectively, and/or (ii) each comprise a plurality of angled or arcuate portions along their length.

25. The nasal dilator device of claim 1, wherein the first intermediate section extends substantially downward from the end of the first leg member to the proximal end of the first cantilever rib member, and the second intermediate section extends substantially downward from the end of the second leg member to the proximal end of the second cantilever rib member.

26. The nasal dilator device of claim 1, wherein when said nasal device is in use and is worn by a user:
the entire first intermediate section extends substantially downwards from the first leg member to the first cantilever rib member, and the entire second intermediate section extends substantially downwards from the second leg member to the second cantilever rib member; and/or
the entire first intermediate section transitions between the first plane and the second plane to interconnect the end of the first leg member to the proximal end of the first cantilever rib member, and the entire second intermediate section transitions between the first plane and the third plane to interconnect the end of the second leg member to the proximal end of the second cantilever rib member.

27. The nasal dilator device of claim 1, wherein each of the second and third planes forms an obtuse angle with the first plane such that the first and second intermediate sections are obtuse arcuate intermediate sections each having a substantially obtuse curvature along its length.

28. A nasal dilator device comprising:
a substantially U-shaped body including:
a central portion adapted to span a septum of a nose when worn by a user, and
a first leg member and a second leg member extending from the central portion in a first plane;
a first cantilever rib member extending outward from the U-shaped body in a second plane;
a second cantilever rib member extending outward from the U-shaped body in a third plane;
wherein the first cantilever rib member and the second cantilever rib member extend away from each other;
a first intermediate section connecting an end of the first leg member to a proximal end of the first cantilever rib member, wherein a proximal end of the first intermediate section is connected to the end of the first leg member and a distal end of the first intermediate section is connected to the proximal end of the first cantilever rib member, wherein the first intermediate section extends from the first plane to the second plane such that, when said nasal device is in use and is worn by a user with a head of the user in a substantially upright position, the first intermediate section extends from the first leg member substantially downwards towards a floor of a respective nasal passage to the first cantilever rib member;
a second intermediate section connecting an end of the second leg member to a proximal end of the second cantilever rib member, wherein a proximal end of the second intermediate section is connected to the end of the second leg member and a distal end of the second intermediate section is connected to the proximal end of the second cantilever rib member, wherein the second intermediate section extends from the first plane to the third plane such that, when said nasal device is in use and is worn by a user with a head of the user in a substantially upright position, the second intermediate section extends from the second leg member substantially downwards towards a floor of the respective nasal passage to the second cantilever rib member; and
at least one projection protruding from and extending along at least a portion of a length of each of the first and second cantilever rib members, and
wherein the first leg member and the second leg member are inclined towards each other such that a greater distance is provided between the first leg member and the second leg member at ends of the first and second leg members closest the central portion relative to a distance provided between the first leg member and the second leg member at the ends of the first and second leg members connected to the first and second intermediate sections respectively, and
wherein the first intermediate section and the second intermediate section are adapted, in use, to extend along a portion of the septum to the first cantilever rib member and the second cantilever rib member respectively, and
wherein the first cantilever rib member and the second cantilever rib member are elongated and arcuate rib members, each having a curvature along its length, wherein the first cantilever rib member and the second cantilever rib member extend arcuately from the first intermediate section and the second intermediate section respectively in a substantially upward direction from the floor of the respective nasal passage to an inner wall of a respective nostril along their length in the second and third planes respectively when the nasal device is worn by a user.

29. A nasal dilator device comprising:
a substantially U-shaped body including:
  a central portion adapted to span a septum of a nose when worn by a user, and
  a first leg member and a second leg member extending from the central portion in a first plane;
a first cantilever rib member extending outward from the U-shaped body in a second plane;
a second cantilever rib member extending outward from the U-shaped body in a third plane;
wherein the first and second cantilever rib members extend away from each other;
a first intermediate section connecting an end of the first leg member to a proximal end of the first cantilever rib member, wherein a proximal end of the first intermediate section is connected to the end of the first leg member and a distal end of the first intermediate section is connected to the proximal end of the first cantilever rib member, wherein the first intermediate section extends from the first plane to the second plane, such that, when said nasal device is in use and is worn by a user, the first intermediate section extends from the first leg member substantially downwards towards a floor of a respective nasal passage to the first cantilever rib member;
a second intermediate section connecting an end of the second leg member to a proximal end of the second cantilever rib member, wherein a proximal end of the second intermediate section is connected to the end of the second leg member and a distal end of the second intermediate section is connected to the proximal end of the second cantilever rib member, wherein the second intermediate section extends from the first plane to the third plane such that, when said nasal device is in use and is worn by a user, the second intermediate section extends from the second leg member substantially downwards towards the floor of the respective nasal passage to the second cantilever rib member;
a first releasable attachment mechanism for releasably attaching a distal end of the first cantilever rib member to the first intermediate section; and
a second releasable attachment mechanism for releasably attaching a distal end of the second cantilever rib member to the second intermediate section;
wherein the first leg member and the second leg member are inclined towards each other such that a greater distance is provided between the first leg member and the second leg member at ends of the first and second leg members closest the central portion relative to a distance provided between the first leg member and second leg member at the ends of the first and second leg members connected to the first and second intermediate sections respectively, and
wherein the first intermediate section and the second intermediate section are adapted, in use, to extend along a portion of the septum to the first cantilever rib member and the second cantilever rib member respectively, and
wherein the first cantilever rib member and the second cantilever rib member are elongated and arcuate rib members, each having a curvature along its length, wherein the first cantilever rib member and the second cantilever rib member extend arcuately from the first intermediate section and the second intermediate section respectively in a substantially upward direction from the floor of the respective nasal passage to an inner wall of a respective nostril along their length in the second and third planes respectively when the nasal device is worn by a user.

30. A nasal dilator device comprising:
a substantially U-shaped body including:
  a central portion adapted to span a septum of a nose when worn by a user, and
  a first leg member and a second leg member extending from the central portion in a first plane;
a first cantilever rib member extending outward from the U-shaped body in a second plane;
a second cantilever rib member extending outward from the U-shaped body in a third plane;
wherein the first cantilever rib member and the second cantilever rib member extend away from each other;
a first intermediate section connecting an end of the first leg member to a proximal end of the first cantilever rib member, wherein a proximal end of the first intermediate section is connected to the end of the first leg member and a distal end of the first intermediate section is connected to the proximal end of the first cantilever rib member, wherein, when said nasal device is in use and is worn by a user, the first intermediate section extends from the first leg member substantially downwards towards a floor of a respective nasal passage to the first cantilever rib member; and a second intermediate section connecting an end of the second leg member to a proximal end of the second cantilever rib member, wherein a proximal end of the second intermediate section is connected to the end of the second leg member and a distal end of the second intermediate section is connected to the proximal end of the second cantilever rib member, wherein, when said nasal device is in use and is worn by a user, the second intermediate section extends from the second leg member substantially downwards towards the floor of the respective nasal passage to the second cantilever rib member; and a first and second releasable attachment mechanism for releasably attaching the first and second cantilever rib members, respectively, to the U-shaped body;

wherein the first and second leg members are inclined towards each other such that a greater distance is provided between the first and second leg members at ends of the first and second leg members closest the central portion relative to a distance provided between the first and second leg members at the ends of the first and second leg members connected to the first and second intermediate sections respectively, and wherein the first and second intermediate sections are arcuate and are adapted, in use, to extend along a portion of the septum to the first and second cantilever rib members respectively, and wherein the first and second cantilever rib members are elongated and arcuate rib members, each having a curvature along its full length, and wherein the first and second cantilever rib members extend arcuately from the first and second intermediate sections respectively in a substantially upward direction from the floor of the respective nasal passage to an inner wall of a respective nostril along their length when the nasal device is worn by a user.

31. A nasal dilator device comprising:

a substantially U-shaped body including:

a central portion adapted to span a septum of a nose when worn by a user, and a first leg member and a second leg member extending from the central portion;

a first cantilever rib member and a second cantilever rib member extending outward from the U-shaped body and away from one another;

a first intermediate section connecting an end of the first leg member to a proximal end of the first cantilever rib member, wherein a proximal end of the first intermediate section is connected to the end of the first leg member and a distal end of the first intermediate section is connected to the proximal end of the first cantilever rib member, wherein, when said nasal device is in use and is worn by a user, the first intermediate section extends from the first leg member substantially downwards towards a floor of a respective nasal passage to the first cantilever rib member;

a second intermediate section connecting an end of the second leg member to a proximal end of the second cantilever rib member, wherein a proximal end of the second intermediate section is connected to the end of the second leg member and a distal end of the second intermediate section is connected to the proximal end of the second cantilever rib member, wherein, when said nasal device is in use and is worn by a user, the second intermediate section extends from the second leg member substantially downwards towards the floor of the respective nasal passage to the second cantilever rib member; and at least one projection protruding from and extending along at least a portion of a length of each of the first and second cantilever rib members; and a first and second releasable attachment mechanism for releasably attaching the first and second cantilever rib members, respectively, to the U-shaped body;

wherein the first and second leg members are inclined towards each other such that a greater distance is provided between the first and second leg members at ends of the first and second leg members closest the central portion relative to a distance provided between the first and second leg members at the ends of the first and second leg members connected to the first and second intermediate sections respectively, and wherein the first and second leg members are adapted, in use, to extend inward of respective nasal orifices along the septum;

wherein the first and second cantilever rib members are elongated and arcuate rib members each having a curvature along its length, and wherein the first and second cantilever rib members extend arcuately from the first and second intermediate sections respectively in a substantially upward direction from the floor of the respective nasal passage to an inner wall of a respective nostril along their length;

wherein the first and second intermediate sections are arcuate and are adapted, in use, to engage with the septum and to extend along a portion of the septum behind the columella and alar fibrofatty tissue of the nose to the first and second cantilever rib members respectively when the nasal device is worn by a user.

* * * * *